United States Patent [19]

Kang

[11] Patent Number: 5,858,646
[45] Date of Patent: Jan. 12, 1999

[54] MODIFIED HIV-POL POLYPEPTIDE HAVING IMMUNOLOGICAL ACTIVITY FOR USE AS DIAGNOSTIC REAGENT

[75] Inventor: C. Yong Kang, Gloucester, Canada

[73] Assignee: University of Ottawa, Ottawa, Canada

[21] Appl. No.: 743,357

[22] PCT Filed: Feb. 23, 1990

[86] PCT No.: PCT/CA90/00062

§ 371 Date: Aug. 21, 1991

§ 102(e) Date: Aug. 21, 1991

[87] PCT Pub. No.: WO90/10230

PCT Pub. Date: Sep. 7, 1990

[30] Foreign Application Priority Data

Feb. 23, 1989 [CA] Canada ...................................... 591908
Apr. 18, 1989 [GB] United Kingdom .................... 8908725

[51] Int. Cl.⁶ ...................................................... C12Q 1/70
[52] U.S. Cl. ................................ 435/5; 435/7.1; 435/7.2; 435/974; 435/975; 530/350; 530/826
[58] Field of Search ................................ 435/5, 7.1, 7.2, 435/974, 975; 530/350, 826

[56] References Cited

U.S. PATENT DOCUMENTS

| | | | |
|---|---|---|---|
| 4,745,051 | 5/1988 | Smith | 435/68 |
| 4,751,180 | 6/1988 | Cousens et al. | 435/68 |
| 5,194,376 | 3/1993 | Kang | 435/69.1 |

FOREIGN PATENT DOCUMENTS

| | | |
|---|---|---|
| 0196056 | 10/1986 | European Pat. Off. . |
| 0265785 | 5/1988 | European Pat. Off. . |
| 0322922 | 7/1989 | European Pat. Off. . |
| WOA87/04728 | 8/1987 | WIPO . |
| WOA87/07296 | 12/1987 | WIPO . |

OTHER PUBLICATIONS

Farmerie—'Science', vol. 236, Apr. 17, 1987.
Mous et al—'Journal of Virology', Apr. 1988, pp. 1433–1436.
Matthews & Bolognesi—'Scientific American', Oct. 1988—AIDS Vaccines.
Reagan—'The Lancet'—Jan. 27, 1990 p. 236.
Navia et al—'Nature', vol. 337, Feb. 16, 1989—Three-dimensional structure of aspartyl protease from human immunodeficiency virus HIV–1.
Kang—'Advances in Virus Research', vol. 35—Baculovirus Vectors For Expression of Foreign Genes.
Horiuchi et al—'Agric.Biol.Chem.,' 51(6), 1573–80 (1987).
Garson et al—'Virology' 177, 106–115 (1990).
Luo et al—'Virology', 179, 874–880 (1990).
Devash et al—'Nature', 1990—Antibodies against AIDS proteins.
Kozak—'Cell', vol. 44, pp. 283–292, Jan. 31, 1986 "Point Mutations . . .".
Sung et al—'Gene', 47, 1986, Synthesis of mutant parathyroid hormone genes . . .
Maeda et al—'Nature', vol. 315, Jun. 13, 1985 "Production of human α–interferon in silkworm using a baculovirus vector".
Hu et al—'Proc. Natl. Acad. Sci.,' Feb. 8, 1991—"Enzyme Activities in Four Different Forms of HIV–1 pol Gene Products".
Human Retroviruses and AIDS—1988—Dr. Gerald Myers, Chief Editor, Los Alamos National Laboratory, Los Alamos, NM 87545 U.S.A.
Farmerie et al, "Expression and Processing of the AIDS Virus Reverse Transcriptase in *Escherichia coli*", *Science*, vol. 236(17 Apr. 1987), pp. 305–308.
Mous et al, "Processing Protease and Reverse Transcriptase from Human Immunodeficiency Virus Type I Polyprotein in *Escherichia coli*", *Journal of Virology*, vol. 62, No. 4(Apr. 1988), pp. 1433–1436.

*Primary Examiner*—Jeffrey Stucker

[57] ABSTRACT

A polypeptide having immunological activity for use as a diagnostic reagent for the HIV. The polypeptide comprises a substantial portion of each of more than one of the constituent proteins coded for by the HIV-pol gene, namely the amino acid sequences of the reverse transcriptase, RNase H and integrase enzymes coded for by the HIV-pol gene and the amino acid sequences of part of the protease enzyme coded for by the HIV-pol gene, but omitting the active site responsible for proteolytic activity.

2 Claims, 4 Drawing Sheets

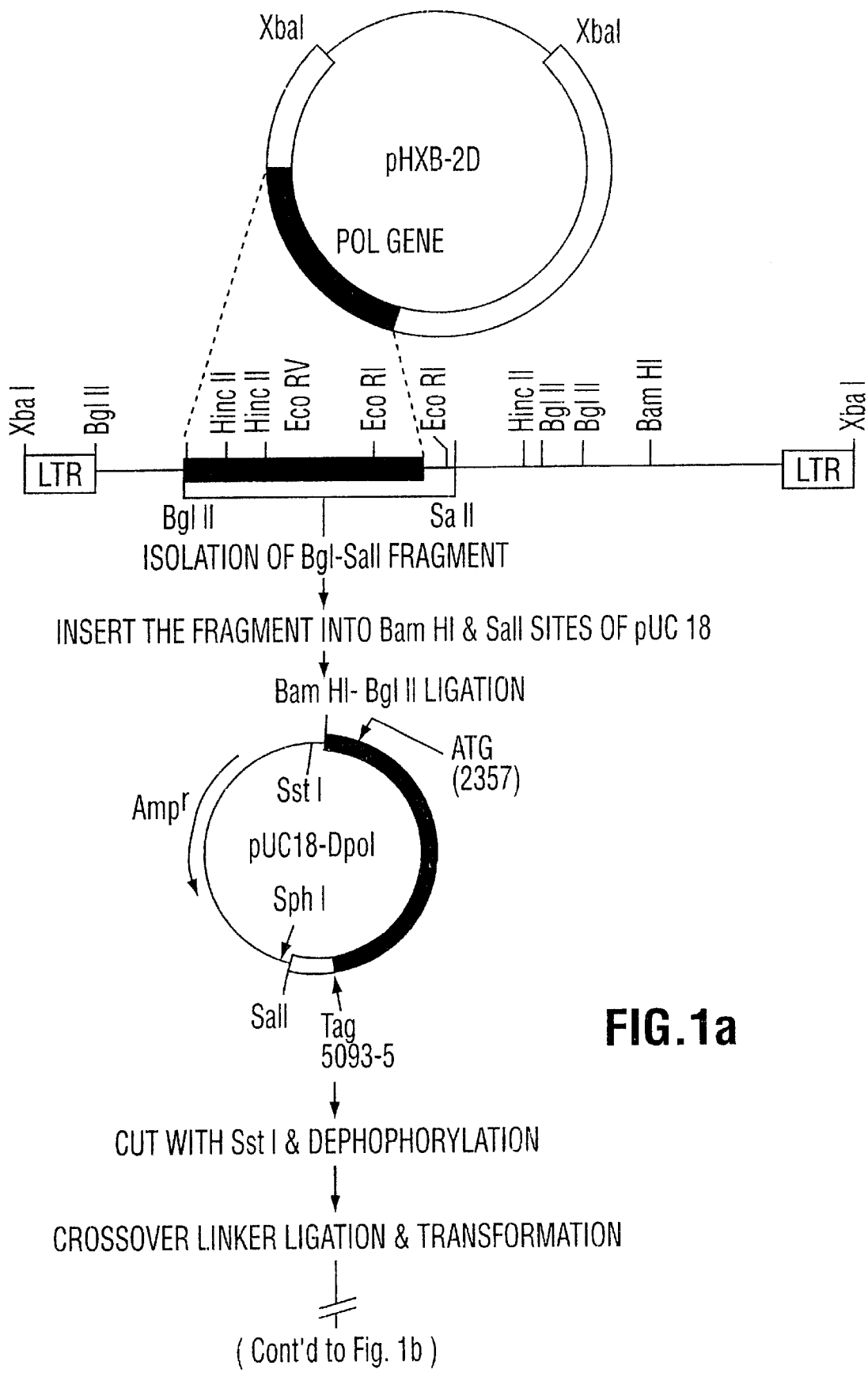

MODIFIED HIV-POL POLYPEPTIDE HAVING IMMUNOLOGICAL ACTIVITY FOR USE AS DIAGNOSTIC REAGENT

TECHNICAL FIELD

This invention relates to a polypeptide having immunological activity for use as a diagnostic reagent and/or a vaccine component.

BACKGROUND ART

Diagnostic kits for use in screening individuals for infection with human immunodeficiency virus (HIV) infection frequently include reagents comprising HIV antigens which are used to detect antibodies using known immunological techniques including ELISA, Western Blot, latex agglutination and immuno-luminescent and immuno-fluorescent techniques.

The effectiveness of such techniques however depends upon selection of suitable immunological reagents and one particular difficulty which arises is that particular reagents are often specific to individual strains or groups of strains of HIV. Thus, for example, known diagnostic reagents based upon HIV-1 may fail to detect antibodies resulting from an infection of a patient with HIV-2.

Similarly, in the production of vaccines designed to protect individuals against HIV infection, the use of antigens derived from one particular strain of HIV may fail to provide adequate protection against infection with other strains.

Synthesis and cleavage of the HIV-I pol precursor polyprotein is disclosed in "Processing Protease and Reverse Transcriptase from Human Immunodeficiency Virus Type I Polyprotein in *Escherichia coli*" by Jan Mous et. al., Journal of Virology, Apr. 1988, p. 1433–1436. The process disclosed in this reference results in the formation of a 92 kDa polypeptide consisting of protease (18 kDa), reverse transcriptase (64 kDa) and an amino-terminal portion of endonuclease (integrase) (10 kDa). The polyprotein is thus lacking the intact endonuclease sequence (25 kDa), and thus lacks substantial antigenic epitopes representing the endonuclease (integrase). Thus, the protein is unlikely to be suited for the preparation of diagnostic tests and vaccines for HIV-I.

It is an object of the present invention to overcome such problems.

DISCLOSURE OF INVENTION

It has now been found that the product of expressing a substantial part of the HIV-pol gene in a suitable host has antigenic properties which allows the above-mentioned problems to be overcome.

Thus according to one aspect of the present invention there is provided the use as an antigenic reagent in the diagnostic test or as a vaccine component of a polypeptide comprising a substantial portion of each of more than one of the constituent proteins coded for by the HIV-pol gene.

Diagnostic kits and vaccines comprising said polypeptide form further aspects of the present invention.

The HIV-pol gene codes for four enzymes, namely a protease, a reverse transcriptase, a ribonuclease referred to as RNAse H and an enzyme referred to as Integrase.

It is believed that during infection of a T cell by HIV a full length precursor is expressed which is then cut up into the discrete proteins listed above. These have the following activities and (it is thought) act in the order indicated:

| Protease | Precursor cleavage |
|---|---|
| Reverse Transcriptase | Preparation of viral DNA from viral RNA |
| RNase H | Destruction of viral RNA leaving newly synthesised DNA |
| Integrase | Insertion of said DNA into host cell genome |

According to a preferred aspect of the present invention, said constituent proteins are enzymes coded for by the HIV-pol gene and the polypeptide thus comprises a substantial portion of each of a plurality of enzymes selected from HIV-pol protease, HIV-pol reverse transcriptase, HIV-pol RNAse H and HIV-pol Integrase. Most preferably, the polypeptide comprises substantial portions of all four of said enzymes.

In vivo, the initial product of expressing the HIV-pol gene is cleaved into its individual elements by the protease. The active site for proteolytic activity occurs adjacent the $NH_2$-terminus of the expression product, corresponding to the 5'-end of the protease gene.

According to a preferred aspect of the present invention, the polypeptide omits at least that part of the amino acid sequence of the HIV-pol protease gene which codes for the active site responsible for proteolytic activity. By omitting this portion, the integrity of the polypeptide is maintained and it is less liable to degrade.

BRIEF DESCRIPTION OF DRAWINGS

FIGS. 1*a* and 1*b* together form a schematic diagram showing the procedure of Example 1;

BEST MODE FOR CARRYING OUT THE INVENTION

Figure 1B:
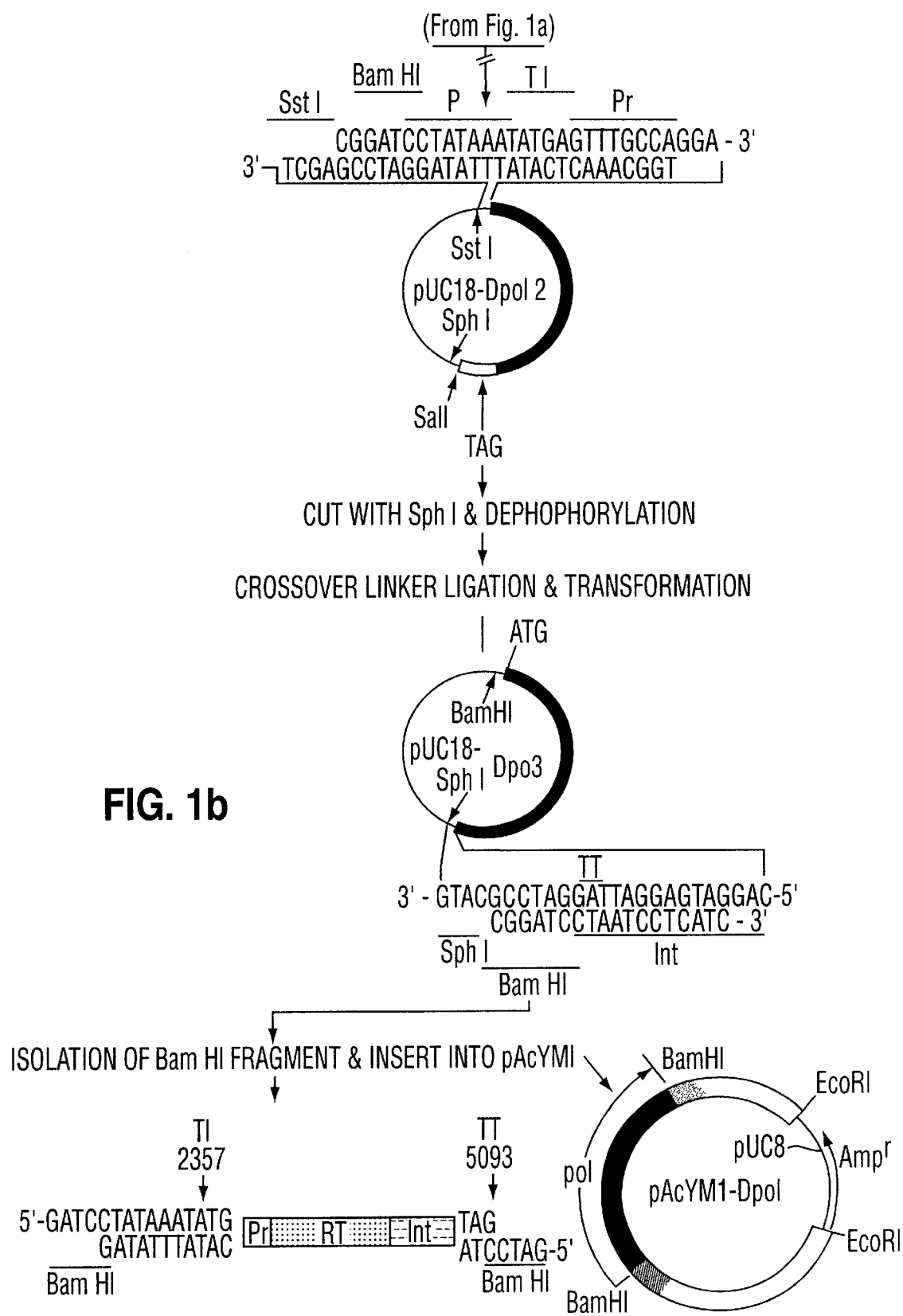

The HIV-pol gene of several strains of HIV-1 has been cloned and the corresponding amino acid sequences derived from the determined DNA sequences. The amino acid sequences of ten strains appear in the accompanying Table 1 at the end of this disclosure [SEQ ID Nos:1–10, respectively]. In Table 1, the full sequence of strain HIV HXB2[SEQ ID NO:1] is given, whereas for the other nine strains, only sequence differences are listed. As used herein, the term "constituent protein coded for by the HIV-pol gene" refers to a protein having sufficient amino acid homology with the sequence of HIV HXB2 appearing in the accompanying Table so as to result in antibodies raised against the protein cross-reacting with a polypeptide consisting of the precise amino acid sequence of HIV HXB2[SEQ ID NO:1].

The HIV-pol gene can be expressed to produce the desired polypeptide by various techniques, e.g. some or all of the baculovirus techniques described in U.S. Pat. No. 4,745,051 to Gale E. Smith et al issued on May 17, 1988; Baculovirus Vectors for Expression of Foreign Genes by C. Yong Kang, Advances in Virus Research, Vol. 35, pp 177–192, Academic Press Inc., 1988; A Manual of Methods for Baculovirus Vectors and Insect Cell Culture Procedures, Max D. Summers and Gale E. Smith, May 1987, Texas A&M University; and Baculoviruses as Gene Expression Vectors, Lois K. Miller, Ann. Rev. Microbiol. 42, pp 177–1991; the disclosures of which are incorporated herein by reference. However our Canadian Patent Application Serial No. 591,908 filed on 23rd Feb. 1989 (and equivalent British Patent Application Serial No. 89 04426.7 filed on Feb. 27, 1989 and U.S. patent application Ser. No. 316,768 filed on Feb. 28, 1989) describes and claims an improved baculovirus expression system capable of producing foreign gene proteins at high levels and the use of this expression system is particularly preferred for expressing the polypeptide of the present invention.

The process disclosed in our Canadian patent employs a recombinant baculovirus containing at least a major part of a polyhedrin gene promoter region, a transcription termination sequence of a polyhedrin structural gene, a foreign structural gene (e.g. an HIV-pol gene) having a translation start codon followed by coding sequences and a translation stop codon. The foreign gene is located between the promoter region and the termination sequence. Immediately upstream of the start codon there is a putative insect cell ribosome binding site for the polyhedrin gene effective for overcoming resistance of susceptible insect cells to express the foreign gene at a high level. The putative ribosome binding site comprises at least the final four nucleotides of the sequence 5'-ACCTATAAAT-3' [SEQ ID NO:11].

Example 3 of the Canadian application describes the production of the pol protein of HIV-1 in a baculovirus expression system based on *Autographa californica* nucleopolyhedrosis virus (ACNPV) and specifies that a recombinant baculovirus designated ACNPV-HIV-YK-pol has been deposited at the American Type Culture Collection of 12301 Parklawn Drive, Rockville Md. 20852, USA under Accession No. ATCC VR 2233. Deposit was made on Nov. 30, 1988. The disclosure of our Canadian Patent Application Serial No. 591,908 is incorporated herein by reference.

Utilising the procedures described in Example 3 of Canadian Patent Application Serial No. 591,908, a polypeptide comprising the protease, RNose H and Integrase enzymes of HIV strain HIV-XB2 may be produced.

The polypeptide can be used as a diagnostic reagent or vaccine component in ways known to persons skilled in the art, e.g. by the techniques indicated in the publication entitled Clinica, Testing for HIV and AIDS, The Next Five Years, George Street Publications Ltd., Richmond, Surrey, UK, the disclosure of which is incorporated herein by reference.

The invention is illustrated in more detail by the following Examples. Example 1 illustrates the production of a modified recombinant plasmid pUC18-Dpol3 having a 273 bp deletion at the 5'-terminus and its expression as polypeptide lacking the first 91 amino acids at the NH$_2$-terminus of the HIV-pol protease. Examples 2 and 3 relate to the expression of the polypeptide and its use as a diagnostic reagent.

EXAMPLE 1
Construction of baculovirus transfer vector containing HIV-1 pol gene with 273 bp deletion at 5' terminus As illustrated in FIGS. 1a and 1b the BglII and SalI fragment of plasmid pHXB-2D containing the HIV-1 pol coding region was isolated and inserted into BamHI and SalI sites of pUC18. The resulting recombinant plasmid (pUC18-Dpol 1) was cut with Sst1 and dephosporylated. A synthetic double-stranded crossover linker [SEQ ID NO:12 and SEQ ID NO:13] containing a Sst1 cohesive end, a BamHI site, the putative insect *Spodoptera frugiperda* (SF9) cell ribosome binding site (P) and 15 nucleotides of the homology searching sequences which overlaps with the 5' terminus of the pol gene was ligated at the Sst1 site and transformed. The recombinant plasmid, (pUC18-Dpol 2) was isolated, digested with sPH1, dephosphorylated and ligated with another crossover linker DNA [SEQ ID NO:14 and SEQ ID NO:15] containing SphI cohesive end at the 3' terminus, BamH1 site and 15 nucleotides of the homology searching sequences which recognise the 3' terminus of the pol gene. The resulting recombinant plasmid (pUC18-Dpol 3) contains the putative SF9 cell ribosome binding site (P) followed with pol open reading frame [SEQ ID NO:16] starting with the first ATG (TI) codon (map unit 2357–2359) in the pol gene and the translation termination (TT) codon TAG (map unit 5093–5095). This whole cassette was flanked with BamH1 sites. The BamH1 fragment commencing with the sequence GATCCTATAAATATG [SEQ ID NO:17] and the shorter complementary sequence CATATTTATAG (listed in the 5'-3' direction) [SEQ ID NO:18] was isolated and inserted into the BamH1 site of the pAcYM1 baculovirus transfer vector (pAcYM1-Dpol). The pAcYM1-Dpol transfer vector DNA was used to co-transfect SF9 cells with wild type AcNPV DNA to isolated recombinant AcNPV HIV-YK pol virus.

EXAMPLE 2
Expression of pol gene products by recombinant baculoviruses

Recombinant AcNPV-HIVWHpol contains an insert comprising essentially the whole DNA sequence of the HIV-pol gene (SEQ ID NO:19, see Table 2 at the end of the present disclosure). When expressed, the resulting full length gene product of the HIV-pol gene is "processed", i.e. the proteolytic active site of the HIV pol protease gene cleaves the protein into 66 kD, 51 kD and 32 kD fragments.

By way of comparison, recombinant AcNPV-HIVYKpol (SEQ ID NO:20, see Table 3 at the end of the present disclosure) omits NH$_2$-terminal amino acid sequences of the HIV-pol gene [SEQ ID NO:21] containing the proteolytic active site of the HIV-pol protease. When expressed, the resulting gene product [SEQ ID NO:22] is not "processed" i.e. the ~95 kD protein remains intact.

The following experiments illustrate this.

Figure 2A:
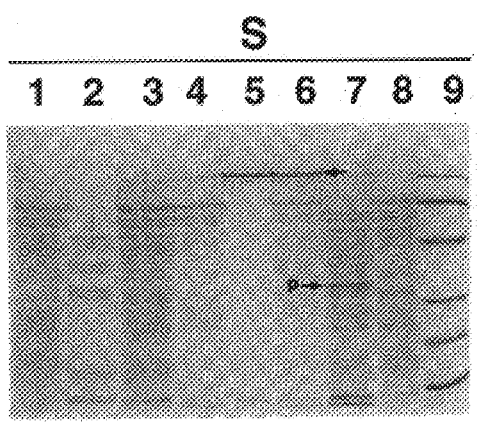
FIGS. 2*a* and 2*b* together show the results of electrophoresis tests carried out in the manner explained in Example 2.
Figure 2B:
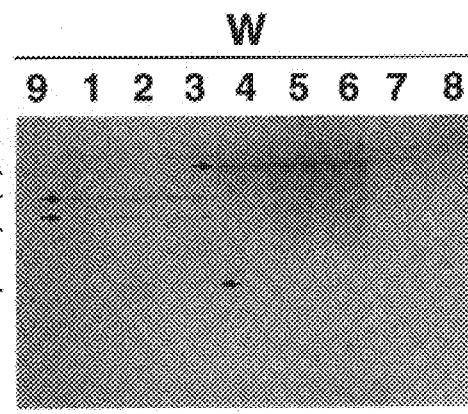

Uninfected *S. frugiperda* (SF9) cells, or SF9 cell infected with recombinant baculoviruses AcNPV-HIVWHpol, AcNPV-HIVYKpol or with wild-type AcNPV, were harvested after 72 hours of infection. Lysates of the infected or uninfected cells were electrophoresed in a 12% polyacrylamide Laemmli gel and proteins are identified by either Coomassie blue staining (S) or Western blot analyses (W) using the standard HIH HIV positive immunoglobulin. As shown in FIGS. 2a and 2b, lanes 1, 2 and 3 represents the lysates of AcNPV-HIVYHpol recombinant virus infected cells, lanes 4, 5 and 6 represent the lysates of AcNPV-HIVYKpol recombinant virus infected cells, lane 7 shows the wild-type ACNPV infected cell lysate, lane 8 shows uninfected cell lysate and lane 9 shows molecular weight markers. Lane 3 and 6 show the whole cell lysate, lanes 2 and 5 show proteins in the infected cell nuclei and lanes 1 and 4 show proteins in the infected cell cytoplasm. P denotes polyhedrin protein and arrows show 95K Dal uncleaved pol gene product representing 91 amino acid deletion of protease produced by AcNPV-HIVYKpol virus and 66K Dal, 51K Dal and 33K Dal processed pol gene products in AcNPV-HIVYHpol virus infected cells.

EXAMPLE 3
A. Production of pol gene product

Recombinant ACNPV-HIVYKpol virus infected *Spodoptera frugiperda* (SF9) cells were harvested 4 days after infection. Nuclei of infected cells containing most of the pol gene product were isolated by treating the infected cells with 0.1% Triton X-100 and 0.5% NP40 on ice for 20 minutes followed by centrifugation at 750 g for 10 minutes. The pelleted nuclei were denatured with 1% SDS in TRIS-HCl pH 8.0 at room temperature for 30 minutes. The cellular DNAs were removed by ethanol precipitation using 2 volumes of 100% ethanol. The SDS in the solution were removed by addition of 25 mM KCL incubated at 4° C. for 30 minutes followed by centrifugation at 12,700 g for 15 minutes. The pol gene product in the supernatant was used for anti-pol ELISA.

B. Detection of HIV antibodies by ELISA

The pol antigen was diluted in PBS and dispensed in a microtiter plate (Nunc cat 269620). The concentration of pol to coat plates was determined empirically on the strength of bands on polyacrylamide gels.

The concentration of pol necessary to coat one well was between 1 and 10 μg.

The plate was covered and incubated at 4° C. The time of incubation varied between 12 and 24 hrs without no apparent differences in reactivity.

The plates were then washed three times in PBS tween 20 employing a Skatron plate washer.

Various standards, NIH HIV+ immunoglobulin (NIH STD), pool HIV+ plasma (PAT STD) and plasma from non-infected individuals (NS) were employed. The standards were diluted beginning at 1:200 for NIH STD, and 1:10 for PAT STD and NS. Unknowns were tested usually at 1:50 but dilutions as high as 1:10 can be employed.

All samples were inactivated before testing. Normal sera were processed in the same fashion as sera from AIDS patients. The inactivation was performed with 4'-aminoethyltrioxsalen-hydrochloride (AMT) from Lee Biomolecular Research Inc. (San Diego, Calif. cat 231) and an ultra violet light trans-illuminator (Spectroline model TC-365, Fisher Scientific Ottawa Ont.). The AMT was reconstituted in 50% ethanol at 1 μg/ml. The sera was aliquoted in Eppendorf tubes and for every 100 μl of serum or plasma, 10 μl of AMT was added to the sample. The samples were layed in the transilluminator and irradiated for 5 minutes. An additional 10 μl of AMT was added to the sample and the samples were irradiated for a further 5 minutes. The samples were inactivated by this procedure.

The incubation time of the human-anti-pol was 30 to 40 minutes at room temperature (23° C.) (the time of incubation found to be quite critical). Therefore, all dilutions of standards (negative and positive) and unknowns was performed in a separate plate. Once all dilutions were done, the dilutions (100 μl) were transferred to the ELISA plate coated with pol employing a multichannel pipettor. All dilutions were with PBS Tween 20 (0.1%).

The state of the serum or plasma sample was found to be important. Samples repeatedly frozen and thawed usually gave higher backgrounds. This was especially evident with samples from normal individuals.

The plates were washed three times in PBS-Tween 20 after the 30 minute incubation with the first antibody. A Skatron II plate washer was employed for this purpose.

The second antibody used (goat anti-human Ig linked to horse radish peroxidase) was an affinity purified reagent obtained from Tago Diagnostics (Inter Medico To DNT cat 2393). An appropriate dilution was determined experimentally (approximately 1:2,000) is made in PBS-Tween 20 (0.1%). 100 μl was dispensed into the wells except for one which will be employed as a blank for the plate reader. The plate was incubated for 1 hour at room temperature.

The plates were washed three times with PBS-Tween 20 employing the Skatron II plate washer.

Freshly prepared substrate (100 μl) was added to the wells and after 20 minutes the reaction stopped with the addition of 100 μl of 0.07M H2SD4.

The plate was read at 450 nm in the BIOTEK BL/310 ELISA plate reader. A hard copy of the data was obtained from the reader and the data also stored directly onto computer diskette for further processing by the Anelisar program.

Additionally, controls were also performed on each plate. In two or three wells no serum or plasma was added. In one well no primary or secondary antibodies were added but substrate was. This well was employed to blank the ELISA plate reader. The remaining wells were employed to determine the extent of binding of the secondary antibody (Goat anti-HIg-HRPO) to POL. Thus, these wells received no primary antibody but secondary antibody and substrate with the appropriate washes in between each incubation. Usually the value of this latter control is below 0.1000 OD.

Figure 3:
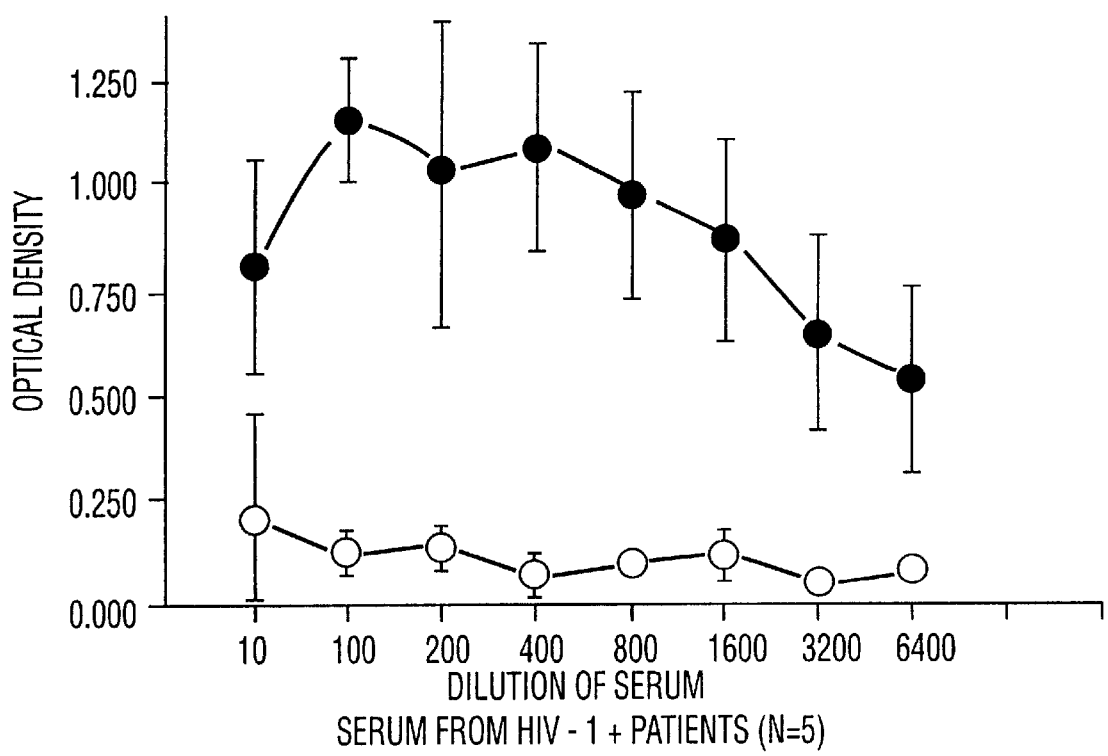
FIG. 3 is a graph showing the results of the experiments carried out in Example 3.

The results are shown in FIG. 3. The solid circles show the average of the results from plasma samples from five different HIV patients (N=5), and the open circles show the average of the results from the plasma from five non-infected individuals (control) at different levels of dilution. In each case, the vertical lines passing through the solid or open circles show the standard deviations of the individual results.

The following materials were use for the anti-pol ELISA procedure

Buffers

| Phosphate Buffered Saline (PBS) | |
|---|---|
| $Na_2HPO_4$ (dibasic anhydrous) | 13.6 g |
| $NaH_2PO_4$ (monobasic) | 2.4 g |
| NaCl | 90.0 g |

Salts are dissolved in 8 litres of distilled deionized water and pH is adjusted to 7.2 with NaOH or HCl. This buffer is employed as coating buffer, diluent and washing buffer. The latter two buffers are modified as indicated below.

Diluent for primary and secondary antibodies and washing buffer

PBS+0.1% Tween 20 (Sigma, St. Louis Mo.) (0.1 ml Tween 20+100 ml PBS). The diluent buffer is made up daily.

Substrate buffer

Equal volumes of 0.1M $Na_2HPO_4$ (0.709 g/50 ml) and 0.1M citric acid (0.960 g/50 ml). The pH is adjusted to 4.0 with NaOH or HCl. The substrate buffer is made up weekly.

Substrate

A tablet (2 mg) of o-phenylenediamine (Sigma cat. P6787) is dissolved into 10 ml of substrate buffer. Hydrogen peroxide (4 μl of 30%) is added to the solution just prior to plating. The solution should be kept in the dark as much as possible.

Stopping reagent

The enzymatic reaction is stopped with 0.07M $H_2SO_4$.

It is a particularly advantageous feature of the polypeptides, the use of which is described herein, that they cross-react with antibodies against diverse strains of HIV. Thus, for example, the polypeptides described herein based on HIV-1 can cross-react with antibodies raised against various strains of HIV-1 and HIV-2. Thus they may be used in diagnostic kits for detecting either virus category. Similarly, in vaccines they can provide broad-spectrum protection.

Industrial Applicability

As will be apparent from the above, the present invention can be used in the medical field for testing for HIV infection and for immunizing against HIV infection, as well as for other diagnostic or prognostic purposes.

TABLE 1

HIV-1 pol protein sequence of HIVHXB2 virus
Data from Human Retroviruses and AIDS 1988 Los Alamos National Laboratory AcNPV-HIVWHpol

| | | |
|---|---|---|
| HIVHXB2 | MetPhe Phe ArgGlu AspLeuAla Phe LeuGln Gly Lys Ala ArgGlu Phe Ser Ser Glu... | 19 |
| HIVBH102 | ------------------------------------------------------Gln | 20 |
| HIVBH5 | ------------------------------------------------------Gln | 20 |
| HIVPV22 | ------------------------------------------------------Gln | 20 |
| HIVBRU | ------------------------------------------------------Gln | 20 |
| HIVMN | .....................................................--- | 0 |
| HIVSF2 | ---------------------------------------------------------- | 19 |
| HIVRF | -----------Asn---------Pro-----------------Leu----------- | 19 |
| HIVMAL | -----------Asn---------Pro-------------------Pro--------- | 19 |
| HIVELI | -----------Asn---------Pro-----------Gly---Leu---Pro Lys--- | 19 |

| | | |
|---|---|---|
| HIVHXB2 | ..................................Gln Thr ArgAla AsnSer Pro Thr Arg | 28 |
| HIVBH102 | Thr ArgAla AsnSer Pro Thr Ile Ser Ser Glu------------------------- | 40 |
| HIVBH5 | Thr ArgAla AsnSer Pro Thr Ile Ser Ser Glu------------------------- | 40 |
| HIVPV22 | Thr ArgAla AsnSer Pro Thr Ile Ser Ser Glu------------------------- | 40 |
| HIVBRU | Thr ArgAla AsnSer Pro Thr Ile Ser Ser Glu------------------------- | 40 |
| HIVMN | ----------------------------------............................ | 0 |
| HIVSF2 | ---------------------------------------------------------- | 28 |
| HIVRF | ---------------------------------------------------------- | 28 |
| HIVMAL | -------------------------------------------------------Ser | 28 |
| HIVELI | -------------------------------------------------------Ser | 28 |

| | | |
|---|---|---|
| HIVHXB2 | ArgGlu LeuGln Val Trp Gly ArgAspAsnAsnSer Pro Ser Glu Ala Gly Ala AspArg | 48 |
| HIVBH102 | ---------------------------------------------------------- | 60 |
| HIVBH5 | ---------------------------------------------------------- | 60 |
| HIVPV22 | ---------------------------------------------------------- | 60 |
| HIVBRU | ---------------------------------Leu--------------------- | 60 |
| HIVMN | ............................................................ | 0 |
| HIVSF2 | --------------------Gly Glu---------Leu--------------------- | 48 |
| HIVRF | ---------------Leu-------------...----Glu------ | 47 |
| HIVMAL | ---------Arg---------Gly---... Lys Thr Leu------Thr------Glu--- | 47 |
| HIVELI | ---------Arg-------------------... Pro Leu--- Lys Thr------Glu--- | 47 |

| | | |
|---|---|---|
| HIVHXB2 | Gln Gly Thr Val Ser Phe AsnPhe Pro Gln Val Thr LeuTrp Gln ArgPro Leu Val Thr | 68 |
| HIVBH102 | --------------------------------Ile-------------------------- | 80 |
| HIVBH5 | --------------------------------Ile-------------------------- | 80 |
| HIVPV22 | --------------------------------Ile-------------------------- | 80 |
| HIVBRU | --------------------------------Ile-------------------------- | 80 |
| HIVMN | ............................................................ | 0 |
| HIVSF2 | --------------------------------Ile-------------------------- | 68 |
| HIVRF | -----------------Ser---------Ile-----------------Ile------ | 67 |
| HIVMAL | ------Ile---------Ser---------Ile-----------------Val------ | 67 |
| HIVELI | --------------------------------Ile------------------------Ala | 67 |

| | | |
|---|---|---|
| | <- gag cds end | |
| HIVHXB2 | Ile Lys Ile Gly Gly Gln LeuLys Glu Ala LeuLeu AspThr Gly Ala AspAspThr Val | 88 |
| HIVBH102 | ------------------------------------------------------------ | 100 |
| HIVBH5 | ------------------------------------------------------------ | 100 |
| HIVPV22 | ------------------------------------------------------------ | 100 |
| HIVBRU | ------------------------------------------------------------ | 100 |
| HIVMN | ............................................................ | 0 |
| HIVSF2 | ---Arg------------------------------------------------------ | 88 |
| HIVRF | Val--------------------------------------------------------- | 87 |
| HIVMAL | Val ArgVal-------------------------------------------------- | 87 |
| HIVELI | ------------------------------------------------------------ | 87 |

TABLE 1-continued

HIV-1 pol protein sequence of HIVHXB2 virus
Data from Human Retroviruses and AIDS 1988 Los Alamos National Laboratory AcNPV-HIVWHpol

|          |                                                                                                   |     |
|----------|---------------------------------------------------------------------------------------------------|-----|
|          | AcNPV-HIVYKpol starts                                                                             |     |
| HIVHXB2  | Leu Glu Glu Met Ser Leu Pro Gly Arg Trp Lys Pro Lys Met Ile Gly Gly Ile Gly Gly                   | 108 |
| HIVBH102 | ----------------------------------------------------------------                                  | 120 |
| HIVBH5   | ----------------------------------------------------------------                                  | 120 |
| HIVPV TABLE 1-continued HIV-1 pol protein sequence of HIVHXB2 virus
Data from Human Retroviruses and AIDS 1988 Los Alamos National Laboratory AcNPV-HIVWHpol

| | | |
|---|---|---|
| HIVHXB2 | Asn Pro Tyr Asn Thr Pro Val Phe Ala Ile Lys Lys Lys Asp Ser Thr Lys Trp Arg Lys | 228 |
| HIVBH102 | ------------------------------------------------------------ | 240 |
| HIVBH5 | ------------------------------------------------------------ | 240 |
| HIVPV22 | ------------------------------------------------------------ | 240 |
| HIVBRU | ------------------------------------------------------------ | 240 |
| HIVMN | ------------------------------------------------------------ | 137 |
| HIVSF2 | ------------------------------------------------------------ | 228 |
| HIVRF | ------------------------------------------------------------ | 227 |
| HIVMAL | ------------------------------------------------------------ | 227 |
| HIVELI | ----------------- Ile -------------------------------------- | 227 |

| | | |
|---|---|---|
| HIVHXB2 | Leu Val Asp Phe Arg Glu Leu Asn Lys Arg Thr Gln Asp Phe Trp Glu Val Gln Leu Gly | 248 |
| HIVBH102 | ------------------------------------------------------------ | 260 |
| HIVBH5 | ----------------------- Arg -------------------------------- | 260 |
| HIVPV22 | ------------------------------------------------------------ | 260 |
| HIVBRU | ------------------------------------------------------------ | 260 |
| HIVMN | -------------------------- Lys ----------------------------- | 157 |
| HIVSF2 | ------------------------------------------------------------ | 248 |
| HIVRF | ------------------------------------------------------------ | 247 |
| HIVMAL | ------ Asn ------------------------------------------------- | 247 |
| HIVELI | ------------------------------------------------------------ | 247 |

| | | |
|---|---|---|
| HIVHXB2 | Ile Pro His Pro Ala Gly Leu Lys Lys Lys Lys Ser Val Thr Val Leu Asp Val Gly Asp | 268 |
| HIVBH102 | ------------------------------------------------------------ | 280 |
| HIVBH5 | ------------------------------------------------------------ | 280 |
| HIVPV22 | ------------------------------------------------------------ | 280 |
| HIVBRU | ------------------------------------------------------------ | 280 |
| HIVMN | ------------------------------------------------------------ | 177 |
| HIVSF2 | ------------------------------------------------------------ | 268 |
| HIVRF | ------------------------------------------------------------ | 267 |
| HIVMAL | ------------------------------------------------------------ | 267 |
| HIVELI | ------------------------------------------------------------ | 267 |

| | | |
|---|---|---|
| HIVHXB2 | Ala Tyr Phe Ser Val Pro Leu Asp Glu Asp Phe Arg Lys Tyr Thr Ala Phe Thr Ile Pro | 288 |
| HIVBH102 | ------------------------------------------------------------ | 300 |
| HIVBH5 | ------------------------------------------------------------ | 300 |
| HIVPV22 | ------------------------------------------------------------ | 300 |
| HIVBRU | ------------------------------------------------------------ | 300 |
| HIVMN | ----------------------- Lys -------------------------------- | 197 |
| HIVSF2 | ----------------------- Lys -------------------------------- | 288 |
| HIVRF | ----------------------- Lys Glu ---------------------------- | 287 |
| HIVMAL | ------------------------------------------------------------ | 287 |
| HIVELI | ----------------------------------------------------- Ser -- | 287 |

| | | |
|---|---|---|
| HIVHXB2 | Ser Ile Asn Asn Glu Thr Pro Gly Ile Arg Tyr Gln Tyr Asn Val Leu Pro Gln Gly Trp | 308 |
| HIVBH102 | ------------------------------------------------------------ | 320 |
| HIVBH5 | ------------------------ Ser Gly --------------------------- | 320 |
| HIVPV22 | ------------------------------------------------------------ | 320 |
| HIVBRU | ------------------------------------------------------------ | 320 |
| HIVMN | ------------------------------------------------------------ | 217 |
| HIVSF2 | ------------------------------------------------------------ | 308 |
| HIVRF | --------------------- Arg ---------------------------------- | 307 |
| HIVMAL | ------------------------------------------------------------ | 307 |
| HIVELI | ------------------------------------------------------------ | 307 |

| | | |
|---|---|---|
| HIVHXB2 | Lys Gly Ser Pro Ala Ile Phe Gln Ser Ser Met Thr Lys Ile Leu Glu Pro Phe Arg Lys | 328 |
| HIVBH102 | ------------------------------------------------- Lys ------ | 340 |
| HIVBH5 | ------------------------------------------------------------ | 340 |
| HIVPV22 | ------------------------------------------------------------ | 340 |
| HIVBRU | ------------------------------------------------------------ | 340 |
| HIVMN | ------------------------------------------------------------ | 237 |
| HIVSF2 | ------------------------------------------------------------ | 328 |
| HIVRF | ------------------------------------------------- Lys ------ | 327 |
| HIVMAL | ---------------------------------------------------- Thr --- | 327 |
| HIVELI | ------------------------------------------------------------ | 327 |

TABLE 1-continued

HIV-1 pol protein sequence of HIVHXB2 virus
Data from Human Retroviruses and AIDS 1988 Los Alamos National Laboratory AcNPV-HIVWHpol

| HIVHXB2 | Gln Asn Pro Asp Ile Val Ile Tyr Gln Tyr Met Asp Asp Leu Tyr Val Gly Ser Asp Leu | 348 |
|---|---|---|
| HIVBH102 | ------------------------------------------------------------ | 360 |
| HIVBH5 | ------------------------------------------------------------ | 360 |
| HIVPV22 | ------------------------------------------------------------ | 360 |
| HIVBRU | ------------------------------------------------------------ | 360 |
| HIVMN | ------------------------------------------------------------ | 257 |
| HIVSF2 | ------------------------------------------------------------ | 348 |
| HIVRF | --------- Glu ----------------------------------------------- | 347 |
| HIVMAL | Lys ------ Glu ---------------------------------------------- | 347 |
| HIVELI | --------- Glu Met ------------------------------------------- | 347 |

| HIVHXB2 | Glu Ile Gly Gln His Arg Thr Lys Ile Glu Glu Leu Arg Gln His Leu Leu Arg Trp Gly | 368 |
|---|---|---|
| HIVBH102 | ------------------------------------------------------------ | 380 |
| HIVBH5 | ------------------------------------------------------------ | 380 |
| HIVPV22 | ------------------------------------------------------------ | 380 |
| HIVBRU | ------------------------------------------------------------ | 380 |
| HIVMN | ------------------ Ala ----------------- Arg ---------------- | 277 |
| HIVSF2 | ------------------------------------------------------------ | 368 |
| HIVRF | ------------------ Ile ----------------- Glu --------- Lys ----- | 367 |
| HIVMAL | --------------------------------------- Glu --------- Lys ----- | 367 |
| HIVELI | ---------------------------- Lys ------ Glu ----------------- | 367 |

| HIVHXB2 | Leu Thr Thr Pro Asp Lys Lys His Gln Lys Glu Pro Pro Phe Leu Trp Met Gly Tyr Glu | 388 |
|---|---|---|
| HIVBH102 | ------------------------------------------------------------ | 400 |
| HIVBH5 | Phe --------------------------------------------------------- | 400 |
| HIVPV22 | ------------------------------------------------------------ | 400 |
| HIVBRU | ------------------------------------------------------------ | 400 |
| HIVMN | Phe --------------------------------------------------------- | 297 |
| HIVSF2 | Phe --------------------------------------------------------- | 388 |
| HIVRF | Phe --------------------------------------------------------- | 387 |
| HIVMAL | Phe --------------------------------------------------------- | 387 |
| HIVELI | Phe --- Arg -------------------------------------------------- | 387 |

| HIVHXB2 | Leu His Pro Asp Lys Trp Thr Val Gln Pro Ile Val Leu Pro Glu Lys Asp Ser Trp Thr | 408 |
|---|---|---|
| HIVBH102 | ------------------------------------------------------------ | 420 |
| HIVBH5 | -------------------- Ile ------------------------------------ | 420 |
| HIVPV22 | ------------------------------------------------------------ | 420 |
| HIVBRU | ------------------------------------------------------------ | 420 |
| HIVMN | ------------------------------------------------------------ | 317 |
| HIVSF2 | --------------------------------- Met ----------------------- | 408 |
| HIVRF | ------------------------------------------------------------ | 407 |
| HIVMAL | ------------------------------ Gln ------ Asp --- Glu --------- | 407 |
| HIVELI | --------------------------- Ser --- Lys ------------ Glu --------- | 407 |

| HIVHXB2 | Val Asn Asp Ile Gln Lys Leu Val Gly Lys Leu Asn Trp Ala Ser Gln Ile Tyr Pro Gly | 428 |
|---|---|---|
| HIVBH102 | ------------------------------------------------------------ | 440 |
| HIVBH5 | ------------------------------------------------------------ | 440 |
| HIVPV22 | ------------------------------------------------------------ | 440 |
| HIVBRU | ------------------------------------------------------------ | 440 |
| HIVMN | -------------------------------------------------- Ala --- | 337 |
| HIVSF2 | -------------------------------------------------- Ala --- | 428 |
| HIVRF | -------------------------------------------------- Ala --- | 427 |
| HIVMAL | ------------------------------------------------------------ | 427 |
| HIVELI | --------------- Asn ------ Glu Arg --------------------------- | 427 |

| HIVHXB2 | Ile Lys Val Arg Gln Leu Cys Lys Leu Leu Arg Gly Thr Lys Ala Leu Thr Glu Val Ile | 448 |
|---|---|---|
| HIVBH102 | ------------------------------------------------------------ | 460 |
| HIVBH5 | ------------------------------------------------------------ | 460 |
| HIVPV22 | ------------------------------------------------------------ | 460 |
| HIVBRU | ------------------------------------------------------------ | 460 |
| HIVMN | --------- Lys ----------------------------------------------- | 357 |
| HIVSF2 | --------- Lys ----------------------------------------------- | 448 |
| HIVRF | --------- Lys --------------------------------------- Val | 447 |
| HIVMAL | --------- Lys ----------------------- Ala ------------ Asp Ile Val | 447 |
| HIVELI | ------------------------------------------------------------ | 447 |

TABLE 1-continued

HIV-1 pol protein sequence of HIVHXB2 virus
Data from Human Retroviruses and AIDS 1988 Los Alamos National Laboratory AcNPV-HIVWHpol

| | | |
|---|---|---|
| HIVHXB2 | Pro Leu Thr Glu Glu Ala Glu Leu Glu Leu Ala Glu Asn Arg Glu Ile Leu Lys Glu Pro | 468 |
| HIVBH102 | ---------------------------------------------------------- | 480 |
| HIVBH5 | ---------------------------------------------------------- | 480 |
| HIVPV22 | ---------------------------------------------------------- | 480 |
| HIVBRU | ---------------------------------------------------------- | 480 |
| HIVMN | ---------------------------------------------------------- | 377 |
| HIVSF2 | ---------------------------------------------------------- | 468 |
| HIVRF | Gln ------ Lys --------------------------------------------- | 467 |
| HIVMAL | --------- Ala ---------------------------------------------- | 467 |
| HIVELI | ---------------------------------------------------------- | 467 |
| | | |
| HIVHXB2 | Val His Gly Val Tyr Tyr Asp Pro Ser Lys Asp Leu Ile Ala Glu Ile Gln Lys Gln Gly | 488 |
| HIVBH102 | ---------------------------------------------------------- | 500 |
| HIVBH5 | ---------------------------------------------------------- | 500 |
| HIVPV22 | ---------------------------------------------------------- | 500 |
| HIVBRU | ---------------------------------------------------------- | 500 |
| HIVMN | ---------------------------------------- Val ------------ | 397 |
| HIVSF2 | ------ Glu ------------------------- Val ------------------ | 488 |
| HIVRF | ---------------------------------------------------------- | 487 |
| HIVMAL | ---------------------------------------------------------- | 487 |
| HIVELI | ---------------------------------------------------------- | 487 |
| | | |
| HIVHXB2 | Gln Gly Gln Trp Thr Tyr Gln Ile Tyr Gln Glu Pro Phe Lys Asn Leu Lys Thr Gly Lys | 508 |
| HIVBH102 | ---------------------------------------------------------- | 520 |
| HIVBH5 | ---------------------------------------------------------- | 520 |
| HIVPV22 | ---------------------------------------------------------- | 520 |
| HIVBRU | ---------------------------------------------------------- | 520 |
| HIVMN | ---------------------------------------------------------- | 417 |
| HIVSF2 | ---------------------------------------------------------- | 508 |
| HIVRF | ---------------------------------------------------------- | 507 |
| HIVMAL | -------------------------------- Gln Tyr ------------------ | 507 |
| HIVELI | His -------------------------------------------------------- | 507 |
| | | |
| HIVHXB2 | Tyr Ala Arg Met Arg Gly Ala His Thr Asn Asp Val Lys Gln Leu Thr Glu Ala Val Gln | 528 |
| HIVBH102 | ---------------------------------------------------------- | 540 |
| HIVBH5 | ---------------------------------------------------------- | 540 |
| HIVPV22 | ---------------------------------------------------------- | 540 |
| HIVBRU | --------- Thr ---------------------------------------------- | 540 |
| HIVMN | ---------------------------------------------------------- | 437 |
| HIVSF2 | ---------------------------------------------------------- | 528 |
| HIVRF | ---------------------------------------------------------- | 527 |
| HIVMAL | --------- Ile Lys Ser -------------------------------------- | 527 |
| HIVELI | -------------------------------------------- Ala ---------- | 527 |
| | | |
| HIVHXB2 | Lys Ile Thr Thr Glu Ser Ile Val Ile Trp Gly Lys Thr Pro Lys Phe Lys Leu Pro Ile | 548 |
| HIVBH102 | ---------------------------------------------------------- | 560 |
| HIVBH5 | ---------------------------------------------------------- | 560 |
| HIVPV22 | ---------------------------------------------------------- | 560 |
| HIVBRU | ---------------------------------------------------------- | 560 |
| HIVMN | ------ Ala ------------------------------------ Arg -------- | 457 |
| HIVSF2 | --- Val Ser ------------------------- Ile ------------------ | 548 |
| HIVRF | --- Val Ala ------------------------------------------------ | 547 |
| HIVMAL | ------ Ala Gln ---------------------------------- Arg -------- | 547 |
| HIVELI | Arg --- Ser -------------------------- Arg ----------- Arg -------- | 547 |
| | | |
| HIVHXB2 | Gln Lys Glu Thr Trp Glu Thr Trp Trp Thr Glu Tyr Trp Gln Ala Thr Trp Ile Pro Glu | 568 |
| HIVBH102 | ---------------------------------------------------------- | 580 |
| HIVBH5 | ---------------------------------------------------------- | 580 |
| HIVPV22 | ---------------------------------------------------------- | 580 |
| HIVBRU | ---------------------------------------------------------- | 580 |
| HIVMN | --------------------------------- Thr +++ ---------------- | 477 |
| HIVSF2 | ----------------- Ala ------ Met --------------------------- | 568 |
| HIVRF | ----------------- Ala -------------------------------------- | 567 |
| HIVMAL | ----------------- Ala -------------------------------------- | 567 |
| HIVELI | ------------------------- Ala ------------------------------ | 567 |

TABLE 1-continued

HIV-1 pol protein sequence of HIVHXB2 virus
Data from Human Retroviruses and AIDS 1988 Los Alamos National Laboratory AcNPV-HIVWHpol

| | | |
|---|---|---|
| HIVHXB2 | Trp Glu Phe Val Asn Thr Pro Pro Leu Val Lys Leu Trp Tyr Gln Leu Glu Lys Glu Pro | 588 |
| HIVBH102 | ------------------------------------------------------------ | 600 |
| HIVBH5 | ------------------------------------------------------------ | 600 |
| HIVPV22 | ------------------------------------------------------------ | 600 |
| HIVBRU | ------------------------------------------------------------ | 600 |
| HIVMN | ------Val------------------------------------------------- | 497 |
| HIVSF2 | ------------------------------------------------------------ | 588 |
| HIVRF | ------------------------------------------------------------ | 587 |
| HIVMAL | ----------------------------------------------Thr------ | 587 |
| HIVELI | ------------------------------------------------------------ | 587 |

| | | |
|---|---|---|
| HIVHXB2 | Ile Val Gly Ala Glu Thr Phe Tyr Val Asp Gly Ala Ala Asn Arg Glu Thr Lys Leu Gly | 608 |
| HIVBH102 | ------------------------------------------------------------ | 620 |
| HIVBH5 | --------------------------------Ser------------------ | 620 |
| HIVPV22 | ----------------------------------------------Arg------ | 620 |
| HIVBRU | --------------------------------Ser------------------ | 620 |
| HIVMN | ----------------------------------------------Lys--- | 517 |
| HIVSF2 | ------------------------------------------------------------ | 608 |
| HIVRF | ---Ile---------------------------------------------------- | 607 |
| HIVMAL | ----------------------------------------------Lys--- | 507 |
| HIVELI | ---Ile---------------------------------------------------- | 507 |

| | | |
|---|---|---|
| HIVHXB2 | Lys Ala Gly Tyr Val Thr Asn Arg Gly Arg Gln Lys Val Val Thr Leu Thr Asp Thr Thr | 628 |
| HIVBH102 | ----------------------Lys------------------Pro------Asn------ | 640 |
| HIVBH5 | ------------------------------------------------His------ | 640 |
| HIVPV22 | ------------Leu------Lys------------------Pro------Asn------ | 640 |
| HIVBRU | ------------------------------------------------------------ | 640 |
| HIVMN | ----------------------------------------Ser--------------- | 537 |
| HIVSF2 | ----------------------Asp---------------------Ser Ile Ala--------- | 628 |
| HIVRF | ----------------------Asp---------------------Ser--------------- | 627 |
| HIVMAL | ----------------------Asp---------------------Ser------Glu------ | 627 |
| HIVELI | ----------------------Asp---------------------Pro--------------- | 627 |

| | | |
|---|---|---|
| HIVHXB2 | Asn Gln Lys Thr Glu Leu Gln Ala Ile Tyr Leu Ala Leu Gln Asp Ser Gly Leu Glu Val | 648 |
| HIVBH102 | ------------------------------------------------------------ | 660 |
| HIVBH5 | --------------------------His------------------------------ | 660 |
| HIVPV22 | ------------------------------------------------------------ | 660 |
| HIVBRU | --------------------------His------------------------------ | 660 |
| HIVMN | --------------------------His------------------------------ | 557 |
| HIVSF2 | --------------------------His------------------------------ | 648 |
| HIVRF | --------------------------His------------------------------ | 647 |
| HIVMAL | --------------------------His--------------------Ser------ | 647 |
| HIVELI | --------------------------Asn------------------------------ | 647 |

| | | |
|---|---|---|
| HIVHXB2 | Asn Ile Val Thr Asp Ser Gln Tyr Ala Leu Gly Ile Ile Gln Ala Gln Pro Asp Gln Ser | 668 |
| HIVBH102 | ---------------------------------------------------Lys--- | 680 |
| HIVBH5 | ---------------------------------------------------Lys--- | 680 |
| HIVPV22 | ------------------------------------------------------------ | 680 |
| HIVBRU | ---------------------------------------------------Lys--- | 680 |
| HIVMN | ---------------------------------------------------Lys--- | 577 |
| HIVSF2 | ---------------------------------------------------Lys--- | 668 |
| HIVRF | ---------------------------------------------------Lys--- | 667 |
| HIVMAL | ---------------------------------------------------Lys--- | 667 |
| HIVELI | ---------------------------------------------------Lys--- | 667 |

| | | |
|---|---|---|
| HIVHXB2 | Glu Ser Glu Leu Val Asn Gln Ile Ile Glu Gln Leu Ile Lys Lys Glu Lys Val Tyr Leu | 688 |
| HIVBH102 | ------------------------------------------------------------ | 700 |
| HIVBH5 | ------------------------------------------------------------ | 700 |
| HIVPV22 | ---------------------------------------------Gln------------ | 700 |
| HIVBRU | ------------------------------------------------------------ | 700 |
| HIVMN | ---------------Ser---------------------------------------- | 597 |
| HIVSF2 | ---------------Ser---------------------------------------- | 688 |
| HIVRF | ---------------Ser---------------------------------------- | 687 |
| HIVMAL | ---------Ile------------------------Gln---Asp------------ | 687 |
| HIVELI | ------------------------------------------------------------ | 687 |

TABLE 1-continued

HIV-1 pol protein sequence of HIVHXB2 virus
Data from Human Retroviruses and AIDS 1988 Los Alamos National Laboratory AcNPV-HIVWHpol

| | | |
|---|---|---|
| HIVHXB2 | Ala Trp Val Pro Ala His Lys Gly Ile Gly Gly Asn Glu Gln Val Asp Lys Leu Val Ser | 708 |
| HIVBH102 | ------------------------------------------------------------ | 720 |
| HIVBH5 | ------------------------------------------------------------ | 720 |
| HIVPV22 | ------------------------------------------------------------ | 720 |
| HIVBRU | ------------------------------------------------------------ | 720 |
| HIVMN | ------------------------------------------------------------ | 617 |
| HIVSF2 | ------------------------------------------------------------ | 708 |
| HIVRF | ---------------------------------------------- Arg --------- | 707 |
| HIVMAL | Ser ---------------------------------------------------------- | 707 |
| HIVELI | ------------------------------------------------------------ | 707 |

| | | |
|---|---|---|
| HIVHXB2 | Ala Gly Ile Arg Lys Val Leu Phe Leu Asp Gly Ile Asp Lys Ala Gln Asp Glu His Glu | 728 |
| HIVBH102 | --------------- Ile ----------------------------------------- | 740 |
| HIVBH5 | --------------- Ile ---------------------------- Glu --------- | 740 |
| HIVPV22 | --------------- Ile ----------------------------------------- | 740 |
| HIVBRU | ------------------------------------------------------------ | 740 |
| HIVMN | ------------------------------------------------- Glu Asp ------ | 637 |
| HIVSF2 | ------------------------- Asn ------------------ Glu --------- | 728 |
| HIVRF | Thr ---------------------------------------------------------- | 727 |
| HIVMAL | Ser ---------------------------------------- Glu --------- | 727 |
| HIVELI | Gln ---------------------------------------- Glu --------- | 727 |

| | | |
|---|---|---|
| HIVHXB2 | Lys Tyr His Ser Asn Trp Arg Ala Met Ala Ser Asp Phe Asn Leu Pro Pro Val Val Ala | 748 |
| HIVBH102 | ------------------------------------------------------------ | 760 |
| HIVBH5 | ------------------------------------------------------------ | 760 |
| HIVPV22 | ------------------------------------------------------------ | 760 |
| HIVBRU | ------------------------------------------------------------ | 760 |
| HIVMN | ------------------------------------------------ Ile ------ | 657 |
| HIVSF2 | ------------------------------------------------------------ | 748 |
| HIVRF | ------------------------------------------------------------ | 747 |
| HIVMAL | ------------------------------------------------ Ile ------ | 747 |
| HIVELI | --------- Asn ------------------------------------------------ | 747 |

| | | |
|---|---|---|
| HIVHXB2 | Lys Glu Ile Val Ala Ser Cys Asp Lys Cys Gln Leu Lys Gly Glu Ala Met His Gly Gln | 768 |
| HIVBH102 | ------------------------------------------------------------ | 780 |
| HIVBH5 | ------------------------------------------------------------ | 780 |
| HIVPV22 | ------------------------------------------------------------ | 780 |
| HIVBRU | ------------------------------------------------------------ | 780 |
| HIVMN | ------------------------------------------------------------ | 677 |
| HIVSF2 | ------------------------------------------------------------ | 768 |
| HIVRF | ------------------------------------------------------------ | 767 |
| HIVMAL | ------------------------------------------------------------ | 767 |
| HIVELI | ------------------------------------------------------------ | 767 |

| | | |
|---|---|---|
| HIVHXB2 | Val Asp Cys Ser Pro Gly Ile Trp Gln Leu Asp Cys Thr His Leu Glu Gly Lys Val Ile | 788 |
| HIVBH102 | ------------------------------------------------------------ | 800 |
| HIVBH5 | ------------------------------------------------------------ | 800 |
| HIVPV22 | ------------------------------------------------------------ | 800 |
| HIVBRU | ------------------------------------------------------------ | 800 |
| HIVMN | ------------------------------------------------------------ | 697 |
| HIVSF2 | -------------------------------------------------- Ile --- | 788 |
| HIVRF | -------------------------------------------------- Ile --- | 787 |
| HIVMAL | -------------------------------------------------- Ile --- | 787 |
| HIVELI | ------------------------------------------------------------ | 787 |

| | | |
|---|---|---|
| HIVHXB2 | Leu Val Ala Val His Val Ala Ser Gly Tyr Ile Glu Ala Glu Val Ile Pro Ala Glu Thr | 808 |
| HIVBH102 | ------------------------------------------------------------ | 820 |
| HIVBH5 | ------------------------------------------------------------ | 820 |
| HIVPV22 | ------------------------------------------------------------ | 820 |
| HIVBRU | ------------------------------------------------------------ | 820 |
| HIVMN | ------------------------------------------------------------ | 717 |
| HIVSF2 | ------------------------------------------------------------ | 808 |
| HIVRF | ------------------------------------------------------------ | 807 |
| HIVMAL | Ile ---------------------------------------------------------- | 807 |
| HIVELI | ------------------------------------------------------------ | 807 |

TABLE 1-continued

HIV-1 pol protein sequence of HIVHXB2 virus
Data from Human Retroviruses and AIDS 1988 Los Alamos National Laboratory AcNPV-HIVWHpol

| | | |
|---|---|---|
| HIVHXB2 | Gly Gln Glu Thr Ala Tyr Phe Leu Leu Lys Leu Ala Gly Arg Trp Pro Val Lys Thr Ile | 828 |
| HIVBH102 | ---------------------------------------------------------------- | 840 |
| HIVBH5 | ---------------------------------------------------------------- | 840 |
| HIVPV22 | ---------------------------------------------------------------- | 840 |
| HIVBRU | ---------------------------------------------------------------- | 840 |
| HIVMN | ---------------------------------------------------------------- | 737 |
| HIVSF2 | ---------------------------------------------------------------- | 828 |
| HIVRF | -------------------- Ile ---------------------------- Val --- | 827 |
| HIVMAL | -------------------- Ile ---------------------------- Val Val | 827 |
| HIVELI | ---------------------------------------------------- Val Val | 827 |

| | | |
|---|---|---|
| HIVHXB2 | His Thr Asp Asn Gly Ser Asn Phe Thr Gly Ala Thr Val Arg Ala Ala Cys Trp Trp Ala | 848 |
| HIVBH102 | -------------------------- Ser --------- Lys ------------------ | 860 |
| HIVBH5 | -------------------------- Ser --------- Lys ------------------ | 860 |
| HIVPV22 | -------------------------- Ser --------- Lys ------------------ | 860 |
| HIVBRU | -------------------------- Ser Thr ------ Lys ------------------ | 860 |
| HIVMN | --------------- Pro --------- Ser Thr ------ Lys --------------- Thr | 757 |
| HIVSF2 | -------------------------- Ser Thr ------ Lys ------------------ | 848 |
| HIVRF | -------------------------- Ser Thr ------ Lys ------------------ | 847 |
| HIVMAL | -------------------------- Ser --- Ala --- Lys ------------------ | 847 |
| HIVELI | -------------------------- Ser --- Ala --- Lys ------------------ | 847 |

| | | |
|---|---|---|
| HIVHXB2 | Gly Ile Lys Gln Glu Phe Gly Ile Pro Tyr Asn Pro Gln Ser Gln Gly Val Val Glu Ser | 868 |
| HIVBH102 | ---------------------------------------------------------------- | 880 |
| HIVBH5 | ---------------------------------------------------------------- | 880 |
| HIVPV22 | ---------------------------------------------------------------- | 880 |
| HIVBRU | ---------------------------------------------------------------- | 880 |
| HIVMN | ---------------------------------------------------- Ile ------ | 777 |
| HIVSF2 | ---------------------------------------------------------------- | 868 |
| HIVRF | ---------------------------------------------------------------- | 867 |
| HIVMAL | Asn ------------------------------------------------------------- | 867 |
| HIVELI | ---------------------------------------------------------------- | 867 |

| | | |
|---|---|---|
| HIVHXB2 | Met Asn Lys Glu Leu Lys Lys Ile Ile Gly Gln Val Arg Asp Gln Ala Glu His Leu Lys | 888 |
| HIVBH102 | ---------------------------------------------------------------- | 900 |
| HIVBH5 | ---------------------------------------------------------------- | 900 |
| HIVPV22 | ---------------------------------------------------------------- | 900 |
| HIVBRU | ---------------------------------------------------------------- | 900 |
| HIVMN | ---------------------------------------------------------------- | 797 |
| HIVSF2 | ------ Asn ----------------------------------------------------- | 888 |
| HIVRF | --------- Gln ------ Gln --------------------------------------- | 887 |
| HIVMAL | ------------------------------------------- Glu ---------------- | 887 |
| HIVELI | ---------------------------------------------------------------- | 887 |

| | | |
|---|---|---|
| HIVHXB2 | Thr Ala Val Gln Met Ala Val Phe Ile His Asn Phe Lys Arg Lys Gly Gly Ile Gly Gly | 908 |
| HIVBH102 | ---------------------------------------------------------------- | 920 |
| HIVBH5 | ---------------------------------------------------------------- | 920 |
| HIVPV22 | ---------------------------------------------------------------- | 920 |
| HIVBRU | ---------------------------------------------------------------- | 920 |
| HIVMN | Arg ------------------------------------------------------------- | 817 |
| HIVSF2 | ---------------------------------------------------------------- | 908 |
| HIVRF | ---------------------------------------------------------------- | 907 |
| HIVMAL | ---------------------------------------------------------------- | 907 |
| HIVELI | ----------------------------------------- Arg Arg ------------- | 907 |

| | | |
|---|---|---|
| HIVHXB2 | Tyr Ser Ala Gly Glu Arg Ile Val Asp Ile Ile Ala Thr Asp Ile Gln Thr Lys Glu Leu | 928 |
| HIVBH102 | ---------------------------------------------------------------- | 940 |
| HIVBH5 | ---------------------------------------------------------------- | 940 |
| HIVPV22 | ---------------------------------------------------------------- | 940 |
| HIVBRU | ---------------------------------------------------------------- | 940 |
| HIVMN | ---------------------- Gly ------------------------------------- | 837 |
| HIVSF2 | ---------------------------------------------------------------- | 928 |
| HIVRF | ---------------------------------------------------------------- | 927 |
| HIVMAL | ---------------------- Ile --- Met ----------------------------- | 927 |
| HIVELI | ---------------------- Ile ------------------------------------- | 927 |

TABLE 1-continued

HIV-1 pol protein sequence of HIVHXB2 virus
Data from Human Retroviruses and AIDS 1988 Los Alamos National Laboratory AcNPV-HIVWHpol

| | | |
|---|---|---|
| HIVHXB2 | Gln Lys Gln Ile  Thr Lys Ile   Gln Asn Phe Arg Val Tyr Tyr Arg Asp Ser  Arg Asn Ser | 948 |
| HIVBH102 | ------------------------------------------------------------- Pro | 960 |
| HIVBH5 | ------------------------------------------------------------- Pro | 960 |
| HIVPV22 | ------------------------------------------------------------- Pro | 960 |
| HIVBRU | --------------------------------------------------------- Asp Pro | 960 |
| HIVMN | --------------------------------------------------------- Asp Pro | 857 |
| HIVSF2 | ----------------------------------------------- Asn Lys Asp Pro | 948 |
| HIVRF | --------------------------------------------------------- Asp Pro | 947 |
| HIVMAL | ----------------------------------------------- Asn - - - Asp Pro | 947 |
| HIVELI | ------------ Ile ---------------------------------------- Asp Pro | 947 |
| | | |
| HIVHXB2 | Leu Trp Lys Gly Pro Ala Lys Leu Leu Trp Lys Gly Glu Gly Ala Val Val Ile  Gln Asp | 968 |
| HIVBH102 | ---------------------------------------------------------------- | 980 |
| HIVBH5 | ---------------------------------------------------------------- | 980 |
| HIVPV22 | ---------------------------------------------------------------- | 980 |
| HIVBRU | ---------------------------------------------------------------- | 980 |
| HIVMN | ---------------------------------------------------------------- | 877 |
| HIVSF2 | ---------------------------------------------------------------- | 968 |
| HIVRF | ------------- His ---------------------------------------------- | 967 |
| HIVMAL | Ile -------------------------------------------------------------- | 967 |
| HIVELI | Ile -------------------------------------------------------------- | 967 | sor cds start - >

| | | |
|---|---|---|
| HIVHXB2 | Asn Ser Asp Ile  Lys Val Val Pro Arg Arg Lys Ala Lys Ile  Ile  Arg Asp Tyr Gly Lys | 988 |
| HIVBH102 | ---------------------------------------------------------------- | 1000 |
| HIVBH5 | ---------------------------------------------------------------- | 1000 |
| HIVPV22 | ---------------------------------------------------------------- | 1000 |
| HIVBRU | ---------------------------------------------------------------- | 1000 |
| HIVMN | --- Asn -------------------------------- Val -------------------- | 897 |
| HIVSF2 | ---------------------------------------------------------------- | 988 |
| HIVRF | ---------------------------------------------------------------- | 987 |
| HIVMAL | ---------------------------------------------------------------- | 987 |
| HIVELI | Lys ---------------------------- Val ---------------------- | 987 |
| | | |
| HIVHXB2 | Gln Met Ala Gly Asp Asp Cys Val Ala Ser  Arg Gln Asp Glu Asp +++ | 1004 |
| HIVBH102 | -------------------------------------------------- | 1016 |
| HIVBH5 | -------------------------------------------------- | 1016 |
| HIVPV22 | -------------------------------------------------- | 1016 |
| HIVBRU | -------------------------------------------------- | 1016 |
| HIVMN | --- Thr ------------------------------------------ | 913 |
| HIVSF2 | -------------------------------------------------- | 1004 |
| HIVRF | -------------------------------------------------- | 1003 |
| HIVMAL | ------------------------- Gly Gly ---------------- | 1003 |
| HIVELI | -------------------------------------------------- | 1003 |

TABLE 2

HIV-1 pol gene HIVHXB2 Sequence
Data from Human Retroviruses and AIDS, 1988
Los Alamos National Laboratory AcNPV-HIVWHpol Virus

```
                                    RBS
                          Bam HI          ti
                      5'-GGATCCTATAAATATG    tttttta    gggaagatct pol cds start (NH2-terminus uncertain) ->

2101  ggccttccta   caagggaagg   ccagggaatt   ttcttcagag   cagaccagag   ccaacagccc 2161  caccagaaga   gagcttcagg   tctggggtag   agacaacaac   tccccctcag   aagcaggagc 2221  cgatagacaa   ggaactgtat   cctttaactt   ccctcaggtc   actctttggc   aacgacccct 2281  cgtcacaaTA   Aagatagggg   ggcaactaaa   ggaagctcta   ttagatacag   gagcagatga
                <- gag cds end
```

TABLE 2-continued

| | | | | | |
|---|---|---|---|---|---|
| 2341 | tacagtatta | gaagaaatga | gtttgccagg | aagatggaaa | ccaaaaatga | tagggggaat |
| 2401 | tggaggtttt | atcaaagtaa | gacagtatga | tcagatactc | atagaaatct | gtggacataa |
| 2461 | agctataggt | acagtattag | taggacctac | acctgtcaac | ataattggaa | gaaatctgtt |
| 2521 | gactcagatt | ggttgcactt | taaattttcc | cattagccct | attgagactg | taccagtaaa |
| 2581 | attaaagcca | ggaatggatg | gcccaaaagt | taaacaatgg | ccattgacag | aagaaaaat |
| 2641 | aaaagcatta | gtagaaattt | gtacagagat | ggaaaaggaa | gggaaaattt | caaaaattgg |
| 2701 | gcctgaaaat | ccatacaata | ctccagtatt | tgccataaag | aaaaagaca | gtactaaatg |
| 2761 | gagaaaatta | gtagatttca | gagaacttaa | taagagaact | caagacttct | gggaagttca |
| 2821 | attaggaata | ccacatcccg | cagggttaaa | aaagaaaaaa | tcagtaacag | tactggatgt |
| 2881 | gggtgatgca | tattttcag | ttcccttaga | tgaagacttc | aggaagtata | ctgcatttac |
| 2941 | catacctagt | ataaacaatg | agacaccagg | gattagatat | cagtacaatg | tgcttccaca |
| 3001 | gggatggaaa | ggatcaccag | caatattcca | aagtagcatg | acaaaaatct | tagagccttt |
| 3061 | tagaaaacaa | aatccagaca | tagttatcta | tcaatacatg | gatgatttgt | atgtaggatc |
| 3121 | tgacttagaa | atagggcagc | atagaacaaa | aatagaggag | ctgagacaac | atctgttgag |
| 3181 | gtggggactt | accacaccag | acaaaaaaca | tcagaaagaa | cctccattcc | tttggatggg |
| 3241 | ttatgaactc | catcctgata | aatggacagt | acagcctata | gtgctgccag | aaaaagacag |
| 3301 | ctggactgtc | aatgacatac | agaagttagt | ggggacattg | aattgggcaa | gtcagattta |
| 3361 | cccagggatt | aaagtaaggc | aattatgtaa | actccttaga | ggaaccaaag | cactaacaga |
| 3421 | agtaatacca | ctaacagaag | aagcagagct | agaactggca | gaaaacagag | agattctaaa |
| 3481 | agaaccagta | catggagtgt | attatgaccc | atcaaaagac | ttaatagcag | aaatacagaa |
| 3541 | gcaggggcaa | ggccaatgga | catatcaaat | ttatcaagag | ccatttaaaa | atctgaaaac |
| 3601 | aggaaaatat | gcaagaatga | ggggtgccca | cactaatgat | gtaaaacaat | taacagaggc |
| 3661 | agtgcaaaaa | ataaccacag | aaagcatagt | aatatgggga | aagactccta | aatttaaact |
| 3721 | gcccatacaa | aaggaaacat | gggaaacatg | gtggacagag | tattggcaag | ccacctggat |
| 3781 | tcctgagtgg | gagtttgtta | atacccctcc | cttagtgaaa | ttatggtacc | agttagagaa |
| 3841 | agaacccata | gtaggagcag | aaaccttcta | tgtagatggg | gcagctaaca | gggagactaa |
| 3901 | attaggaaaa | gcaggatatg | ttactaatag | aggaagacaa | aaagttgtca | ccctaactga |
| 3961 | cacaacaaat | cagaagactg | agttacaagc | catttatcta | gctttgcagg | attcgggatt |

TABLE 2-continued

| | | | | | |
|---|---|---|---|---|---|
| 4021 | agaagtaaac | atagtaacag | actcacaata | tgcattagga | atcattcaag | cacaaccaga |
| 4081 | tcaaagtgaa | tcagagttag | tcaatcaaat | aatagagcag | ttaataaaaa | aggaaaaggt |
| 4141 | ctatctggca | tgggtaccag | cacacaaagg | aattggagga | aatgaacaag | tagataaatt |
| 4201 | agtcagtgct | ggaatcagga | aagtactatt | tttagatgga | atagataagg | cccaagatga |
| 4261 | acatgagaaa | tatcacagta | attggagagc | aatggctagt | gattttaacc | tgccacctgt |
| 4321 | agtagcaaaa | gaaatagtag | ccagctgtga | taaatgtcag | ctaaaaggag | aagccatgca |
| 4381 | tggacaagta | gactgtagtc | caggaatatg | gcaactagat | tgtacacatt | tagaaggaaa |
| 4441 | agttatcctg | gtagcagttc | atgtagccag | tggatatata | gaagcagaag | ttattccagc |
| 4501 | agaaacaggg | caggaaacag | catattttct | tttaaaatta | gcaggaagat | ggccagtaaa |
| 4561 | aacaatacat | actgacaatg | gcagcaattt | caccggtgct | acggttaggg | ccgcctgttg |
| 4621 | gtgggcggga | atcaagcagg | aatttggaat | tccctacaat | ccccaaagtc | aaggagtagt |
| 4681 | agaatctatg | aataaagaat | taagaaaat | tataggacag | gtaagagatc | aggctgaaca |
| 4741 | tcttaagaca | gcagtacaaa | tggcagtatt | catccacaat | tttaaaagaa | aaggggggat |
| 4801 | tggggggtac | agtgcagggg | aaagaatagt | agacataata | gcaacagaca | tacaaactaa |
| 4861 | agaattacaa | aaacaatta | caaaaattca | aaattttcgg | gtttattacA | Gggacagcag 3'sj |
| 4921 | aaattcactt | tggaaaggac | cagcaaagct | cctctggaaa 5'sj | gGTgaagggg | cagtagtaat |
| 4981 | acaagataat | agtgacataa | aagtagtgcc | aagaagaaaa | gcaaagatca sor 23 kD cds start —> | ttagggattA |
| 5041 | TGgaaaacag | atggcaggtg | atgattgtgt | ggcaagtaga | caggatgagg  Crossover linker sequence | Bam HI atTAGGATCC-3' <— pol end |

TABLE 3

HIV-1 pol gene
HIVHXB2 Sequence
Data from Human Retroviruses and AIDS, 1988
Los Alamos National Laboratory AcNPV-HIVWHpol Virus

```
                                RBS
                   Bam HI        _____ti(AcNPV-HIVWHpol start)
                   5'-GGATCCTATAAATATG   tttttta   gggaagatct pol cds start (NH2-terminus uncertain) —>
```

| | | | | | |
|---|---|---|---|---|---|
| 2101 | ggccttccta | caagggaagg | ccagggaatt | ttcttcagag | cagaccagag | ccaacagccc |
| 2161 | caccagaaga | gagcttcagg | tctggggtag | agacaacaac | tccccctcag | aagcaggagc |

TABLE 3-continued

| 2221 | cgatagacaa | ggaactgtat | cctttaactt | ccctcaggtc | actctttggc | aacgacccct |
| --- | --- | --- | --- | --- | --- | --- |
| 2281 | cgtcacaaTA | Aagatagggg | ggcaactaaa | ggaagctcta | ttagatacag | gagcagatga |

AcNPV-HIVYKpol Virus     Bam HI     RBS     ti
5'-GGATCCTATAAATATG (ti;AcNPV-HIVYKpol start)

| 2341 | tacagtatta | gaagaaatga | gtttgccagg | aagatggaaa | ccaaaaatga | taggggaat |
| --- | --- | --- | --- | --- | --- | --- |
| 2401 | tggaggtttt | atcaaagtaa | gacagtatga | tcagatactc | atagaaatct | gtggacataa |
| 2461 | agctataggt | acagtattag | taggacctac | acctgtcaac | ataattggaa | gaaatctgtt |
| 2521 | gactcagatt | ggttgcactt | taaattttcc | cattagccct | attgagactg | taccagtaaa |
| 2581 | attaaagcca | ggaatggatg | gcccaaaagt | taaacaatgg | ccattgacag | aagaaaaaat |
| 2641 | aaaagcatta | gtagaaattt | gtacagagat | ggaaaaggaa | gggaaaattt | caaaaattgg |
| 2701 | gcctgaaaat | ccatacaata | ctccagtatt | tgccataaag | aaaaagaca | gtactaaatg |
| 2761 | gagaaaatta | gtagatttca | gagaacttaa | taagagaact | caagacttct | gggaagttca |
| 2821 | attaggaata | ccacatcccg | cagggttaaa | aaagaaaaaa | tcagtaacag | tactggatgt |
| 2881 | gggtgatgca | tatttttcag | ttcccttaga | tgaagacttc | aggaagtata | ctgcatttac |
| 2941 | catacctagt | ataaacaatg | agacaccagg | gattagatat | cagtacaatg | tgcttccaca |
| 3001 | gggatggaaa | ggatcaccag | caatattcca | aagtagcatg | acaaaaatct | tagagccttt |
| 3061 | tagaaaacaa | aatccagaca | tagttatcta | tcaatacatg | gatgatttgt | atgtaggatc |
| 3121 | tgacttagaa | atagggcagc | atagaacaaa | aatagaggag | ctgagacaac | atctgttgag |
| 3181 | gtggggactt | accacaccag | acaaaaaaca | tcagaaagaa | cctccattcc | tttggatggg |
| 3241 | ttatgaactc | catcctgata | aatggacagt | acagcctata | gtgctgccag | aaaaagacag |
| 3301 | ctggactgtc | aatgacatac | agaagttagt | ggggaaattg | aattgggcaa | gtcagattta |
| 3361 | cccagggatt | aaagtaaggc | aattatgtaa | actccttaga | ggaaccaaag | cactaacaga |
| 3421 | agtaatacca | ctaacagaag | aagcagagct | agaactggca | gaaaacagag | agattctaaa |
| 3481 | agaaccagta | catggagtgt | attatgaccc | atcaaaagac | ttaatagcag | aaatacagaa |
| 3541 | gcaggggcaa | ggccaatgga | catatcaaat | ttatcaagag | ccatttaaaa | atctgaaaac |
| 3601 | aggaaaatat | gcaagaatga | ggggtgccca | cactaatgat | gtaaaacaat | taacagaggc |
| 3661 | agtgcaaaaa | ataaccacag | aaagcatagt | aatatgggga | aagactccta | aatttaaact |
| 3721 | gcccatacaa | aaggaaacat | gggaaacatg | gtggacagag | tattggcaag | ccacctggat |
| 3781 | tcctgagtgg | gagtttgtta | atacccctcc | cttagtgaaa | ttatggtacc | agttagagaa |

TABLE 3-continued

| | | | | | |
|---|---|---|---|---|---|
| 3841 | agaacccata | gtaggagcag | aaaccttcta | tgtagatggg | gcagctaaca | gggagactaa |
| 3901 | attaggaaaa | gcaggatatg | ttactaatag | aggaagacaa | aaagttgtca | ccctaactga |
| 3961 | cacaacaaat | cagaagactg | agttacaagc | aatttatcta | gctttgcagg | attcgggatt |
| 4021 | agaagtaaac | atagtaacag | actcacaata | tgcattagga | atcattcaag | cacaaccaga |
| 4081 | tcaaagtgaa | tcagagttag | tcaatcaaat | aatagagcag | ttaataaaaa | aggaaaaggt |
| 4141 | ctatctggca | tgggtaccag | cacacaaagg | aattggagga | aatgaacaag | tagataaatt |
| 4201 | agtcagtgct | ggaatcagga | aagtactatt | tttagatgga | atagataagg | cccaagatga |
| 4261 | acatgagaaa | tatcacagta | attggagagc | aatggctagt | gattttaacc | tgccacctgt |
| 4321 | agtagcaaaa | gaaatagtag | ccagctgtga | taaatgtcag | ctaaaggag | aagccatgca |
| 4381 | tggacaagta | gactgtagtc | caggaatatg | gcaactagat | tgtacacatt | tagaaggaaa |
| 4441 | agttatcctg | gtagcagttc | atgtagccag | tggatatata | gaagcagaag | ttattccagc |
| 4501 | agaaacaggg | caggaaacag | catatttcct | tttaaaatta | gcaggaagat | ggccagtaaa |
| 4561 | aacaatacat | actgacaatg | gcagcaattt | caccggtgct | acggttaggg | ccgcctgttg |
| 4621 | gtgggcggga | atcaagcagg | aatttggaat | tccctacaat | ccccaaagtc | aaggagtagt |
| 4681 | agaatctatg | aataaagaat | taagaaaat | tataggacag | gtaagagatc | aggctgaaca |
| 4741 | tcttaagaca | gcagtacaaa | tggcagtatt | catccacaat | tttaaaagaa | aagggggat |
| 4801 | tgggggtac | agtgcagggg | aaagaatagt | agacataata | gcaacagaca | tacaaactaa |
| 4861 | agaattacaa | aaacaaatta | caaaaattca | aaattttcgg | gtttattacA | Ggacagcag<br>/\ 3'sj |
| 4921 | aaattcactt | tggaaaggac | cagcaaagct | cctctggaaa | gGTgaagggg<br>/\ 5'sj | cagtagtaat |
| 4981 | acaagataat | agtgacataa | aagtagtgcc | aagaagaaaa | gcaaagatca | ttagggattA<br><u>Bam HI</u> |
| 5041 | TGgaaaacag | atggcaggtg | atgattgtgt | ggcaagtaga | caggatgagg | atTAGGATCC<br><u>Sph I</u><br>GCATG-3'<br><-- pol end |
| 5101 | ggaaaagttt | agtaaaacac | catatgtatg | tttcagggaa | agctagggga | tggttttata |
| 5161 | gacatcacta | tgaaagccct | catccaagaa | taagttcaga | agtacacatc | ccactagggg |
| 5221 | atgctagatt | ggtaataaca | acatattggg | gtctgcatac | aggagaaaga | gactggcatt |
| 5281 | tgggtcaggg | agtctccata | gaatggagga | aaaagagata | tagcacacaa | gtagaccctg |
| 5341 | aactagcaga | ccaactaatt | catctgtatt | actttgactg | ttttcAGac<br>/\ 3'sj | tctgctataa |

TABLE 3-continued

| | | | | | | |
|---|---|---|---|---|---|---|
| 5401 | gaaaggcctt | attaggacac | atagttagcc | ctaggtgtga | atatcaagca | ggacataaca |
| 5461 5'sj | agGTaggatc /\ | tctacaatac | ttggcactag | cagcattaat | aacaccaaaa | aagataaagc |
| 5521 | cacctttgcc | tagtgttacg | aaactgacag R orf cds start –> | aggatagATG | gaacaagccc | cagaagacca |
| 5581 | agggccacag | agggagccac | acaatgaatg | gacacTAGag <– sor 23 kD cds end | cttttagagg | agcttaagaa |
| 5641 | tgaagctgtt | agacattttc | ctaggatttg | gctccatggc | ttagggcaac | atatctatga |
| 5701 | aacttatggg | gatacttggg | caggagtgga | agccataata | agaattctgc | aacaactgct |
| 5761 | gtttatccat | tttcAGaatt /\ 3'sj | gggtgtcgac | aTAGcagaat <– R orf cds end | aggcgttact | cgacagagga |
| 5821 tat cds start –> | gagcaagaaA | TGgagccagt | agatcctaga | ctagagccct | ggaagcatcc | aggaagtcag |
| 5881 | cctaaaactg | cttgtaccaa | ttgctattgt | aaaaagtgtt | gctttcattg | ccaagtttgt |
| 5941 | ttcataacaa | aagccttagg trs/art cds start –> | catctcctAT | GgcAGgaaga /\ 3'sj | agcggagaca | gcgacgaaga |
| 6001 | gctcatcaga | acagtcagac (tat, trs/art, 27 kD) | tcatcaagct | tctctatcaa 5'sj | agcaGTaagt /\ | agtacatgta |
| 6061 U orf –> | AcGcaaccta | taccaatagt | agcaatagta | gcattagtag | tagcaataat | aatagcaata |
| 6121 | gttgtgtggt | ccatagtaat | catagaatat | aggaaaatat | taagacaaag | aaaaatagac |

---

I claim:

1. A method of testing for exposure of an organism to HIV, which comprises providing an HIV antigen, contacting said antigen with a sample from said organism and detecting any antigen-antibody complexes created as a result of said contact as indicative of exposure of said organism to HIV, said antigen being a polypeptide having the amino acid sequence of SEQ ID NO:22.

2. A diagnostic kit for detecting antibodies to HIV antigens wherein said kit contains, as a test reagent, a polypeptide having the amino acid sequence of SEQ ID NO:22.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
  ( A ) LENGTH: 1005 amino acids
  ( B ) TYPE: amino acid
  ( C ) STRANDEDNESS: Not Relevant
  ( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
  ( A ) ORGANISM: Human immunodeficiency virus type 1
  ( B ) STRAIN: HXB2

( x i ) SEQUENCE DESCRIPTION: SEQ ID NO:1:

```
Met  Phe  Phe  Arg  Glu  Asp  Leu  Ala  Phe  Leu  Gln  Gly  Lys  Ala  Arg  Glu
 1                  5                       10                      15
Phe  Ser  Ser  Glu  Gln  Thr  Arg  Ala  Asn  Ser  Pro  Thr  Arg  Arg  Glu  Leu
            20                      25                      30
```

-continued

```
         Gln  Val  Trp  Gly  Arg  Asp  Asn  Asn  Ser  Pro  Ser  Glu  Ala  Gly  Ala  Asp
                    35                  40                  45

Arg  Gln  Gly  Thr  Val  Ser  Phe  Asn  Phe  Pro  Gln  Val  Thr  Leu  Trp  Gln
              50                  55                  60

Arg  Pro  Leu  Val  Thr  Ile  Lys  Ile  Gly  Gly  Gln  Leu  Lys  Glu  Ala  Leu
         65                  70                  75                                  80

Leu  Asp  Thr  Gly  Ala  Asp  Asp  Thr  Val  Leu  Glu  Glu  Met  Ser  Leu  Pro
                             85                  90                       95

Gly  Arg  Trp  Lys  Pro  Lys  Met  Ile  Gly  Gly  Ile  Gly  Gly  Phe  Ile  Lys
                        100                 105                      110

Val  Arg  Gln  Tyr  Asp  Gln  Ile  Leu  Ile  Glu  Ile  Cys  Gly  His  Lys  Ala
                   115                 120                 125

Ile  Gly  Thr  Val  Leu  Val  Gly  Pro  Thr  Pro  Val  Asn  Ile  Ile  Gly  Arg
              130                 135                      140

Asn  Leu  Leu  Thr  Gln  Ile  Gly  Cys  Thr  Leu  Asn  Phe  Pro  Ile  Ser  Pro
         145                      150                 155                      160

Ile  Glu  Thr  Val  Pro  Val  Lys  Leu  Lys  Pro  Gly  Met  Asp  Gly  Pro  Lys
                             165                      170                      175

Val  Lys  Gln  Trp  Pro  Leu  Thr  Glu  Glu  Lys  Ile  Lys  Ala  Leu  Val  Glu
                        180                 185                      190

Ile  Cys  Thr  Glu  Met  Glu  Lys  Glu  Gly  Lys  Ile  Ser  Lys  Ile  Gly  Pro
                   195                 200                 205

Glu  Asn  Pro  Tyr  Asn  Thr  Pro  Val  Phe  Ala  Ile  Lys  Lys  Lys  Asp  Ser
              210                 215                      220

Thr  Lys  Trp  Arg  Lys  Leu  Val  Asp  Phe  Arg  Glu  Leu  Asn  Lys  Arg  Thr
         225                      230                 235                           240

Gln  Asp  Phe  Trp  Glu  Val  Gln  Leu  Gly  Ile  Pro  His  Pro  Ala  Gly  Leu
                             245                      250                      255

Lys  Lys  Lys  Lys  Ser  Val  Thr  Val  Leu  Asp  Val  Gly  Asp  Ala  Tyr  Phe
                        260                 265                      270

Ser  Val  Pro  Leu  Asp  Glu  Asp  Phe  Arg  Lys  Tyr  Thr  Ala  Phe  Thr  Ile
                   275                 280                 285

Pro  Ser  Ile  Asn  Asn  Glu  Thr  Pro  Gly  Ile  Arg  Tyr  Gln  Tyr  Asn  Val
              290                 295                      300

Leu  Pro  Gln  Gly  Trp  Lys  Gly  Ser  Pro  Ala  Ile  Phe  Gln  Ser  Ser  Met
         305                      310                 315                           320

Thr  Lys  Ile  Leu  Glu  Pro  Phe  Arg  Lys  Gln  Asn  Pro  Asp  Ile  Val  Ile
                             325                      330                      335

Tyr  Gln  Tyr  Met  Asp  Asp  Leu  Tyr  Val  Gly  Ser  Asp  Leu  Glu  Ile  Gly
                        340                 345                      350

Gln  His  Arg  Thr  Lys  Ile  Glu  Glu  Leu  Arg  Gln  His  Leu  Leu  Arg  Trp
                   355                 360                 365

Gly  Leu  Thr  Thr  Pro  Asp  Lys  Lys  His  Gln  Lys  Glu  Pro  Pro  Phe  Leu
              370                 375                      380

Trp  Met  Gly  Tyr  Glu  Leu  His  Pro  Asp  Lys  Trp  Thr  Val  Gln  Pro  Ile
         385                      390                 395                           400

Val  Leu  Pro  Glu  Lys  Asp  Ser  Trp  Thr  Val  Asn  Asp  Ile  Gln  Lys  Leu
                             405                      410                      415

Val  Gly  Lys  Leu  Asn  Trp  Ala  Ser  Gln  Ile  Tyr  Pro  Gly  Ile  Lys  Val
                        420                 425                      430

Arg  Gln  Leu  Cys  Lys  Leu  Leu  Arg  Gly  Thr  Lys  Ala  Leu  Thr  Glu  Val
                   435                 440                 445

Ile  Pro  Leu  Thr  Glu  Glu  Ala  Glu  Leu  Glu  Leu  Ala  Glu  Asn  Arg  Glu
              450                 455                      460
```

```
Ile  Leu  Lys  Glu  Pro  Val  His  Gly  Val  Tyr  Tyr  Asp  Pro  Ser  Lys  Asp
465                 470                 475                           480

Leu  Ile  Ala  Glu  Ile  Gln  Lys  Gln  Gly  Gln  Trp  Thr  Tyr  Gln
               485                 490                      495

Ile  Tyr  Gln  Glu  Pro  Phe  Lys  Asn  Leu  Lys  Thr  Gly  Lys  Tyr  Ala  Arg
               500                 505                      510

Met  Arg  Gly  Ala  His  Thr  Asn  Asp  Val  Lys  Gln  Leu  Thr  Glu  Ala  Val
          515                      520                      525

Gln  Lys  Ile  Thr  Thr  Glu  Ser  Ile  Val  Ile  Trp  Gly  Lys  Thr  Pro  Lys
530                      535                      540

Phe  Lys  Leu  Pro  Ile  Gln  Lys  Glu  Thr  Trp  Glu  Thr  Trp  Trp  Thr  Glu
545                 550                 555                           560

Tyr  Trp  Gln  Ala  Thr  Trp  Ile  Pro  Glu  Trp  Glu  Phe  Val  Asn  Thr  Pro
               565                 570                      575

Pro  Leu  Val  Lys  Leu  Trp  Tyr  Gln  Leu  Glu  Lys  Glu  Pro  Ile  Val  Gly
               580                 585                      590

Ala  Glu  Thr  Phe  Tyr  Val  Asp  Gly  Ala  Ala  Asn  Arg  Glu  Thr  Lys  Leu
          595                 600                      605

Gly  Lys  Ala  Gly  Tyr  Val  Thr  Asn  Arg  Gly  Arg  Gln  Lys  Val  Val  Thr
     610                      615                      620

Leu  Thr  Asp  Thr  Thr  Asn  Gln  Lys  Thr  Glu  Leu  Gln  Ala  Ile  Tyr  Leu
625                      630                      635                      640

Ala  Leu  Gln  Asp  Ser  Gly  Leu  Glu  Val  Asn  Ile  Val  Thr  Asp  Ser  Gln
                    645                      650                      655

Tyr  Ala  Leu  Gly  Ile  Ile  Gln  Ala  Gln  Pro  Asp  Gln  Ser  Glu  Ser  Glu
               660                      665                      670

Leu  Val  Asn  Gln  Ile  Ile  Glu  Gln  Leu  Ile  Lys  Lys  Glu  Lys  Val  Tyr
               675                      680                      685

Leu  Ala  Trp  Val  Pro  Ala  His  Lys  Gly  Ile  Gly  Gly  Asn  Glu  Gln  Val
          690                      695                      700

Asp  Lys  Leu  Val  Ser  Ala  Gly  Ile  Arg  Lys  Val  Leu  Phe  Leu  Asp  Gly
705                      710                      715                      720

Ile  Asp  Lys  Ala  Gln  Asp  Glu  His  Glu  Lys  Tyr  His  Ser  Asn  Trp  Arg
                    725                      730                      735

Ala  Met  Ala  Ser  Asp  Phe  Asn  Leu  Pro  Val  Val  Ala  Lys  Glu  Ile
               740                 745                      750

Val  Ala  Ser  Cys  Asp  Lys  Cys  Gln  Leu  Lys  Gly  Glu  Ala  Met  His  Gly
          755                 760                      765

Gln  Val  Asp  Cys  Ser  Pro  Gly  Ile  Trp  Gln  Leu  Asp  Cys  Thr  His  Leu
     770                      775                      780

Glu  Gly  Lys  Val  Ile  Leu  Val  Ala  Val  His  Val  Ala  Ser  Gly  Tyr  Ile
785                      790                      795                      800

Glu  Ala  Glu  Val  Ile  Pro  Ala  Glu  Thr  Gly  Gln  Glu  Thr  Ala  Tyr  Phe
                    805                      810                      815

Leu  Leu  Lys  Leu  Ala  Gly  Arg  Trp  Pro  Val  Lys  Thr  Ile  His  Thr  Asp
                    820                      825                      830

Asn  Gly  Ser  Asn  Phe  Thr  Gly  Ala  Thr  Val  Arg  Ala  Ala  Cys  Trp  Trp
          835                      840                      845

Ala  Gly  Ile  Lys  Gln  Glu  Phe  Gly  Ile  Pro  Tyr  Asn  Pro  Gln  Ser  Gln
          850                 855                      860

Gly  Val  Val  Glu  Ser  Met  Asn  Lys  Glu  Leu  Lys  Lys  Ile  Ile  Gly  Gln
865                      870                      875                      880

Val  Arg  Asp  Gln  Ala  Glu  His  Leu  Lys  Thr  Ala  Val  Gln  Met  Ala  Val
```

|     |     |     |     | 885 |     |     |     |     | 890 |     |     |     |     | 895 |     |
| --- | --- | --- | --- | --- | --- | --- | --- | --- | --- | --- | --- | --- | --- | --- | --- |
| Phe | Ile | His | Asn<br>900 | Phe | Lys | Arg | Lys | Gly<br>905 | Ile | Gly | Gly | Tyr<br>910 | Ser | Ala |
| Gly | Glu | Arg<br>915 | Ile | Val | Asp | Ile<br>920 | Ile | Ala | Thr | Asp | Ile<br>925 | Gln | Thr | Lys | Glu |
| Leu | Gln<br>930 | Lys | Gln | Ile | Thr | Lys<br>935 | Ile | Gln | Asn | Phe | Arg<br>940 | Val | Tyr | Tyr | Arg |
| Asp<br>945 | Ser | Arg | Asn | Ser | Leu<br>950 | Trp | Lys | Gly | Pro | Ala<br>955 | Lys | Leu | Leu | Trp | Lys<br>960 |
| Gly | Glu | Gly | Ala | Val<br>965 | Val | Ile | Gln | Asp | Asn<br>970 | Ser | Asp | Ile | Lys | Val<br>975 | Val |
| Pro | Arg | Arg | Lys<br>980 | Ala | Lys | Ile | Ile | Arg<br>985 | Asp | Tyr | Gly | Lys | Gln<br>990 | Met | Ala |
| Gly | Asp | Asp<br>995 | Cys | Val | Ala | Ser | Arg<br>1000 | Gln | Asp | Glu | Asp | Xaa<br>1005 |     |     |     |

( 2 ) INFORMATION FOR SEQ ID NO:2:

( i ) SEQUENCE CHARACTERISTICS:
        ( A ) LENGTH: 1016 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Human immunodeficiency virus type 1
        ( B ) STRAIN: BH102

( x i ) SEQUENCE DESCRIPTION: SEQ ID NO:2:

| Phe<br>1 | Phe | Arg | Glu | Asp<br>5 | Leu | Ala | Phe | Leu | Gln<br>10 | Gly | Lys | Ala | Arg | Glu<br>15 | Phe |
| --- | --- | --- | --- | --- | --- | --- | --- | --- | --- | --- | --- | --- | --- | --- | --- |
| Ser | Ser | Glu | Gln<br>20 | Thr | Arg | Ala | Asn | Ser<br>25 | Pro | Thr | Ile | Ser | Ser<br>30 | Glu | Gln |
| Thr | Arg | Ala<br>35 | Asn | Ser | Pro | Thr | Arg<br>40 | Arg | Glu | Leu | Gln | Val<br>45 | Trp | Gly | Arg |
| Asp | Asn<br>50 | Asn | Ser | Pro | Ser | Glu<br>55 | Ala | Gly | Ala | Asp | Arg<br>60 | Gln | Gly | Thr | Val |
| Ser<br>65 | Phe | Asn | Phe | Pro | Gln<br>70 | Ile | Thr | Leu | Trp | Gln<br>75 | Arg | Pro | Leu | Val | Thr<br>80 |
| Ile | Lys | Ile | Gly | Gly<br>85 | Gln | Leu | Lys | Glu | Ala<br>90 | Leu | Leu | Asp | Thr | Gly<br>95 | Ala |
| Asp | Asp | Thr | Val<br>100 | Leu | Glu | Glu | Met | Ser<br>105 | Leu | Pro | Gly | Arg | Trp<br>110 | Lys | Pro |
| Lys | Met | Ile<br>115 | Gly | Gly | Ile | Gly | Gly<br>120 | Phe | Ile | Lys | Val | Arg<br>125 | Gln | Tyr | Asp |
| Gln | Ile<br>130 | Leu | Ile | Glu | Ile | Cys<br>135 | Gly | His | Lys | Ala | Ile<br>140 | Gly | Thr | Val | Leu |
| Val<br>145 | Gly | Pro | Thr | Pro | Val<br>150 | Asn | Ile | Ile | Gly | Arg<br>155 | Asn | Leu | Leu | Thr | Gln<br>160 |
| Ile | Gly | Cys | Thr | Leu<br>165 | Asn | Phe | Pro | Ile | Ser<br>170 | Pro | Ile | Glu | Thr | Val<br>175 | Pro |
| Val | Lys | Leu | Lys<br>180 | Pro | Gly | Met | Asp | Gly<br>185 | Pro | Lys | Val | Lys | Gln<br>190 | Trp | Pro |

-continued

```
Leu Thr Glu Glu Lys Ile Lys Ala Leu Val Glu Ile Cys Thr Glu Met
        195                 200                 205
Glu Lys Glu Gly Lys Ile Ser Lys Ile Gly Pro Glu Asn Pro Tyr Asn
        210                 215                 220
Thr Pro Val Phe Ala Ile Lys Lys Lys Asp Ser Thr Lys Trp Arg Lys
225                     230                 235                 240
Leu Val Asp Phe Arg Glu Leu Asn Lys Arg Thr Gln Asp Phe Trp Glu
                    245                 250                 255
Val Gln Leu Gly Ile Pro His Pro Ala Gly Leu Lys Lys Lys Ser
                260                 265                 270
Val Thr Val Leu Asp Val Gly Asp Ala Tyr Phe Ser Val Pro Leu Asp
            275                 280                 285
Glu Asp Phe Arg Lys Tyr Thr Ala Phe Thr Ile Pro Ser Ile Asn Asn
        290                 295                 300
Glu Thr Pro Gly Ile Arg Tyr Gln Tyr Asn Val Leu Pro Gln Gly Trp
305                 310                 315                 320
Lys Gly Ser Pro Ala Ile Phe Gln Ser Ser Met Thr Lys Ile Leu Glu
                325                 330                 335
Pro Phe Lys Lys Gln Asn Pro Asp Ile Val Ile Tyr Gln Tyr Met Asp
            340                 345                 350
Asp Leu Tyr Val Gly Ser Asp Leu Glu Ile Gly Gln His Arg Thr Lys
            355                 360                 365
Ile Glu Glu Leu Arg Gln His Leu Leu Arg Trp Gly Leu Thr Thr Pro
370                 375                 380
Asp Lys Lys His Gln Lys Glu Pro Pro Phe Leu Trp Met Gly Tyr Glu
385                 390                 395                 400
Leu His Pro Asp Lys Trp Thr Val Gln Pro Ile Val Leu Pro Glu Lys
                    405                 410                 415
Asp Ser Trp Thr Val Asn Asp Ile Gln Lys Leu Val Gly Lys Leu Asn
            420                 425                 430
Trp Ala Ser Gln Ile Tyr Pro Gly Ile Lys Val Arg Gln Leu Cys Lys
        435                 440                 445
Leu Leu Arg Gly Thr Lys Ala Leu Thr Glu Val Ile Pro Leu Thr Glu
450                 455                 460
Glu Ala Glu Leu Glu Leu Ala Glu Asn Arg Glu Ile Leu Lys Glu Pro
465                 470                 475                 480
Val His Gly Val Tyr Tyr Asp Pro Ser Lys Asp Leu Ile Ala Glu Ile
                485                 490                 495
Gln Lys Gln Gly Gln Gly Gln Trp Thr Tyr Gln Ile Tyr Gln Glu Pro
            500                 505                 510
Phe Lys Asn Leu Lys Thr Gly Lys Tyr Ala Arg Met Arg Gly Ala His
        515                 520                 525
Thr Asn Asp Val Lys Gln Leu Thr Glu Ala Val Gln Lys Ile Thr Thr
            530                 535                 540
Glu Ser Ile Val Ile Trp Gly Lys Thr Pro Lys Phe Lys Leu Pro Ile
545                 550                 555                 560
Gln Lys Glu Thr Trp Glu Thr Trp Trp Thr Glu Tyr Trp Gln Ala Thr
                    565                 570                 575
Trp Ile Pro Glu Trp Glu Phe Val Asn Thr Pro Pro Leu Val Lys Leu
                580                 585                 590
Trp Tyr Gln Leu Glu Lys Glu Pro Ile Val Gly Ala Glu Thr Phe Tyr
            595                 600                 605
Val Asp Gly Ala Ala Asn Arg Glu Thr Lys Leu Gly Lys Ala Gly Tyr
            610                 615                 620
```

| | | | | | | | | | | | | | | |
|---|---|---|---|---|---|---|---|---|---|---|---|---|---|---|
| Val 625 | Thr | Asn | Lys | Gly | Arg 630 | Gln | Lys | Val | Val | Pro 635 | Leu | Thr | Asn | Thr | Thr 640 |
| Asn | Gln | Lys | Thr | Glu 645 | Leu | Gln | Ala | Ile | Tyr 650 | Leu | Ala | Leu | Gln | Asp | Ser 655 |
| Gly | Leu | Glu | Val 660 | Asn | Ile | Val | Thr | Asp 665 | Ser | Gln | Tyr | Ala | Leu 670 | Gly | Ile |
| Ile | Gln | Ala 675 | Gln | Pro | Asp | Lys | Ser 680 | Glu | Ser | Glu | Leu | Val 685 | Asn | Gln | Ile |
| Ile | Glu 690 | Gln | Leu | Ile | Lys | Lys 695 | Glu | Lys | Val | Tyr | Leu 700 | Ala | Trp | Val | Pro |
| Ala 705 | His | Lys | Gly | Ile | Gly 710 | Gly | Asn | Glu | Gln | Val 715 | Asp | Lys | Leu | Val | Ser 720 |
| Ala | Gly | Ile | Arg | Lys 725 | Ile | Leu | Phe | Leu | Asp 730 | Gly | Ile | Asp | Lys | Ala 735 | Gln |
| Asp | Glu | His 740 | Glu | Lys | Tyr | His | Ser 745 | Asn | Trp | Arg | Ala | Met 750 | Ala | Ser | Asp |
| Phe | Asn 755 | Leu | Pro | Pro | Val | Val 760 | Ala | Lys | Glu | Ile | Val 765 | Ala | Ser | Cys | Asp |
| Lys 770 | Cys | Gln | Leu | Lys | Gly 775 | Glu | Ala | Met | His | Gly 780 | Gln | Val | Asp | Cys | Ser |
| Pro 785 | Gly | Ile | Trp | Gln | Leu 790 | Asp | Cys | Thr | His | Leu 795 | Glu | Gly | Lys | Val | Ile 800 |
| Leu | Val | Ala | Val | His 805 | Val | Ala | Ser | Gly | Tyr 810 | Ile | Glu | Ala | Glu | Val 815 | Ile |
| Pro | Ala | Glu | Thr 820 | Gly | Gln | Glu | Thr | Ala 825 | Tyr | Phe | Leu | Leu | Lys 830 | Leu | Ala |
| Gly | Arg | Trp 835 | Pro | Val | Lys | Thr | Ile 840 | His | Thr | Asp | Asn | Gly 845 | Ser | Asn | Phe |
| Thr | Ser | Ala 850 | Thr | Val | Lys | Ala 855 | Ala | Cys | Trp | Trp | Ala 860 | Gly | Ile | Lys | Gln |
| Glu 865 | Phe | Gly | Ile | Pro | Tyr 870 | Asn | Pro | Gln | Ser | Gln 875 | Gly | Val | Val | Glu | Ser 880 |
| Met | Asn | Lys | Glu | Leu 885 | Lys | Lys | Ile | Ile | Gly 890 | Gln | Val | Arg | Asp | Gln 895 | Ala |
| Glu | His | Leu | Lys 900 | Thr | Ala | Val | Gln | Met 905 | Ala | Val | Phe | Ile | His 910 | Asn | Phe |
| Lys | Arg | Lys 915 | Gly | Gly | Ile | Gly | Gly 920 | Tyr | Ser | Ala | Gly | Glu 925 | Arg | Ile | Val |
| Asp | Ile 930 | Ile | Ala | Thr | Asp | Ile 935 | Gln | Thr | Lys | Glu | Leu 940 | Gln | Lys | Gln | Ile |
| Thr 945 | Lys | Ile | Gln | Asn | Phe 950 | Arg | Val | Tyr | Tyr | Arg 955 | Asp | Ser | Arg | Asn | Pro 960 |
| Leu | Trp | Lys | Gly | Pro 965 | Ala | Lys | Leu | Leu | Trp 970 | Lys | Gly | Glu | Gly | Ala 975 | Val |
| Val | Ile | Gln | Asp 980 | Asn | Ser | Asp | Ile | Lys 985 | Val | Val | Pro | Arg | Arg 990 | Lys | Ala |
| Lys | Ile | Ile 995 | Arg | Asp | Tyr | Gly | Lys 1000 | Gln | Met | Ala | Gly | Asp 1005 | Asp | Cys | Val |
| Ala | Ser | Arg 1010 | Gln | Asp | Glu | Asp | Xaa 1015 | | | | | | | | |

( 2 ) INFORMATION FOR SEQ ID NO:3:

( i ) SEQUENCE CHARACTERISTICS:

( A ) LENGTH: 1016 amino acids
( B ) TYPE: amino acid
( C ) STRANDEDNESS: Not Relevant
( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
( A ) ORGANISM: Human immunodeficiency virus type 1
( B ) STRAIN: BH5

( x i ) SEQUENCE DESCRIPTION: SEQ ID NO:3:

| Phe | Phe | Arg | Glu | Asp | Leu | Ala | Phe | Leu | Gln | Gly | Lys | Ala | Arg | Glu | Phe |
|---|---|---|---|---|---|---|---|---|---|---|---|---|---|---|---|
| 1 | | | | 5 | | | | | 10 | | | | | 15 | |
| Ser | Ser | Glu | Gln | Thr | Arg | Ala | Asn | Ser | Pro | Thr | Ile | Ser | Ser | Glu | Gln |
| | | | 20 | | | | | 25 | | | | | 30 | | |
| Thr | Arg | Ala | Asn | Ser | Pro | Thr | Arg | Arg | Glu | Leu | Gln | Val | Trp | Gly | Arg |
| | | | 35 | | | | 40 | | | | | 45 | | | |
| Asp | Asn | Asn | Ser | Pro | Ser | Glu | Ala | Gly | Ala | Asp | Arg | Gln | Gly | Thr | Val |
| | 50 | | | | | 55 | | | | | 60 | | | | |
| Ser | Phe | Asn | Phe | Pro | Gln | Ile | Thr | Leu | Trp | Gln | Arg | Pro | Leu | Val | Thr |
| 65 | | | | | 70 | | | | | 75 | | | | | 80 |
| Ile | Lys | Ile | Gly | Gly | Gln | Leu | Lys | Glu | Ala | Leu | Leu | Asp | Thr | Gly | Ala |
| | | | | 85 | | | | | 90 | | | | | 95 | |
| Asp | Asp | Thr | Val | Leu | Glu | Glu | Met | Ser | Leu | Pro | Gly | Arg | Trp | Lys | Pro |
| | | | 100 | | | | | 105 | | | | | 110 | | |
| Lys | Met | Ile | Gly | Gly | Ile | Gly | Gly | Phe | Ile | Lys | Val | Arg | Gln | Tyr | Asp |
| | | 115 | | | | | 120 | | | | | 125 | | | |
| Gln | Ile | Leu | Ile | Glu | Ile | Cys | Gly | His | Lys | Ala | Ile | Gly | Thr | Val | Leu |
| | 130 | | | | | 135 | | | | | 140 | | | | |
| Val | Gly | Pro | Thr | Pro | Val | Asn | Ile | Ile | Gly | Arg | Asn | Leu | Leu | Thr | Gln |
| 145 | | | | | 150 | | | | | 155 | | | | | 160 |
| Ile | Gly | Cys | Thr | Leu | Asn | Phe | Pro | Ile | Ser | Pro | Ile | Glu | Thr | Val | Pro |
| | | | | 165 | | | | | 170 | | | | | 175 | |
| Val | Lys | Leu | Lys | Pro | Gly | Met | Asp | Gly | Pro | Lys | Val | Lys | Gln | Trp | Pro |
| | | | 180 | | | | | 185 | | | | | 190 | | |
| Leu | Thr | Glu | Glu | Lys | Ile | Lys | Ala | Leu | Val | Glu | Ile | Cys | Thr | Glu | Met |
| | | 195 | | | | | 200 | | | | | 205 | | | |
| Glu | Lys | Glu | Gly | Lys | Ile | Ser | Lys | Ile | Gly | Pro | Glu | Asn | Pro | Tyr | Asn |
| | 210 | | | | | 215 | | | | | 220 | | | | |
| Thr | Pro | Val | Phe | Ala | Ile | Lys | Lys | Lys | Asp | Ser | Thr | Lys | Trp | Arg | Lys |
| 225 | | | | | 230 | | | | | 235 | | | | | 240 |
| Leu | Val | Asp | Phe | Arg | Glu | Leu | Asn | Arg | Arg | Thr | Gln | Asp | Phe | Trp | Glu |
| | | | | 245 | | | | | 250 | | | | | 255 | |
| Val | Gln | Leu | Gly | Ile | Pro | His | Pro | Ala | Gly | Leu | Lys | Lys | Lys | Lys | Ser |
| | | | 260 | | | | | 265 | | | | | 270 | | |
| Val | Thr | Val | Leu | Asp | Val | Gly | Asp | Ala | Tyr | Phe | Ser | Val | Pro | Leu | Asp |
| | | 275 | | | | | 280 | | | | | 285 | | | |
| Glu | Asp | Phe | Arg | Lys | Tyr | Thr | Ala | Phe | Thr | Ile | Pro | Ser | Ile | Asn | Asn |
| | 290 | | | | | 295 | | | | | 300 | | | | |
| Glu | Thr | Pro | Gly | Ser | Gly | Tyr | Gln | Tyr | Asn | Val | Leu | Pro | Gln | Gly | Trp |
| 305 | | | | | 310 | | | | | 315 | | | | | 320 |
| Lys | Gly | Ser | Pro | Ala | Ile | Phe | Gln | Ser | Ser | Met | Thr | Lys | Ile | Leu | Glu |
| | | | | 325 | | | | | 330 | | | | | 335 | |

```
Pro  Phe  Arg  Lys  Gln  Asn  Pro  Asp  Ile  Val  Ile  Tyr  Gln  Tyr  Met  Asp
               340                 345                           350

Asp  Leu  Tyr  Val  Gly  Ser  Asp  Leu  Glu  Ile  Gly  Gln  His  Arg  Thr  Lys
          355                 360                      365

Ile  Glu  Leu  Arg  Gln  His  Leu  Leu  Arg  Trp  Gly  Phe  Thr  Thr  Pro
     370                 375                      380

Asp  Lys  Lys  His  Gln  Lys  Glu  Pro  Pro  Phe  Leu  Trp  Met  Gly  Tyr  Glu
385                      390                      395                      400

Leu  His  Pro  Asp  Lys  Trp  Thr  Ile  Gln  Pro  Ile  Val  Leu  Pro  Glu  Lys
               405                      410                           415

Asp  Ser  Trp  Thr  Val  Asn  Asp  Ile  Gln  Lys  Leu  Val  Gly  Lys  Leu  Asn
               420                      425                           430

Trp  Ala  Ser  Gln  Ile  Tyr  Pro  Gly  Ile  Lys  Val  Arg  Gln  Leu  Cys  Lys
          435                      440                      445

Leu  Leu  Arg  Gly  Thr  Lys  Ala  Leu  Thr  Glu  Val  Ile  Pro  Leu  Thr  Glu
          450                      455                 460

Glu  Ala  Glu  Leu  Glu  Leu  Ala  Glu  Asn  Arg  Glu  Ile  Leu  Lys  Glu  Pro
465                      470                 475                           480

Val  His  Gly  Val  Tyr  Tyr  Asp  Pro  Ser  Lys  Asp  Leu  Ile  Ala  Glu  Ile
                    485                 490                           495

Gln  Lys  Gln  Gly  Gln  Gly  Gln  Trp  Thr  Tyr  Gln  Ile  Tyr  Gln  Glu  Pro
               500                      505                      510

Phe  Lys  Asn  Leu  Lys  Thr  Gly  Lys  Tyr  Ala  Arg  Met  Arg  Gly  Ala  His
          515                      520                      525

Thr  Asn  Asp  Val  Lys  Gln  Leu  Thr  Glu  Ala  Val  Gln  Lys  Ile  Thr  Thr
     530                      535                 540

Glu  Ser  Ile  Val  Ile  Trp  Gly  Lys  Thr  Pro  Lys  Phe  Lys  Leu  Pro  Ile
545                           550                      555                      560

Gln  Lys  Glu  Thr  Trp  Glu  Thr  Trp  Trp  Thr  Glu  Tyr  Trp  Gln  Ala  Thr
                    565                      570                      575

Trp  Ile  Pro  Glu  Trp  Glu  Phe  Val  Asn  Thr  Pro  Pro  Leu  Val  Lys  Leu
               580                      585                      590

Trp  Tyr  Gln  Leu  Glu  Lys  Glu  Pro  Ile  Val  Gly  Ala  Glu  Thr  Phe  Tyr
          595                      600                      605

Val  Asp  Gly  Ala  Ala  Ser  Arg  Glu  Thr  Lys  Leu  Gly  Lys  Ala  Gly  Tyr
610                      615                      620

Val  Thr  Asn  Arg  Gly  Arg  Gln  Lys  Val  Val  Thr  Leu  Thr  His  Thr  Thr
625                      630                      635                      640

Asn  Gln  Lys  Thr  Glu  Leu  Gln  Ala  Ile  His  Leu  Ala  Leu  Gln  Asp  Ser
               645                      650                      655

Gly  Leu  Glu  Val  Asn  Ile  Val  Thr  Asp  Ser  Gln  Tyr  Ala  Leu  Gly  Ile
               660                      665                      670

Ile  Gln  Ala  Gln  Pro  Asp  Lys  Ser  Glu  Ser  Glu  Leu  Val  Asn  Gln  Ile
          675                      680                      685

Ile  Glu  Gln  Leu  Ile  Lys  Lys  Glu  Lys  Val  Tyr  Leu  Ala  Trp  Val  Pro
     690                      695                      700

Ala  His  Lys  Gly  Ile  Gly  Gly  Asn  Glu  Gln  Val  Asp  Lys  Leu  Val  Ser
705                      710                      715                      720

Ala  Gly  Ile  Arg  Lys  Ile  Leu  Phe  Leu  Asp  Gly  Ile  Asp  Lys  Ala  Gln
                    725                      730                      735

Glu  Glu  His  Glu  Lys  Tyr  His  Ser  Asn  Trp  Arg  Ala  Met  Ala  Ser  Asp
               740                      745                      750

Phe  Asn  Leu  Pro  Pro  Val  Val  Ala  Lys  Glu  Ile  Val  Ala  Ser  Cys  Asp
          755                      760                      765
```

-continued

| | | | | | | | | | | | | | |
|---|---|---|---|---|---|---|---|---|---|---|---|---|---|
| Lys | Cys | Gln | Leu | Lys | Gly | Glu | Ala | Met | His | Gly | Gln | Val | Asp | Cys | Ser |
| | | 770 | | | | 775 | | | | 780 | | | |
| Pro | Gly | Ile | Trp | Gln | Leu | Asp | Cys | Thr | His | Leu | Glu | Gly | Lys | Val | Ile |
| 785 | | | | | 790 | | | | | 795 | | | | | 800 |
| Leu | Val | Ala | Val | His | Val | Ala | Ser | Gly | Tyr | Ile | Glu | Ala | Glu | Val | Ile |
| | | | | 805 | | | | | 810 | | | | | 815 | |
| Pro | Ala | Glu | Thr | Gly | Gln | Glu | Thr | Ala | Tyr | Phe | Leu | Leu | Lys | Leu | Ala |
| | | | 820 | | | | | 825 | | | | | 830 | | |
| Gly | Arg | Trp | Pro | Val | Lys | Thr | Ile | His | Thr | Asp | Asn | Gly | Ser | Asn | Phe |
| | | 835 | | | | | 840 | | | | | 845 | | | |
| Thr | Ser | Ala | Thr | Val | Lys | Ala | Ala | Cys | Trp | Trp | Ala | Gly | Ile | Lys | Gln |
| | | 850 | | | | | 855 | | | | | 860 | | | |
| Glu | Phe | Gly | Ile | Pro | Tyr | Asn | Pro | Gln | Ser | Gln | Gly | Val | Val | Glu | Ser |
| 865 | | | | | 870 | | | | | 875 | | | | | 880 |
| Met | Asn | Lys | Glu | Leu | Lys | Lys | Ile | Ile | Gly | Gln | Val | Arg | Asp | Gln | Ala |
| | | | | 885 | | | | | 890 | | | | | 895 | |
| Glu | His | Leu | Lys | Thr | Ala | Val | Gln | Met | Ala | Val | Phe | Ile | His | Asn | Phe |
| | | | 900 | | | | | 905 | | | | | 910 | | |
| Lys | Arg | Lys | Gly | Gly | Ile | Gly | Gly | Tyr | Ser | Ala | Gly | Glu | Arg | Ile | Val |
| | | 915 | | | | | 920 | | | | | 925 | | | |
| Asp | Ile | Ile | Ala | Thr | Asp | Ile | Gln | Thr | Lys | Glu | Leu | Gln | Lys | Gln | Ile |
| | 930 | | | | | 935 | | | | | 940 | | | | |
| Thr | Lys | Ile | Gln | Asn | Phe | Arg | Val | Tyr | Tyr | Arg | Asp | Ser | Arg | Asn | Pro |
| 945 | | | | | 950 | | | | | 955 | | | | | 960 |
| Leu | Trp | Lys | Gly | Pro | Ala | Lys | Leu | Leu | Trp | Lys | Gly | Glu | Gly | Ala | Val |
| | | | | 965 | | | | | 970 | | | | | 975 | |
| Val | Ile | Gln | Asp | Asn | Ser | Asp | Ile | Lys | Val | Val | Pro | Arg | Arg | Lys | Ala |
| | | | 980 | | | | | 985 | | | | | 990 | | |
| Lys | Ile | Ile | Arg | Asp | Tyr | Gly | Lys | Gln | Met | Ala | Gly | Asp | Asp | Cys | Val |
| | | 995 | | | | | 1000 | | | | | 1005 | | | |
| Ala | Ser | Arg | Gln | Asp | Glu | Asp | Xaa | | | | | | | | |
| | 1010 | | | | | 1015 | | | | | | | | | |

( 2 ) INFORMATION FOR SEQ ID NO:4:

( i ) SEQUENCE CHARACTERISTICS:
        ( A ) LENGTH: 1016 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Human immunodeficiency virus type 1
        ( B ) STRAIN: PV22

( x i ) SEQUENCE DESCRIPTION: SEQ ID NO:4:

| | | | | | | | | | | | | | | | |
|---|---|---|---|---|---|---|---|---|---|---|---|---|---|---|---|
| Phe | Phe | Arg | Glu | Asp | Leu | Ala | Phe | Leu | Gln | Gly | Lys | Ala | Arg | Glu | Phe |
| 1 | | | | 5 | | | | | 10 | | | | | 15 | |
| Ser | Ser | Glu | Gln | Thr | Arg | Ala | Asn | Ser | Pro | Thr | Ile | Ser | Ser | Glu | Gln |
| | | | 20 | | | | | 25 | | | | | 30 | | |
| Thr | Arg | Ala | Asn | Ser | Pro | Thr | Arg | Arg | Glu | Leu | Gln | Val | Trp | Gly | Arg |
| | | 35 | | | | | 40 | | | | | 45 | | | |
| Asp | Asn | Asn | Ser | Pro | Ser | Glu | Ala | Gly | Ala | Asp | Arg | Gln | Gly | Thr | Val |

```
              50                      55                         60

Ser  Phe  Asn  Phe  Pro  Gln  Ile  Thr  Leu  Trp  Gln  Arg  Pro  Leu  Val  Thr
  65                       70                      75                       80

Ile  Lys  Ile  Gly  Gly  Gln  Leu  Lys  Glu  Ala  Leu  Leu  Asp  Thr  Gly  Ala
                      85                      90                       95

Asp  Asp  Thr  Val  Leu  Glu  Glu  Met  Ser  Leu  Pro  Gly  Arg  Trp  Lys  Pro
                      100                     105                      110

Lys  Met  Ile  Gly  Gly  Ile  Gly  Gly  Phe  Ile  Lys  Val  Arg  Gln  Tyr  Asp
            115                     120                     125

Gln  Ile  Leu  Ile  Glu  Ile  Cys  Gly  His  Lys  Ala  Ile  Gly  Thr  Val  Leu
            130                     135                     140

Val  Gly  Pro  Thr  Pro  Val  Asn  Ile  Ile  Gly  Arg  Asn  Leu  Leu  Thr  Gln
  145                      150                     155                      160

Ile  Gly  Cys  Thr  Leu  Asn  Phe  Pro  Ile  Ser  Pro  Ile  Glu  Thr  Val  Pro
                      165                     170                      175

Val  Lys  Leu  Lys  Pro  Gly  Met  Asp  Gly  Pro  Lys  Val  Lys  Gln  Trp  Pro
                 180                     185                      190

Leu  Thr  Glu  Glu  Lys  Ile  Lys  Ala  Leu  Val  Glu  Ile  Cys  Thr  Glu  Met
                 195                     200                      205

Glu  Lys  Glu  Gly  Lys  Ile  Ser  Lys  Ile  Gly  Pro  Glu  Asn  Pro  Tyr  Asn
            210                     215                     220

Thr  Pro  Val  Phe  Ala  Ile  Lys  Lys  Lys  Asp  Ser  Thr  Lys  Trp  Arg  Lys
  225                      230                     235                      240

Leu  Val  Asp  Phe  Arg  Glu  Leu  Asn  Lys  Arg  Thr  Gln  Asp  Phe  Trp  Glu
                 245                     250                      255

Val  Gln  Leu  Gly  Ile  Pro  His  Pro  Ala  Gly  Leu  Lys  Lys  Lys  Lys  Ser
                 260                     265                      270

Val  Thr  Val  Leu  Asp  Val  Gly  Asp  Ala  Tyr  Phe  Ser  Val  Pro  Leu  Asp
            275                     280                     285

Glu  Asp  Phe  Arg  Lys  Tyr  Thr  Ala  Phe  Thr  Ile  Pro  Ser  Ile  Asn  Asn
  290                      295                     300

Glu  Thr  Pro  Gly  Ile  Arg  Tyr  Gln  Tyr  Asn  Val  Leu  Pro  Gln  Gly  Trp
  305                      310                     315                      320

Lys  Gly  Ser  Pro  Ala  Ile  Phe  Gln  Ser  Ser  Met  Thr  Lys  Ile  Leu  Glu
                 325                     330                      335

Pro  Phe  Arg  Lys  Gln  Asn  Pro  Asp  Ile  Val  Ile  Tyr  Gln  Tyr  Met  Asp
                 340                     345                      350

Asp  Leu  Tyr  Val  Gly  Ser  Asp  Leu  Glu  Ile  Gly  Gln  His  Arg  Thr  Lys
            355                     360                     365

Ile  Glu  Glu  Leu  Arg  Gln  His  Leu  Leu  Arg  Trp  Gly  Leu  Thr  Thr  Pro
       370                     375                     380

Asp  Lys  Lys  His  Gln  Lys  Glu  Pro  Pro  Phe  Leu  Trp  Met  Gly  Tyr  Glu
  385                      390                     395                      400

Leu  His  Pro  Asp  Lys  Trp  Thr  Val  Gln  Pro  Ile  Val  Leu  Pro  Glu  Lys
                 405                     410                      415

Asp  Ser  Trp  Thr  Val  Asn  Asp  Ile  Gln  Lys  Leu  Val  Gly  Lys  Leu  Asn
                 420                     425                      430

Trp  Ala  Ser  Gln  Ile  Tyr  Pro  Gly  Ile  Lys  Val  Arg  Gln  Leu  Cys  Lys
            435                     440                     445

Leu  Leu  Arg  Gly  Thr  Lys  Ala  Leu  Thr  Glu  Val  Ile  Pro  Leu  Thr  Glu
  450                      455                     460

Glu  Ala  Glu  Leu  Glu  Leu  Ala  Glu  Asn  Arg  Glu  Ile  Leu  Lys  Glu  Pro
  465                      470                     475                      480
```

```
Val His Gly Val Tyr Tyr Asp Pro Ser Lys Asp Leu Ile Ala Glu Ile
            485             490                 495
Gln Lys Gln Gly Gln Gly Gln Trp Thr Tyr Gln Ile Tyr Gln Glu Pro
            500             505                 510
Phe Lys Asn Leu Lys Thr Gly Lys Tyr Ala Arg Met Arg Gly Ala His
        515             520             525
Thr Asn Asp Val Lys Gln Leu Thr Glu Ala Val Gln Lys Ile Thr Thr
        530             535             540
Glu Ser Ile Val Ile Trp Gly Lys Thr Pro Lys Phe Lys Leu Pro Ile
545                 550             555                 560
Gln Lys Glu Thr Trp Glu Thr Trp Trp Thr Glu Tyr Trp Gln Ala Thr
                565             570                 575
Trp Ile Pro Glu Trp Glu Phe Val Asn Thr Pro Pro Leu Val Lys Leu
            580             585                 590
Trp Tyr Gln Leu Glu Lys Glu Pro Ile Val Gly Ala Glu Thr Phe Tyr
        595             600             605
Val Asp Gly Ala Ala Asn Arg Glu Thr Arg Leu Gly Lys Ala Gly Tyr
    610             615             620
Leu Thr Asn Lys Gly Arg Gln Lys Val Val Pro Leu Thr Asn Thr Thr
625             630             635                 640
Asn Gln Lys Thr Glu Leu Gln Ala Ile Tyr Leu Ala Leu Gln Asp Ser
            645             650             655
Gly Leu Glu Val Asn Ile Val Thr Asp Ser Gln Tyr Ala Leu Gly Ile
        660             665             670
Ile Gln Ala Gln Pro Asp Gln Ser Glu Ser Glu Leu Val Asn Gln Ile
        675             680             685
Ile Glu Gln Leu Ile Lys Lys Gln Lys Val Tyr Leu Ala Trp Val Pro
    690             695             700
Ala His Lys Gly Ile Gly Gly Asn Glu Gln Val Asp Lys Leu Val Ser
705             710             715                 720
Ala Gly Ile Arg Lys Ile Leu Phe Leu Asp Gly Ile Asp Lys Ala Gln
                725             730             735
Asp Glu His Glu Lys Tyr His Ser Asn Trp Arg Ala Met Ala Ser Asp
            740             745             750
Phe Asn Leu Pro Pro Val Val Ala Lys Glu Ile Val Ala Ser Cys Asp
        755             760             765
Lys Cys Gln Leu Lys Gly Glu Ala Met His Gly Gln Val Asp Cys Ser
        770             775             780
Pro Gly Ile Trp Gln Leu Asp Cys Thr His Leu Glu Gly Lys Val Ile
785             790             795                 800
Leu Val Ala Val His Val Ala Ser Gly Tyr Ile Glu Ala Glu Val Ile
                805             810             815
Pro Ala Glu Thr Gly Gln Glu Thr Ala Tyr Phe Leu Leu Lys Leu Ala
            820             825             830
Gly Arg Trp Pro Val Lys Thr Ile His Thr Asp Asn Gly Ser Asn Phe
        835             840             845
Thr Ser Ala Thr Val Lys Ala Ala Cys Trp Trp Ala Gly Ile Lys Gln
        850             855             860
Glu Phe Gly Ile Pro Tyr Asn Pro Gln Ser Gln Gly Val Val Glu Ser
865             870             875                 880
Met Asn Lys Glu Leu Lys Lys Ile Ile Gly Gln Val Arg Asp Gln Ala
                885             890             895
Glu His Leu Lys Thr Ala Val Gln Met Ala Val Phe Ile His Asn Phe
            900             905             910
```

-continued

```
Lys  Arg  Lys  Gly  Gly  Ile  Gly  Gly  Tyr  Ser  Ala  Gly  Glu  Arg  Ile  Val
          915                 920                      925

Asp  Ile  Ile  Ala  Thr  Asp  Ile  Gln  Thr  Lys  Glu  Leu  Gln  Lys  Gln  Ile
     930                 935                      940

Thr  Lys  Ile  Gln  Asn  Phe  Arg  Val  Tyr  Tyr  Arg  Asp  Ser  Arg  Asn  Pro
945                 950                 955                           960

Leu  Trp  Lys  Gly  Pro  Ala  Lys  Leu  Leu  Trp  Lys  Gly  Glu  Gly  Ala  Val
               965                      970                           975

Val  Ile  Gln  Asp  Asn  Ser  Asp  Ile  Lys  Val  Val  Pro  Arg  Arg  Lys  Ala
               980                 985                      990

Lys  Ile  Ile  Arg  Asp  Tyr  Gly  Lys  Gln  Met  Ala  Gly  Asp  Asp  Cys  Val
          995                 1000                     1005

Ala  Ser  Arg  Gln  Asp  Glu  Asp  Xaa
     1010                 1015
```

( 2 ) INFORMATION FOR SEQ ID NO:5:

( i ) SEQUENCE CHARACTERISTICS:
        ( A ) LENGTH: 1016 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Human immunodeficiency virus type 1
        ( B ) STRAIN: BRU ( x i ) SEQUENCE DESCRIPTION: SEQ ID NO:5:

```
Phe  Phe  Arg  Glu  Asp  Leu  Ala  Phe  Leu  Gln  Gly  Lys  Ala  Arg  Glu  Phe
1                   5                   10                       15

Ser  Ser  Glu  Gln  Thr  Arg  Ala  Asn  Ser  Pro  Thr  Ile  Ser  Ser  Glu  Gln
               20                  25                       30

Thr  Arg  Ala  Asn  Ser  Pro  Thr  Arg  Arg  Glu  Leu  Gln  Val  Trp  Gly  Arg
          35                  40                       45

Asp  Asn  Asn  Ser  Leu  Ser  Glu  Ala  Gly  Ala  Asp  Arg  Gln  Gly  Thr  Val
     50                       55                       60

Ser  Phe  Asn  Phe  Pro  Gln  Ile  Thr  Leu  Trp  Gln  Arg  Pro  Leu  Val  Thr
65                  70                       75                          80

Ile  Lys  Ile  Gly  Gly  Gln  Leu  Lys  Glu  Ala  Leu  Leu  Asp  Thr  Gly  Ala
               85                       90                            95

Asp  Asp  Thr  Val  Leu  Glu  Glu  Met  Ser  Leu  Pro  Gly  Arg  Trp  Lys  Pro
               100                 105                      110

Lys  Met  Ile  Gly  Gly  Ile  Gly  Gly  Phe  Ile  Lys  Val  Arg  Gln  Tyr  Asp
          115                 120                      125

Gln  Ile  Leu  Ile  Glu  Ile  Cys  Gly  His  Lys  Ala  Ile  Gly  Thr  Val  Leu
     130                 135                      140

Val  Gly  Pro  Thr  Pro  Val  Asn  Ile  Ile  Gly  Arg  Asn  Leu  Leu  Thr  Gln
145                 150                      155                          160

Ile  Gly  Cys  Thr  Leu  Asn  Phe  Pro  Ile  Ser  Pro  Ile  Glu  Thr  Val  Pro
               165                      170                      175

Val  Lys  Leu  Lys  Pro  Gly  Met  Asp  Gly  Pro  Lys  Val  Lys  Gln  Trp  Pro
               180                      185                      190

Leu  Thr  Glu  Glu  Lys  Ile  Lys  Ala  Leu  Val  Glu  Ile  Cys  Thr  Glu  Met
```

-continued

|   |   |   | 195 |   |   |   |   | 200 |   |   |   |   | 205 |   |
|---|---|---|---|---|---|---|---|---|---|---|---|---|---|---|
| Glu | Lys | Glu | Gly | Lys | Ile | Ser | Lys | Ile | Gly | Pro | Asn | Pro | Tyr | Asn |
|  | 210 |  |  |  |  | 215 |  |  |  |  | 220 |  |  |  |
| Thr | Pro | Val | Phe | Ala | Ile | Lys | Lys | Asp | Ser | Thr | Lys | Trp | Arg | Lys |
| 225 |  |  |  |  | 230 |  |  |  |  | 235 |  |  |  | 240 |
| Leu | Val | Asp | Phe | Arg | Glu | Leu | Asn | Lys | Arg | Thr | Gln | Asp | Phe | Trp | Glu |
|  |  |  |  | 245 |  |  |  |  | 250 |  |  |  |  | 255 |
| Val | Gln | Leu | Gly | Ile | Pro | His | Pro | Ala | Gly | Leu | Lys | Lys | Lys | Ser |
|  |  |  | 260 |  |  |  | 265 |  |  |  |  | 270 |  |  |
| Val | Thr | Val | Leu | Asp | Val | Gly | Asp | Ala | Tyr | Phe | Ser | Val | Pro | Leu | Asp |
|  |  | 275 |  |  |  |  | 280 |  |  |  |  | 285 |  |  |
| Glu | Asp | Phe | Arg | Lys | Tyr | Thr | Ala | Phe | Thr | Ile | Pro | Ser | Ile | Asn | Asn |
|  | 290 |  |  |  |  | 295 |  |  |  |  | 300 |  |  |  |
| Glu | Thr | Pro | Gly | Ile | Arg | Tyr | Gln | Tyr | Asn | Val | Leu | Pro | Gln | Gly | Trp |
| 305 |  |  |  |  | 310 |  |  |  |  | 315 |  |  |  |  | 320 |
| Lys | Gly | Ser | Pro | Ala | Ile | Phe | Gln | Ser | Ser | Met | Thr | Lys | Ile | Leu | Glu |
|  |  |  |  | 325 |  |  |  |  | 330 |  |  |  |  | 335 |
| Pro | Phe | Arg | Lys | Gln | Asn | Pro | Asp | Ile | Val | Ile | Tyr | Gln | Tyr | Met | Asp |
|  |  |  | 340 |  |  |  |  | 345 |  |  |  |  | 350 |  |
| Asp | Leu | Tyr | Val | Gly | Ser | Asp | Leu | Glu | Ile | Gly | Gln | His | Arg | Thr | Lys |
|  |  | 355 |  |  |  |  | 360 |  |  |  |  | 365 |  |  |
| Ile | Glu | Glu | Leu | Arg | Gln | His | Leu | Leu | Arg | Trp | Gly | Leu | Thr | Thr | Pro |
|  | 370 |  |  |  |  | 375 |  |  |  |  | 380 |  |  |  |
| Asp | Lys | Lys | His | Gln | Lys | Glu | Pro | Pro | Phe | Leu | Trp | Met | Gly | Tyr | Glu |
| 385 |  |  |  |  | 390 |  |  |  |  | 395 |  |  |  |  | 400 |
| Leu | His | Pro | Asp | Lys | Trp | Thr | Val | Gln | Pro | Ile | Val | Leu | Pro | Glu | Lys |
|  |  |  |  | 405 |  |  |  |  | 410 |  |  |  |  | 415 |
| Asp | Ser | Trp | Thr | Val | Asn | Asp | Ile | Gln | Lys | Leu | Val | Gly | Lys | Leu | Asn |
|  |  |  | 420 |  |  |  |  | 425 |  |  |  |  | 430 |  |
| Trp | Ala | Ser | Gln | Ile | Tyr | Pro | Gly | Ile | Lys | Val | Arg | Gln | Leu | Cys | Lys |
|  |  | 435 |  |  |  |  | 440 |  |  |  |  | 445 |  |  |
| Leu | Leu | Arg | Gly | Thr | Lys | Ala | Leu | Thr | Glu | Val | Ile | Pro | Leu | Thr | Glu |
|  | 450 |  |  |  |  | 455 |  |  |  |  | 460 |  |  |  |
| Glu | Ala | Glu | Leu | Glu | Leu | Ala | Glu | Asn | Arg | Glu | Ile | Leu | Lys | Glu | Pro |
| 465 |  |  |  |  | 470 |  |  |  |  | 475 |  |  |  |  | 480 |
| Val | His | Gly | Val | Tyr | Tyr | Asp | Pro | Ser | Lys | Asp | Leu | Ile | Ala | Glu | Ile |
|  |  |  |  | 485 |  |  |  |  | 490 |  |  |  |  | 495 |
| Gln | Lys | Gln | Gly | Gln | Gly | Gln | Trp | Thr | Tyr | Gln | Ile | Tyr | Gln | Glu | Pro |
|  |  |  | 500 |  |  |  |  | 505 |  |  |  |  | 510 |  |
| Phe | Lys | Asn | Leu | Lys | Thr | Gly | Lys | Tyr | Ala | Arg | Thr | Arg | Gly | Ala | His |
|  |  | 515 |  |  |  |  | 520 |  |  |  |  | 525 |  |  |
| Thr | Asn | Asp | Val | Lys | Gln | Leu | Thr | Glu | Ala | Val | Gln | Lys | Ile | Thr | Thr |
|  | 530 |  |  |  |  | 535 |  |  |  |  | 540 |  |  |  |
| Glu | Ser | Ile | Val | Ile | Trp | Gly | Lys | Thr | Pro | Lys | Phe | Lys | Leu | Pro | Ile |
| 545 |  |  |  |  | 550 |  |  |  |  | 555 |  |  |  |  | 560 |
| Gln | Lys | Glu | Thr | Trp | Glu | Thr | Trp | Trp | Thr | Glu | Tyr | Trp | Gln | Ala | Thr |
|  |  |  |  | 565 |  |  |  |  | 570 |  |  |  |  | 575 |
| Trp | Ile | Pro | Glu | Trp | Glu | Phe | Val | Asn | Thr | Pro | Pro | Leu | Val | Lys | Leu |
|  |  |  | 580 |  |  |  |  | 585 |  |  |  |  | 590 |  |
| Trp | Tyr | Gln | Leu | Glu | Lys | Glu | Pro | Ile | Val | Gly | Ala | Glu | Thr | Phe | Tyr |
|  |  | 595 |  |  |  |  | 600 |  |  |  |  | 605 |  |  |
| Val | Asp | Gly | Ala | Ala | Ser | Arg | Glu | Thr | Lys | Leu | Gly | Lys | Ala | Gly | Tyr |
|  | 610 |  |  |  |  | 615 |  |  |  |  | 620 |  |  |  |

-continued

| | | | | | | | | | | | | | | |
|---|---|---|---|---|---|---|---|---|---|---|---|---|---|---|
| Leu | Thr | Asn | Lys | Gly | Arg | Gln | Lys | Val | Val | Thr | Leu | Thr | Asp | Thr | Thr |
| 625 | | | | 630 | | | | | 635 | | | | | 640 | |
| Asn | Gln | Lys | Thr | Glu | Leu | Gln | Ala | Ile | His | Leu | Ala | Leu | Gln | Asp | Ser |
| | | | 645 | | | | | 650 | | | | | 655 | | |
| Gly | Leu | Glu | Val | Asn | Ile | Val | Thr | Asp | Ser | Gln | Tyr | Ala | Leu | Gly | Ile |
| | | | 660 | | | | | 665 | | | | | 670 | | |
| Ile | Gln | Ala | Gln | Pro | Asp | Lys | Ser | Glu | Ser | Glu | Leu | Val | Asn | Gln | Ile |
| | | 675 | | | | | 680 | | | | | 685 | | | |
| Ile | Glu | Gln | Leu | Ile | Lys | Lys | Glu | Lys | Val | Tyr | Leu | Ala | Trp | Val | Pro |
| | | 690 | | | | 695 | | | | | 700 | | | | |
| Ala | His | Lys | Gly | Ile | Gly | Gly | Asn | Glu | Gln | Val | Asp | Lys | Leu | Val | Ser |
| 705 | | | | | 710 | | | | 715 | | | | | 720 | |
| Ala | Gly | Ile | Arg | Lys | Ile | Leu | Phe | Leu | Asp | Gly | Ile | Asp | Lys | Ala | Gln |
| | | | 725 | | | | | 730 | | | | | 735 | | |
| Asp | Glu | His | Glu | Lys | Tyr | His | Ser | Asn | Trp | Arg | Ala | Met | Ala | Ser | Asp |
| | | | 740 | | | | | 745 | | | | | 750 | | |
| Phe | Asn | Leu | Pro | Pro | Val | Val | Ala | Lys | Glu | Ile | Val | Ala | Ser | Cys | Asp |
| | | 755 | | | | | 760 | | | | | 765 | | | |
| Lys | Cys | Gln | Leu | Lys | Gly | Glu | Ala | Met | His | Gly | Gln | Val | Asp | Cys | Ser |
| | 770 | | | | | 775 | | | | | 780 | | | | |
| Pro | Gly | Ile | Trp | Gln | Leu | Asp | Cys | Thr | His | Leu | Glu | Gly | Lys | Val | Ile |
| 785 | | | | | 790 | | | | 795 | | | | | 800 | |
| Leu | Val | Ala | Val | His | Val | Ala | Ser | Gly | Tyr | Ile | Glu | Ala | Glu | Val | Ile |
| | | | | 805 | | | | 810 | | | | | 815 | | |
| Pro | Ala | Glu | Thr | Gly | Gln | Glu | Thr | Ala | Tyr | Phe | Leu | Leu | Lys | Leu | Ala |
| | | | 820 | | | | 825 | | | | | 830 | | | |
| Gly | Arg | Trp | Pro | Val | Lys | Thr | Ile | His | Thr | Asp | Asn | Gly | Ser | Asn | Phe |
| | | 835 | | | | | 840 | | | | | 845 | | | |
| Thr | Ser | Thr | Thr | Val | Lys | Ala | Ala | Cys | Trp | Trp | Ala | Gly | Ile | Lys | Gln |
| | 850 | | | | | 855 | | | | | 860 | | | | |
| Glu | Phe | Gly | Ile | Pro | Tyr | Asn | Pro | Gln | Ser | Gln | Gly | Val | Val | Glu | Ser |
| 865 | | | | | 870 | | | | 875 | | | | | 880 | |
| Met | Asn | Lys | Glu | Leu | Lys | Lys | Ile | Ile | Gly | Gln | Val | Arg | Asp | Gln | Ala |
| | | | | 885 | | | | 890 | | | | | 895 | | |
| Glu | His | Leu | Lys | Thr | Ala | Val | Gln | Met | Ala | Val | Phe | Ile | His | Asn | Phe |
| | | | 900 | | | | 905 | | | | | 910 | | | |
| Lys | Arg | Lys | Gly | Gly | Ile | Gly | Gly | Tyr | Ser | Ala | Gly | Glu | Arg | Ile | Val |
| | | 915 | | | | | 920 | | | | | 925 | | | |
| Asp | Ile | Ile | Ala | Thr | Asp | Ile | Gln | Thr | Lys | Glu | Leu | Gln | Lys | Gln | Ile |
| | 930 | | | | | 935 | | | | | 940 | | | | |
| Thr | Lys | Ile | Gln | Asn | Phe | Arg | Val | Tyr | Tyr | Arg | Asp | Ser | Arg | Asp | Pro |
| 945 | | | | | 950 | | | | 955 | | | | | 960 | |
| Leu | Trp | Lys | Gly | Pro | Ala | Lys | Leu | Leu | Trp | Lys | Gly | Glu | Gly | Ala | Val |
| | | | | 965 | | | | 970 | | | | | 975 | | |
| Val | Ile | Gln | Asp | Asn | Ser | Asp | Ile | Lys | Val | Val | Pro | Arg | Arg | Lys | Ala |
| | | | 980 | | | | 985 | | | | | 990 | | | |
| Lys | Ile | Ile | Arg | Asp | Tyr | Gly | Lys | Gln | Met | Ala | Gly | Asp | Asp | Cys | Val |
| | | 995 | | | | 1000 | | | | | 1005 | | | | |
| Ala | Ser | Arg | Gln | Asp | Glu | Asp | Xaa | | | | | | | | |
| 1010 | | | | | 1015 | | | | | | | | | | |

( 2 ) INFORMATION FOR SEQ ID NO:6:

( i ) SEQUENCE CHARACTERISTICS:
( A ) LENGTH: 913 amino acids ( B ) TYPE: amino acid
( C ) STRANDEDNESS: Not Relevant
( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
( A ) ORGANISM: Human immunodeficiency virus type 1
( B ) STRAIN: MN ( x i ) SEQUENCE DESCRIPTION: SEQ ID NO:6:

| Met | Asn | Leu | Pro | Arg | Arg | Trp | Lys | Pro | Met | Ile | Gly | Gly | Ile | Gly |
|---|---|---|---|---|---|---|---|---|---|---|---|---|---|---|
| 1 | | | | 5 | | | | | 10 | | | | | 15 |
| Gly | Phe | Ile | Lys | Val | Arg | Gln | Tyr | Asp | Gln | Ile | Thr | Ile | Gly | Ile | Cys |
| | | | 20 | | | | 25 | | | | | 30 | | |
| Gly | His | Lys | Ala | Ile | Gly | Thr | Val | Leu | Val | Gly | Pro | Thr | Pro | Val | Asn |
| | | 35 | | | | 40 | | | | | 45 | | | |
| Ile | Ile | Gly | Arg | Asn | Leu | Leu | Thr | Gln | Leu | Gly | Cys | Thr | Leu | Asn | Phe |
| | 50 | | | | | 55 | | | | | 60 | | | |
| Pro | Ile | Ser | Pro | Ile | Glu | Thr | Val | Pro | Val | Lys | Leu | Lys | Pro | Gly | Met |
| 65 | | | | | 70 | | | | | 75 | | | | | 80 |
| Asp | Gly | Pro | Lys | Val | Lys | Gln | Trp | Pro | Leu | Thr | Glu | Glu | Lys | Ile | Lys |
| | | | | 85 | | | | | 90 | | | | | 95 |
| Ala | Leu | Ile | Glu | Ile | Cys | Thr | Glu | Met | Glu | Lys | Glu | Gly | Lys | Ile | Ser |
| | | | | 100 | | | | | 105 | | | | | 110 | |
| Lys | Ile | Gly | Pro | Glu | Asn | Pro | Tyr | Asn | Thr | Pro | Val | Phe | Ala | Ile | Lys |
| | | | 115 | | | | | 120 | | | | | 125 | | |
| Lys | Lys | Asp | Ser | Thr | Lys | Trp | Arg | Lys | Leu | Val | Asp | Phe | Arg | Glu | Leu |
| | | 130 | | | | | 135 | | | | | 140 | | | |
| Asn | Lys | Lys | Thr | Gln | Asp | Phe | Trp | Glu | Val | Gln | Leu | Gly | Ile | Pro | His |
| 145 | | | | | 150 | | | | | 155 | | | | | 160 |
| Pro | Ala | Gly | Leu | Lys | Lys | Lys | Lys | Ser | Val | Thr | Val | Leu | Asp | Val | Gly |
| | | | | 165 | | | | | 170 | | | | | 175 | |
| Asp | Ala | Tyr | Phe | Ser | Val | Pro | Leu | Asp | Lys | Asp | Phe | Arg | Lys | Tyr | Thr |
| | | | 180 | | | | | 185 | | | | | 190 | | |
| Ala | Phe | Thr | Ile | Pro | Ser | Ile | Asn | Asn | Glu | Thr | Pro | Gly | Ile | Arg | Tyr |
| | | 195 | | | | | 200 | | | | | 205 | | | |
| Gln | Tyr | Asn | Val | Leu | Pro | Gln | Gly | Trp | Lys | Gly | Ser | Pro | Ala | Ile | Phe |
| | 210 | | | | | 215 | | | | | 220 | | | | |
| Gln | Ser | Ser | Met | Thr | Lys | Ile | Leu | Glu | Pro | Phe | Arg | Lys | Gln | Asn | Pro |
| 225 | | | | | 230 | | | | | 235 | | | | | 240 |
| Asp | Ile | Val | Ile | Tyr | Gln | Tyr | Met | Asp | Asp | Leu | Tyr | Val | Gly | Ser | Asp |
| | | | | 245 | | | | | 250 | | | | | 255 | |
| Leu | Glu | Ile | Gly | Gln | His | Arg | Ala | Lys | Ile | Glu | Glu | Leu | Arg | Arg | His |
| | | | 260 | | | | | 265 | | | | | 270 | | |
| Leu | Leu | Arg | Trp | Gly | Phe | Thr | Thr | Pro | Asp | Lys | Lys | His | Gln | Lys | Glu |
| | | 275 | | | | | 280 | | | | | 285 | | | |
| Pro | Pro | Phe | Leu | Trp | Met | Gly | Tyr | Glu | Leu | His | Pro | Asp | Lys | Trp | Thr |
| | 290 | | | | | 295 | | | | | 300 | | | | |
| Val | Gln | Pro | Ile | Val | Leu | Pro | Glu | Lys | Asp | Ser | Trp | Thr | Val | Asn | Asp |
| 305 | | | | | 310 | | | | | 315 | | | | | 320 |
| Ile | Gln | Lys | Leu | Val | Gly | Lys | Leu | Asn | Trp | Ala | Ser | Gln | Ile | Tyr | Ala |
| | | | | 325 | | | | | 330 | | | | | 335 | |
| Gly | Ile | Lys | Val | Lys | Gln | Leu | Cys | Lys | Leu | Leu | Arg | Gly | Thr | Lys | Ala |

-continued

```
                                  340                      345                      350
        Leu Thr Glu Val Ile Pro Leu Thr Glu Glu Ala Glu Leu Glu Leu Ala
                355                      360                      365
        Glu Asn Arg Glu Ile Leu Lys Glu Pro Val His Gly Val Tyr Tyr Asp
                370                      375                      380
        Pro Ser Lys Asp Leu Ile Ala Glu Val Gln Lys Gln Gly Gln Gly Gln
        385                      390                      395                      400
        Trp Thr Tyr Gln Ile Tyr Gln Glu Pro Phe Lys Asn Leu Lys Thr Gly
                                 405                      410                      415
        Lys Tyr Ala Arg Met Arg Gly Ala His Thr Asn Asp Val Lys Gln Leu
                         420                      425                      430
        Thr Glu Ala Val Gln Lys Ile Ala Thr Glu Ser Ile Val Ile Trp Gly
                    435                      440                      445
        Lys Thr Pro Lys Phe Arg Leu Pro Ile Gln Lys Glu Thr Trp Glu Thr
                450                      455                      460
        Trp Trp Thr Glu Tyr Thr Xaa Ala Thr Trp Ile Pro Glu Trp Glu Val
        465                      470                      475                      480
        Val Asn Thr Pro Pro Leu Val Lys Leu Trp Tyr Gln Leu Glu Lys Glu
                                 485                      490                      495
        Pro Ile Val Gly Ala Glu Thr Phe Tyr Val Asp Gly Ala Ala Ser Arg
                         500                      505                      510
        Glu Thr Lys Lys Gly Lys Ala Gly Tyr Leu Thr Asn Lys Gly Arg Gln
                    515                      520                      525
        Lys Val Val Ser Leu Thr Asp Thr Thr Asn Gln Lys Thr Glu Leu Gln
                530                      535                      540
        Ala Ile His Leu Ala Leu Gln Asp Ser Gly Leu Glu Val Asn Ile Val
        545                      550                      555                      560
        Thr Asp Ser Gln Tyr Ala Leu Gly Ile Ile Gln Ala Gln Pro Asp Lys
                                 565                      570                      575
        Ser Glu Ser Glu Leu Val Ser Gln Ile Ile Glu Gln Leu Ile Lys Lys
                         580                      585                      590
        Glu Lys Val Tyr Leu Ala Trp Val Pro Ala His Lys Gly Ile Gly Gly
                    595                      600                      605
        Asn Glu Gln Val Asp Lys Leu Val Ser Ala Gly Ile Arg Lys Ile Leu
                610                      615                      620
        Phe Leu Asp Gly Ile Asp Lys Ala Gln Glu Asp His Glu Lys Tyr His
        625                      630                      635                      640
        Ser Asn Trp Arg Ala Met Ala Ser Asp Phe Asn Leu Pro Pro Ile Val
                                 645                      650                      655
        Ala Lys Glu Ile Val Ala Ser Cys Asp Lys Cys Gln Leu Lys Gly Glu
                         660                      665                      670
        Ala Met His Gly Gln Val Asp Cys Ser Pro Gly Ile Trp Gln Leu Asp
                    675                      680                      685
        Cys Thr His Leu Glu Gly Lys Val Ile Leu Val Ala Val His Val Ala
                690                      695                      700
        Ser Gly Tyr Ile Glu Ala Glu Val Ile Pro Ala Glu Thr Gly Gln Glu
        705                      710                      715                      720
        Thr Ala Tyr Phe Leu Leu Lys Leu Ala Gly Arg Trp Pro Val Lys Thr
                                 725                      730                      735
        Ile His Thr Asp Asn Gly Pro Asn Phe Thr Ser Thr Thr Val Lys Ala
                         740                      745                      750
        Ala Cys Trp Trp Thr Gly Ile Lys Gln Glu Phe Gly Ile Pro Tyr Asn
                    755                      760                      765
```

| | | | | | | | | | | | | | | |
|---|---|---|---|---|---|---|---|---|---|---|---|---|---|---|
|Pro|Gln|Ser|Gln|Gly|Val|Ile|Glu|Ser|Met|Asn|Lys|Glu|Leu|Lys|Lys|
| |770| | | |775| | | |780| | | | | |
|Ile|Ile|Gly|Gln|Val|Arg|Asp|Gln|Ala|Glu|His|Leu|Lys|Arg|Ala|Val|
|785| | | | |790| | | |795| | | | | |800|
|Gln|Met|Ala|Val|Phe|Ile|His|Asn|Phe|Lys|Arg|Lys|Gly|Gly|Ile|Gly|
| | | | |805| | | | |810| | | | |815| |
|Gly|Tyr|Ser|Ala|Gly|Glu|Arg|Ile|Val|Gly|Ile|Ile|Ala|Thr|Asp|Ile|
| | | |820| | | |825| | | | |830| | | |
|Gln|Thr|Lys|Glu|Leu|Gln|Lys|Gln|Ile|Thr|Lys|Ile|Gln|Asn|Phe|Arg|
| | |835| | | |840| | | | |845| | | | |
|Val|Tyr|Tyr|Arg|Asp|Ser|Arg|Asp|Pro|Leu|Trp|Lys|Gly|Pro|Ala|Lys|
| |850| | | |855| | | | |860| | | | | |
|Leu|Leu|Trp|Lys|Gly|Glu|Gly|Ala|Val|Val|Ile|Gln|Asp|Asn|Asn|Asp|
|865| | | | |870| | | | |875| | | | |880|
|Ile|Lys|Val|Val|Pro|Arg|Arg|Lys|Ala|Lys|Val|Ile|Arg|Asp|Tyr|Gly|
| | | | |885| | | | |890| | | | |895| |
|Lys|Gln|Thr|Ala|Gly|Asp|Asp|Cys|Val|Ala|Ser|Arg|Gln|Asp|Glu|Asp|
| | | |900| | | |905| | | | |910| | | |
|Xaa| | | | | | | | | | | | | | | |

( 2 ) INFORMATION FOR SEQ ID NO:7:

( i ) SEQUENCE CHARACTERISTICS:
  ( A ) LENGTH: 1004 amino acids
  ( B ) TYPE: amino acid
  ( C ) STRANDEDNESS: Not Relevant
  ( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
  ( A ) ORGANISM: Human immunodeficiency virus type 1
  ( B ) STRAIN: SF2

( x i ) SEQUENCE DESCRIPTION: SEQ ID NO:7:

| | | | | | | | | | | | | | | | |
|---|---|---|---|---|---|---|---|---|---|---|---|---|---|---|---|
|Phe|Phe|Arg|Glu|Asp|Leu|Ala|Phe|Leu|Gln|Gly|Lys|Ala|Arg|Glu|Phe|
|1| | | |5| | | | |10| | | | |15| |
|Ser|Ser|Glu|Gln|Thr|Arg|Ala|Asn|Ser|Pro|Thr|Arg|Arg|Glu|Leu|Gln|
| | | |20| | | | |25| | | | |30| | |
|Val|Trp|Gly|Gly|Glu|Asn|Asn|Ser|Leu|Ser|Glu|Ala|Gly|Ala|Asp|Arg|
| | |35| | | | |40| | | | |45| | | |
|Gln|Gly|Thr|Val|Ser|Phe|Asn|Phe|Pro|Gln|Ile|Thr|Leu|Trp|Gln|Arg|
| |50| | | | |55| | | | |60| | | | |
|Pro|Leu|Val|Thr|Ile|Arg|Ile|Gly|Gly|Gln|Leu|Lys|Glu|Ala|Leu|Leu|
|65| | | | |70| | | | |75| | | | |80|
|Asp|Thr|Gly|Ala|Asp|Asp|Thr|Val|Leu|Glu|Glu|Met|Asn|Leu|Pro|Gly|
| | | | |85| | | | |90| | | | |95| |
|Lys|Trp|Lys|Pro|Lys|Met|Ile|Gly|Gly|Ile|Gly|Gly|Phe|Ile|Lys|Val|
| | | |100| | | | |105| | | | |110| | |
|Arg|Gln|Tyr|Asp|Gln|Ile|Pro|Val|Glu|Ile|Cys|Gly|His|Lys|Ala|Ile|
| | |115| | | | |120| | | | |125| | | |
|Gly|Thr|Val|Leu|Val|Gly|Pro|Thr|Pro|Val|Asn|Ile|Ile|Gly|Arg|Asn|
| |130| | | | |135| | | | |140| | | | |
|Leu|Leu|Thr|Gln|Ile|Gly|Cys|Thr|Leu|Asn|Phe|Pro|Ile|Ser|Pro|Ile|
|145| | | | |150| | | | |155| | | | |160|

| | | | | | | | | | | | | | | |
|---|---|---|---|---|---|---|---|---|---|---|---|---|---|---|
|Glu|Thr|Val|Pro|Val 165|Lys|Leu|Lys|Pro|Gly 170|Met|Asp|Gly|Pro|Lys Val 175|
|Lys|Gln|Trp|Pro 180|Leu|Thr|Glu|Glu|Lys 185|Ile|Lys|Ala|Leu|Val 190|Glu Ile|
|Cys|Thr|Glu 195|Met|Glu|Lys|Glu|Gly 200|Lys|Ile|Ser|Lys|Ile 205|Gly|Pro Glu|
|Asn|Pro 210|Tyr|Asn|Thr|Pro 215|Val|Phe|Ala|Ile|Lys|Lys 220|Lys|Asp|Ser Thr|
|Lys 225|Trp|Arg|Lys|Leu 230|Val|Asp|Phe|Arg|Glu 235|Leu|Asn|Lys|Arg|Thr Gln 240|
|Asp|Phe|Trp|Glu|Val 245|Gln|Leu|Gly|Ile|Pro 250|His|Pro|Ala|Gly|Leu Lys 255|
|Lys|Lys|Lys|Ser 260|Val|Thr|Val|Leu|Asp 265|Val|Gly|Asp|Ala|Tyr 270|Phe Ser|
|Val|Pro|Leu|Asp 275|Lys|Asp|Phe|Arg|Lys 280|Tyr|Thr|Ala|Phe|Thr 285|Ile Pro|
|Ser|Ile|Asn 290|Asn|Glu|Thr|Pro|Gly 295|Ile|Arg|Tyr|Gln|Tyr 300|Asn|Val Leu|
|Pro 305|Gln|Gly|Trp|Lys|Gly 310|Ser|Pro|Ala|Ile|Phe 315|Gln|Ser|Ser|Met Thr 320|
|Lys|Ile|Leu|Glu|Pro 325|Phe|Arg|Lys|Gln|Asn 330|Pro|Asp|Ile|Val|Ile Tyr 335|
|Gln|Tyr|Met|Asp 340|Asp|Leu|Tyr|Val|Gly 345|Ser|Asp|Leu|Glu|Ile 350|Gly Gln|
|His|Arg|Thr 355|Lys|Ile|Glu|Glu|Leu 360|Arg|Gln|His|Leu|Leu 365|Arg|Trp Gly|
|Phe|Thr|Thr 370|Pro|Asp|Lys|Lys 375|His|Gln|Lys|Glu|Pro 380|Pro|Phe|Leu Trp|
|Met 385|Gly|Tyr|Glu|Leu|His 390|Pro|Asp|Lys|Trp|Thr 395|Val|Gln|Pro|Ile Met 400|
|Leu|Pro|Glu|Lys|Asp 405|Ser|Trp|Thr|Val|Asn 410|Asp|Ile|Gln|Lys|Leu Val 415|
|Gly|Lys|Leu|Asn 420|Trp|Ala|Ser|Gln|Ile 425|Tyr|Ala|Gly|Ile|Lys 430|Val Lys|
|Gln|Leu|Cys 435|Lys|Leu|Leu|Arg|Gly 440|Thr|Lys|Ala|Leu|Thr 445|Glu|Val Ile|
|Pro|Leu 450|Thr|Glu|Glu|Ala|Glu 455|Leu|Glu|Leu|Ala|Glu 460|Asn|Arg|Glu Ile|
|Leu 465|Lys|Glu|Pro|Val|His 470|Glu|Val|Tyr|Tyr|Asp 475|Pro|Ser|Lys|Asp Leu 480|
|Val|Ala|Glu|Ile|Gln 485|Lys|Gln|Gly|Gln 490|Gly|Gln|Trp|Thr|Tyr|Gln Ile 495|
|Tyr|Gln|Glu|Pro 500|Phe|Lys|Asn|Leu|Lys 505|Thr|Gly|Lys|Tyr|Ala 510|Arg Met|
|Arg|Gly|Ala 515|His|Thr|Asn|Asp|Val 520|Lys|Gln|Leu|Thr|Glu 525|Ala|Val Gln|
|Lys|Val 530|Ser|Thr|Glu|Ser|Ile 535|Val|Ile|Trp|Gly|Lys 540|Ile|Pro|Lys Phe|
|Lys 545|Leu|Pro|Ile|Gln|Lys 550|Glu|Thr|Trp|Glu|Ala 555|Trp|Trp|Met|Glu Tyr 560|
|Trp|Gln|Ala|Thr|Trp 565|Ile|Pro|Glu|Trp|Glu 570|Phe|Val|Asn|Thr|Pro Pro 575|
|Leu|Val|Lys|Leu 580|Trp|Tyr|Gln|Leu|Glu 585|Lys|Glu|Pro|Ile|Val 590|Gly Ala|

| | | | | | | | | | | | | | | |
|---|---|---|---|---|---|---|---|---|---|---|---|---|---|---|
| Glu | Thr | Phe 595 | Tyr | Val | Asp | Gly | Ala 600 | Ala | Asn | Arg | Glu | Thr 605 | Lys | Leu | Gly |
| Lys | Ala 610 | Gly | Tyr | Val | Thr 615 | Asp | Arg | Gly | Arg | Gln 620 | Lys | Val | Val | Ser | Ile |
| Ala 625 | Asp | Thr | Thr | Asn | Gln 630 | Lys | Thr | Glu | Leu | Gln 635 | Ala | Ile | His | Leu | Ala 640 |
| Leu | Gln | Asp | Ser | Gly 645 | Leu | Glu | Val | Asn | Ile 650 | Val | Thr | Asp | Ser | Gln 655 | Tyr |
| Ala | Leu | Gly | Ile 660 | Ile | Gln | Ala | Gln | Pro 665 | Asp | Lys | Ser | Glu | Ser 670 | Glu | Leu |
| Val | Ser | Gln 675 | Ile | Ile | Glu | Gln | Leu 680 | Ile | Lys | Lys | Glu | Lys 685 | Val | Tyr | Leu |
| Ala | Trp 690 | Val | Pro | Ala | His 695 | Lys | Gly | Ile | Gly | Gly 700 | Asn | Glu | Gln | Val | Asp |
| Lys 705 | Leu | Val | Ser | Ala | Gly 710 | Ile | Arg | Lys | Val | Leu 715 | Phe | Leu | Asn | Gly | Ile 720 |
| Asp | Lys | Ala | Gln | Glu 725 | Glu | His | Glu | Lys | Tyr 730 | His | Ser | Asn | Trp | Arg 735 | Ala |
| Met | Ala | Ser | Asp 740 | Phe | Asn | Leu | Pro | Pro 745 | Val | Val | Ala | Lys | Glu 750 | Ile | Val |
| Ala | Ser | Cys 755 | Asp | Lys | Cys | Gln | Leu 760 | Lys | Gly | Glu | Ala | Met 765 | His | Gly | Gln |
| Val | Asp | Cys 770 | Ser | Pro | Gly | Ile | Trp 775 | Gln | Leu | Asp | Cys | Thr 780 | His | Leu | Glu |
| Gly 785 | Lys | Ile | Ile | Leu | Val 790 | Ala | Val | His | Val | Ala 795 | Ser | Gly | Tyr | Ile | Glu 800 |
| Ala | Glu | Val | Ile | Pro 805 | Ala | Glu | Thr | Gly | Gln 810 | Glu | Thr | Ala | Tyr | Phe 815 | Leu |
| Leu | Lys | Leu | Ala 820 | Gly | Arg | Trp | Pro | Val 825 | Lys | Thr | Ile | His | Thr 830 | Asp | Asn |
| Gly | Ser | Asn 835 | Phe | Thr | Ser | Thr | Thr 840 | Val | Lys | Ala | Ala | Cys 845 | Trp | Trp | Ala |
| Gly | Ile 850 | Lys | Gln | Glu | Phe | Gly 855 | Ile | Pro | Tyr | Asn | Pro 860 | Gln | Ser | Gln | Gly |
| Val 865 | Val | Glu | Ser | Met | Asn 870 | Asn | Glu | Leu | Lys | Lys 875 | Ile | Ile | Gly | Gln | Val 880 |
| Arg | Asp | Gln | Ala | Glu 885 | His | Leu | Lys | Thr | Ala 890 | Val | Gln | Met | Ala | Val 895 | Phe |
| Ile | His | Asn | Phe 900 | Lys | Arg | Lys | Gly | Gly 905 | Ile | Gly | Gly | Tyr | Ser 910 | Ala | Gly |
| Glu | Arg | Ile 915 | Val | Asp | Ile | Ile | Ala 920 | Thr | Asp | Ile | Gln | Thr 925 | Lys | Glu | Leu |
| Gln | Lys | Gln 930 | Ile | Thr | Lys | Ile 935 | Gln | Asn | Phe | Arg | Val 940 | Tyr | Tyr | Arg | Asp |
| Asn 945 | Lys | Asp | Pro | Leu | Trp 950 | Lys | Gly | Pro | Ala | Lys 955 | Leu | Leu | Trp | Lys | Gly 960 |
| Glu | Gly | Ala | Val | Val 965 | Ile | Gln | Asp | Asn | Ser 970 | Asp | Ile | Lys | Val | Val 975 | Pro |
| Arg | Arg | Lys | Ala 980 | Lys | Ile | Ile | Arg | Asp 985 | Tyr | Gly | Lys | Gln | Met 990 | Ala | Gly |
| Asp | Asp | Cys 995 | Val | Ala | Ser | Arg | Gln 1000 | Asp | Glu | Asp | Xaa | | | | |

( 2 ) INFORMATION FOR SEQ ID NO:8:

( i ) SEQUENCE CHARACTERISTICS:
        ( A ) LENGTH: 1003 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Human immunodeficiency virus type 1
        ( B ) STRAIN: RF ( x i ) SEQUENCE DESCRIPTION: SEQ ID NO:8:

```
Phe  Phe  Arg  Glu  Asn  Leu  Ala  Phe  Pro  Gln  Gly  Lys  Ala  Arg  Glu  Leu
 1              5                        10                       15

Ser  Ser  Glu  Gln  Thr  Arg  Ala  Asn  Ser  Pro  Thr  Arg  Arg  Glu  Leu  Gln
              20                        25                       30

Val  Trp  Gly  Arg  Asp  Asn  Ser  Leu  Ser  Glu  Ala  Gly  Glu  Asp  Arg  Gln
              35                        40                       45

Gly  Thr  Val  Ser  Phe  Ser  Phe  Pro  Gln  Ile  Thr  Leu  Trp  Gln  Arg  Pro
         50                   55                       60

Ile  Val  Thr  Val  Lys  Ile  Gly  Gly  Gln  Leu  Lys  Glu  Ala  Leu  Leu  Asp
 65                        70                       75                     80

Thr  Gly  Ala  Asp  Asp  Thr  Val  Leu  Glu  Glu  Met  Asn  Leu  Pro  Gly  Lys
                   85                        90                            95

Trp  Lys  Pro  Lys  Met  Ile  Gly  Gly  Ile  Gly  Gly  Phe  Ile  Lys  Val  Arg
              100                      105                      110

Gln  Tyr  Asp  Gln  Ile  Leu  Ile  Glu  Ile  Cys  Gly  His  Lys  Ala  Ile  Gly
              115                      120                      125

Thr  Val  Leu  Val  Gly  Pro  Thr  Pro  Val  Asn  Ile  Ile  Gly  Arg  Asn  Leu
         130                  135                       140

Leu  Thr  Gln  Ile  Gly  Cys  Thr  Leu  Asn  Phe  Pro  Ile  Ser  Pro  Ile  Glu
145                      150                      155                     160

Thr  Val  Pro  Val  Lys  Leu  Lys  Pro  Gly  Met  Asp  Gly  Pro  Lys  Val  Lys
                   165                       170                      175

Gln  Trp  Pro  Leu  Thr  Glu  Glu  Lys  Ile  Lys  Ala  Leu  Val  Glu  Ile  Cys
              180                      185                      190

Thr  Glu  Met  Glu  Lys  Glu  Gly  Lys  Ile  Ser  Lys  Ile  Gly  Pro  Glu  Asn
              195                      200                      205

Pro  Tyr  Asn  Thr  Pro  Val  Phe  Ala  Ile  Lys  Lys  Lys  Asp  Ser  Thr  Lys
         210                  215                       220

Trp  Arg  Lys  Leu  Val  Asp  Phe  Arg  Glu  Leu  Asn  Lys  Arg  Thr  Gln  Asp
225                      230                      235                     240

Phe  Trp  Glu  Val  Gln  Leu  Gly  Ile  Pro  His  Pro  Ala  Gly  Leu  Lys  Lys
                   245                       250                      255

Lys  Lys  Ser  Val  Thr  Val  Leu  Asp  Val  Gly  Asp  Ala  Tyr  Phe  Ser  Val
              260                      265                      270

Pro  Leu  Asp  Lys  Glu  Phe  Arg  Lys  Tyr  Thr  Ala  Phe  Thr  Ile  Pro  Ser
              275                      280                      285

Ile  Asn  Asn  Glu  Thr  Pro  Arg  Ile  Arg  Tyr  Gln  Tyr  Asn  Val  Leu  Pro
         290                  295                       300

Gln  Gly  Trp  Lys  Gly  Ser  Pro  Ala  Ile  Phe  Gln  Ser  Ser  Met  Thr  Lys
305                      310                      315                     320
```

```
Ile Leu Glu Pro Phe Lys Lys Gln Asn Pro Glu Ile Val Ile Tyr Gln
            325                 330                 335
Tyr Met Asp Asp Leu Tyr Val Gly Ser Asp Leu Glu Ile Gly Gln His
            340                 345                 350
Arg Ile Lys Ile Glu Glu Leu Arg Glu His Leu Leu Lys Trp Gly Phe
            355                 360                 365
Thr Thr Pro Asp Lys Lys His Gln Lys Glu Pro Pro Phe Leu Trp Met
            370                 375                 380
Gly Tyr Glu Leu His Pro Asp Lys Trp Thr Val Gln Pro Ile Val Leu
385                 390                 395                 400
Pro Glu Lys Asp Ser Trp Thr Val Asn Asp Ile Gln Lys Leu Val Gly
                405                 410                 415
Lys Leu Asn Trp Ala Ser Gln Ile Tyr Ala Gly Ile Lys Val Lys Gln
            420                 425                 430
Leu Cys Lys Leu Leu Arg Gly Thr Lys Ala Leu Thr Glu Val Val Gln
            435                 440                 445
Leu Thr Lys Glu Ala Glu Leu Glu Leu Ala Glu Asn Arg Glu Ile Leu
    450                 455                 460
Lys Glu Pro Val His Gly Val Tyr Tyr Asp Pro Ser Lys Asp Leu Ile
465                 470                 475                 480
Ala Glu Ile Gln Lys Gln Gly Gln Gly Gln Trp Thr Tyr Gln Ile Tyr
                485                 490                 495
Gln Glu Pro Phe Lys Asn Leu Lys Thr Gly Lys Tyr Ala Arg Met Arg
            500                 505                 510
Gly Ala His Thr Asn Asp Val Lys Gln Leu Thr Glu Ala Val Gln Lys
        515                 520                 525
Val Ala Thr Glu Ser Ile Val Ile Trp Gly Lys Thr Pro Lys Phe Lys
    530                 535                 540
Leu Pro Ile Gln Lys Glu Thr Trp Glu Ala Trp Trp Thr Glu Tyr Trp
545                 550                 555                 560
Gln Ala Thr Trp Ile Pro Glu Trp Glu Phe Val Asn Thr Pro Pro Leu
                565                 570                 575
Val Lys Leu Trp Tyr Gln Leu Glu Lys Glu Pro Ile Ile Gly Ala Glu
            580                 585                 590
Thr Phe Tyr Val Asp Gly Ala Ala Asn Arg Glu Thr Lys Leu Gly Lys
        595                 600                 605
Ala Gly Tyr Val Thr Asp Arg Gly Arg Gln Lys Val Val Ser Leu Thr
    610                 615                 620
Asp Thr Thr Asn Gln Lys Thr Glu Leu Gln Ala Ile His Leu Ala Leu
625                 630                 635                 640
Gln Asp Ser Gly Leu Glu Val Asn Ile Val Thr Asp Ser Gln Tyr Ala
                645                 650                 655
Leu Gly Ile Ile Gln Ala Gln Pro Asp Lys Ser Glu Ser Glu Leu Val
            660                 665                 670
Ser Gln Ile Ile Glu Gln Leu Ile Lys Lys Glu Lys Val Tyr Leu Ala
        675                 680                 685
Trp Val Pro Ala His Lys Gly Ile Gly Gly Asn Glu Gln Val Asp Arg
    690                 695                 700
Leu Val Ser Thr Gly Ile Arg Lys Val Leu Phe Leu Asp Gly Ile Asp
705                 710                 715                 720
Lys Ala Gln Asp Glu His Glu Lys Tyr His Ser Asn Trp Arg Ala Met
                725                 730                 735
Ala Ser Asp Phe Asn Leu Pro Pro Val Val Ala Lys Glu Ile Val Ala
            740                 745                 750
```

Ser Cys Asp Lys Cys Gln Leu Lys Gly Glu Ala Met His Gly Gln Val
    755             760                 765

Asp Cys Ser Pro Gly Ile Trp Gln Leu Asp Cys Thr His Leu Glu Gly
770             775                 780

Lys Ile Ile Leu Val Ala Val His Val Ala Ser Gly Tyr Ile Glu Ala
785             790             795                         800

Glu Val Ile Pro Ala Glu Thr Gly Gln Glu Thr Ala Tyr Phe Ile Leu
            805                 810                     815

Lys Leu Ala Gly Arg Trp Pro Val Lys Val Ile His Thr Asp Asn Gly
            820             825                     830

Ser Asn Phe Thr Ser Thr Val Lys Ala Ala Cys Trp Trp Ala Gly
        835             840             845

Ile Lys Gln Glu Phe Gly Ile Pro Tyr Asn Pro Gln Ser Gln Gly Val
    850             855                 860

Val Glu Ser Met Asn Lys Gln Leu Lys Gln Ile Ile Gly Gln Val Arg
865             870             875                         880

Asp Gln Ala Glu His Leu Lys Thr Ala Val Gln Met Ala Val Phe Ile
                885             890                     895

His Asn Phe Lys Arg Lys Gly Gly Ile Gly Gly Tyr Ser Ala Gly Glu
            900             905                 910

Arg Ile Val Asp Ile Ile Ala Thr Asp Ile Gln Thr Lys Glu Leu Gln
        915             920                 925

Lys Gln Ile Thr Lys Ile Gln Asn Phe Arg Val Tyr Tyr Arg Asp Ser
    930             935                 940

Arg Asp Pro Leu Trp Lys Gly His Ala Lys Leu Leu Trp Lys Gly Glu
945             950             955                         960

Gly Ala Val Val Ile Gln Asp Asn Ser Asp Ile Lys Val Val Pro Arg
            965                 970                 975

Arg Lys Ala Lys Ile Ile Arg Asp Tyr Gly Lys Gln Met Ala Gly Asp
        980             985                     990

Asp Cys Val Ala Ser Arg Gln Asp Glu Asp Xaa
        995             1000

( 2 ) INFORMATION FOR SEQ ID NO:9:

( i ) SEQUENCE CHARACTERISTICS:
      ( A ) LENGTH: 1003 amino acids
      ( B ) TYPE: amino acid
      ( C ) STRANDEDNESS: Not Relevant
      ( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
      ( A ) ORGANISM: Human immunodeficiency virus type 1
      ( B ) STRAIN: MAL ( x i ) SEQUENCE DESCRIPTION: SEQ ID NO:9:

Phe Phe Arg Glu Asn Leu Ala Phe Pro Gln Gly Lys Ala Arg Glu Phe
 1               5                  10                  15

Pro Ser Glu Gln Thr Arg Ala Asn Ser Pro Thr Ser Arg Glu Leu Arg
            20                  25                  30

Val Trp Gly Gly Asp Lys Thr Leu Ser Glu Thr Gly Ala Glu Arg Gln
        35                  40                  45

Gly Ile Val Ser Phe Ser Phe Pro Gln Ile Thr Leu Trp Gln Arg Pro

|     |     |     |     |     | 50  |     |     |     |     | 55  |     |     |     |     | 60  |     |     |
| --- | --- | --- | --- | --- | --- | --- | --- | --- | --- | --- | --- | --- | --- | --- | --- | --- | --- |
| Val 65 | Val | Thr | Val | Arg | Val 70 | Gly | Gly | Gln | Leu | Lys 75 | Glu | Ala | Leu | Leu | Asp 80 |
| Thr | Gly | Ala | Asp | Asp 85 | Thr | Val | Leu | Glu | Glu 90 | Ile | Asn | Leu | Pro | Gly 95 | Lys |
| Trp | Lys | Pro | Lys 100 | Met | Ile | Gly | Gly 105 | Ile | Gly | Gly | Phe | Ile 110 | Lys | Val | Arg |
| Gln | Tyr | Asp 115 | Gln | Ile | Leu | Ile | Glu 120 | Ile | Cys | Gly | Lys | Lys 125 | Ala | Ile | Gly |
| Thr | Ile 130 | Leu | Val | Gly | Pro | Thr 135 | Pro | Val | Asn | Ile | Ile 140 | Gly | Arg | Asn | Met |
| Leu 145 | Thr | Gln | Ile | Gly | Cys 150 | Thr | Leu | Asn | Phe | Pro 155 | Ile | Ser | Pro | Ile | Glu 160 |
| Thr | Val | Pro | Val | Lys 165 | Leu | Lys | Pro | Gly | Met 170 | Asp | Gly | Pro | Arg | Val 175 | Lys |
| Gln | Trp | Pro | Leu 180 | Thr | Glu | Glu | Lys | Ile 185 | Lys | Ala | Leu | Thr | Glu 190 | Ile | Cys |
| Lys | Asp | Met 195 | Glu | Lys | Glu | Gly | Lys 200 | Ile | Leu | Lys | Ile | Gly 205 | Pro | Glu | Asn |
| Pro | Tyr 210 | Asn | Thr | Pro | Val | Phe 215 | Ala | Ile | Lys | Lys | Lys 220 | Asp | Ser | Thr | Lys |
| Trp 225 | Arg | Lys | Leu | Val | Asn 230 | Phe | Arg | Glu | Leu | Asn 235 | Lys | Arg | Thr | Gln | Asp 240 |
| Phe | Trp | Glu | Val | Gln 245 | Leu | Gly | Ile | Pro | His 250 | Pro | Ala | Gly | Leu | Lys 255 | Lys |
| Lys | Lys | Ser | Val 260 | Thr | Val | Leu | Asp | Val 265 | Gly | Asp | Ala | Tyr | Phe 270 | Ser | Val |
| Pro | Leu | Asp 275 | Glu | Asp | Phe | Arg | Lys 280 | Tyr | Thr | Ala | Phe | Thr 285 | Ile | Pro | Ser |
| Ile | Asn 290 | Asn | Glu | Thr | Pro | Gly 295 | Ile | Arg | Tyr | Gln | Tyr 300 | Asn | Val | Leu | Pro |
| Gln 305 | Gly | Trp | Lys | Gly | Ser 310 | Pro | Ala | Ile | Phe | Gln 315 | Ser | Ser | Met | Thr | Lys 320 |
| Ile | Leu | Glu | Pro | Phe 325 | Arg | Thr | Lys | Asn | Pro 330 | Glu | Ile | Val | Ile | Tyr 335 | Gln |
| Tyr | Met | Asp | Asp 340 | Leu | Tyr | Val | Gly | Ser 345 | Asp | Leu | Glu | Ile | Gly 350 | Gln | His |
| Arg | Thr | Lys 355 | Ile | Glu | Glu | Leu | Arg 360 | Glu | His | Leu | Leu | Lys 365 | Trp | Gly | Phe |
| Thr | Thr 370 | Pro | Asp | Lys | Lys | His 375 | Gln | Lys | Glu | Pro | Pro 380 | Phe | Leu | Trp | Met |
| Gly 385 | Tyr | Glu | Leu | His | Pro 390 | Asp | Lys | Trp | Thr | Val 395 | Gln | Pro | Ile | Gln | Leu 400 |
| Pro | Asp | Lys | Glu | Ser 405 | Trp | Thr | Val | Asn | Asp 410 | Ile | Gln | Lys | Leu | Val 415 | Gly |
| Lys | Leu | Asn | Trp | Ala 420 | Ser | Gln | Ile | Tyr | Pro 425 | Gly | Ile | Lys | Val 430 | Lys | Gln |
| Leu | Cys | Lys 435 | Leu | Leu | Arg | Gly | Ala 440 | Lys | Ala | Leu | Thr | Asp 445 | Ile | Val | Pro |
| Leu | Thr 450 | Ala | Glu | Ala | Glu | Leu 455 | Glu | Leu | Ala | Glu | Asn 460 | Arg | Glu | Ile | Leu |
| Lys 465 | Glu | Pro | Val | His | Gly 470 | Val | Tyr | Tyr | Asp | Pro 475 | Ser | Lys | Asp | Leu | Ile 480 |

-continued

| | | | | | | | | | | | | | | |
|---|---|---|---|---|---|---|---|---|---|---|---|---|---|---|
|Ala|Glu|Ile|Gln|Lys|Gln|Gly|Gln|Gly|Gln|Trp|Thr|Tyr|Gln|Ile|Tyr|
| | | |485| | | |490| | | | | |495| |
|Gln|Glu|Gln|Tyr|Lys|Asn|Leu|Lys|Thr|Gly|Lys|Tyr|Ala|Arg|Ile|Lys|
| | | |500| | | |505| | | | |510| | |
|Ser|Ala|His|Thr|Asn|Asp|Val|Lys|Gln|Leu|Thr|Glu|Ala|Val|Gln|Lys|
| | |515| | | |520| | | | |525| | | |
|Ile|Ala|Gln|Glu|Ser|Ile|Val|Ile|Trp|Gly|Lys|Thr|Pro|Lys|Phe|Arg|
| |530| | | |535| | | | |540| | | | |
|Leu|Pro|Ile|Gln|Lys|Glu|Thr|Trp|Glu|Ala|Trp|Trp|Thr|Glu|Tyr|Trp|
|545| | | |550| | | |555| | | | | |560| |
|Gln|Ala|Thr|Trp|Ile|Pro|Glu|Trp|Glu|Phe|Val|Asn|Thr|Pro|Pro|Leu|
| | | |565| | | |570| | | | | |575| |
|Val|Lys|Leu|Trp|Tyr|Gln|Leu|Glu|Thr|Glu|Pro|Ile|Val|Gly|Ala|Glu|
| | |580| | | | |585| | | | |590| | |
|Thr|Phe|Tyr|Val|Asp|Gly|Ala|Ala|Asn|Arg|Glu|Thr|Lys|Lys|Gly|Lys|
| |595| | | | |600| | | | |605| | | |
|Ala|Gly|Tyr|Val|Thr|Asp|Arg|Gly|Arg|Gln|Lys|Val|Val|Ser|Leu|Thr|
| |610| | | | |615| | | | |620| | | |
|Glu|Thr|Thr|Asn|Gln|Lys|Thr|Glu|Leu|Gln|Ala|Ile|His|Leu|Ala|Leu|
|625| | | | |630| | | | |635| | | |640|
|Gln|Asp|Ser|Gly|Leu|Glu|Val|Asn|Ile|Val|Thr|Asp|Ser|Gln|Tyr|Ala|
| | | | |645| | | |650| | | | |655| |
|Leu|Gly|Ile|Ile|Gln|Ala|Gln|Pro|Asp|Lys|Ser|Glu|Ser|Glu|Ile|Val|
| | | |660| | | |665| | | | |670| | |
|Asn|Gln|Ile|Ile|Glu|Gln|Leu|Ile|Gln|Lys|Asp|Lys|Val|Tyr|Leu|Ser|
| | |675| | | | |680| | | | |685| | |
|Trp|Val|Pro|Ala|His|Lys|Gly|Ile|Gly|Gly|Asn|Glu|Gln|Val|Asp|Lys|
| |690| | | | |695| | | | |700| | | |
|Leu|Val|Ser|Ser|Gly|Ile|Arg|Lys|Val|Leu|Phe|Leu|Asp|Gly|Ile|Asp|
|705| | | | |710| | | | |715| | | | |720|
|Lys|Ala|Gln|Glu|Glu|His|Glu|Lys|Tyr|His|Ser|Asn|Trp|Arg|Ala|Met|
| | | | |725| | | | |730| | | | |735|
|Ala|Ser|Asp|Phe|Asn|Leu|Pro|Pro|Ile|Val|Ala|Lys|Glu|Ile|Val|Ala|
| | | |740| | | |745| | | | |750| | |
|Ser|Cys|Asp|Lys|Cys|Gln|Leu|Lys|Gly|Glu|Ala|Met|His|Gly|Gln|Val|
| | |755| | | | |760| | | | |765| | |
|Asp|Cys|Ser|Pro|Gly|Ile|Trp|Gln|Leu|Asp|Cys|Thr|His|Leu|Glu|Gly|
| |770| | | | |775| | | | |780| | | |
|Lys|Ile|Ile|Ile|Val|Ala|Val|His|Val|Ala|Ser|Gly|Tyr|Ile|Glu|Ala|
|785| | | | |790| | | | |795| | | | |800|
|Glu|Val|Ile|Pro|Ala|Glu|Thr|Gly|Gln|Glu|Thr|Ala|Tyr|Phe|Ile|Leu|
| | | |805| | | | |810| | | | |815| | |
|Lys|Leu|Ala|Gly|Arg|Trp|Pro|Val|Lys|Val|Val|His|Thr|Asp|Asn|Gly|
| | | |820| | | | |825| | | | |830| | |
|Ser|Asn|Phe|Thr|Ser|Ala|Ala|Val|Lys|Ala|Ala|Cys|Trp|Trp|Ala|Asn|
| | |835| | | | |840| | | | |845| | |
|Ile|Lys|Gln|Glu|Phe|Gly|Ile|Pro|Tyr|Asn|Pro|Gln|Ser|Gln|Gly|Val|
| |850| | | | |855| | | | |860| | | |
|Val|Glu|Ser|Met|Asn|Lys|Glu|Leu|Lys|Lys|Ile|Ile|Gly|Gln|Val|Arg|
|865| | | | |870| | | | |875| | | | |880|
|Glu|Gln|Ala|Glu|His|Leu|Lys|Thr|Ala|Val|Gln|Met|Ala|Val|Phe|Ile|
| | | | |885| | | | |890| | | | |895|
|His|Asn|Phe|Lys|Arg|Lys|Gly|Gly|Ile|Gly|Gly|Tyr|Ser|Ala|Gly|Glu|
| | | |900| | | | |905| | | | |910| |

| Arg | Ile | Ile<br>915 | Asp | Met | Ile | Ala<br>920 | Thr | Asp | Ile | Gln | Thr<br>925 | Lys | Glu | Leu | Gln |
| Lys | Gln<br>930 | Ile | Thr | Lys | Ile | Gln<br>935 | Asn | Phe | Arg | Val | Tyr<br>940 | Tyr | Arg | Asp | Asn |
| Arg<br>945 | Asp | Pro | Ile | Trp | Lys<br>950 | Gly | Pro | Ala | Lys | Leu<br>955 | Leu | Trp | Lys | Gly | Glu<br>960 |
| Gly | Ala | Val | Val | Ile<br>965 | Gln | Asp | Asn | Ser | Asp<br>970 | Ile | Lys | Val | Val | Pro<br>975 | Arg |
| Arg | Lys | Ala | Lys<br>980 | Ile | Ile | Arg | Asp | Tyr<br>985 | Gly | Lys | Gln | Met | Ala<br>990 | Gly | Asp |
| Asp | Cys | Val<br>995 | Ala | Gly | Gly | Gln | Asp<br>1000 | Glu | Asp | Xaa | | | | | |

( 2 ) INFORMATION FOR SEQ ID NO:10:

( i ) SEQUENCE CHARACTERISTICS:
        ( A ) LENGTH: 1003 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Human immunodeficiency virus type 1
        ( B ) STRAIN: ELI ( x i ) SEQUENCE DESCRIPTION: SEQ ID NO:10:

| Phe<br>1 | Phe | Arg | Glu | Asn<br>5 | Leu | Ala | Phe | Pro | Gln<br>10 | Gly | Lys | Ala | Gly | Glu<br>15 | Leu |
| Ser | Pro | Lys | Gln<br>20 | Thr | Arg | Ala | Asn | Ser<br>25 | Pro | Thr | Ser | Arg | Glu<br>30 | Leu | Arg |
| Val | Trp | Gly<br>35 | Arg | Asp | Asn | Pro | Leu<br>40 | Ser | Lys | Thr | Gly | Ala<br>45 | Glu | Arg | Gln |
| Gly<br>50 | Thr | Val | Ser | Phe | Asn<br>55 | Phe | Pro | Gln | Ile | Thr<br>60 | Leu | Trp | Gln | Arg | Pro |
| Leu<br>65 | Val | Ala | Ile | Lys | Ile<br>70 | Gly | Gly | Gln | Leu | Lys<br>75 | Glu | Ala | Leu | Leu | Asp<br>80 |
| Thr | Gly | Ala | Asp | Asp<br>85 | Thr | Val | Leu | Glu | Glu<br>90 | Met | Asn | Leu | Pro | Gly<br>95 | Lys |
| Trp | Lys | Pro | Lys<br>100 | Met | Ile | Gly | Gly | Ile<br>105 | Gly | Gly | Phe | Ile | Lys<br>110 | Val | Arg |
| Gln | Tyr | Asp<br>115 | Gln | Ile | Pro | Ile | Glu<br>120 | Ile | Cys | Gly | Gln | Lys<br>125 | Ala | Ile | Gly |
| Thr | Val<br>130 | Leu | Val | Gly | Pro | Thr<br>135 | Pro | Val | Asn | Ile | Ile<br>140 | Gly | Arg | Asn | Leu |
| Leu<br>145 | Thr | Gln | Ile | Gly | Cys<br>150 | Thr | Leu | Asn | Phe | Pro<br>155 | Ile | Ser | Pro | Ile | Glu<br>160 |
| Thr | Val | Pro | Val | Lys<br>165 | Leu | Lys | Pro | Gly | Met<br>170 | Asp | Gly | Pro | Lys | Val<br>175 | Lys |
| Gln | Trp | Pro | Leu<br>180 | Thr | Glu | Glu | Lys | Ile<br>185 | Lys | Ala | Leu | Thr | Glu<br>190 | Ile | Cys |
| Thr | Asp | Met<br>195 | Glu | Lys | Glu | Gly | Lys<br>200 | Ile | Ser | Arg | Ile | Gly<br>205 | Pro | Glu | Asn |
| Pro | Tyr | Asn | Thr | Pro | Ile | Phe | Ala | Ile | Lys | Lys | Lys | Asp | Ser | Thr | Lys |

```
                      210                      215                      220
Trp  Arg  Lys  Leu  Val  Asp  Phe  Arg  Glu  Leu  Asn  Lys  Arg  Thr  Gln  Asp
225                      230                      235                      240

Phe  Trp  Glu  Val  Gln  Leu  Gly  Ile  Pro  His  Pro  Ala  Gly  Leu  Lys  Lys
                    245                      250                      255

Lys  Lys  Ser  Val  Thr  Val  Leu  Asp  Val  Gly  Asp  Ala  Tyr  Phe  Ser  Val
                    260                      265                      270

Pro  Leu  Asp  Glu  Asp  Phe  Arg  Lys  Tyr  Thr  Ala  Phe  Thr  Ile  Ser  Ser
               275                      280                      285

Ile  Asn  Asn  Glu  Thr  Pro  Gly  Ile  Arg  Tyr  Gln  Tyr  Asn  Val  Leu  Pro
     290                      295                      300

Gln  Gly  Trp  Lys  Gly  Ser  Pro  Ala  Ile  Phe  Gln  Ser  Ser  Met  Thr  Lys
305                      310                      315                      320

Ile  Leu  Glu  Pro  Phe  Arg  Lys  Gln  Asn  Pro  Glu  Met  Val  Ile  Tyr  Gln
                    325                      330                      335

Tyr  Met  Asp  Asp  Leu  Tyr  Val  Gly  Ser  Asp  Leu  Glu  Ile  Gly  Gln  His
               340                      345                      350

Arg  Thr  Lys  Ile  Glu  Lys  Leu  Arg  Glu  His  Leu  Leu  Arg  Trp  Gly  Phe
          355                      360                      365

Thr  Arg  Pro  Asp  Lys  Lys  His  Gln  Lys  Glu  Pro  Pro  Phe  Leu  Trp  Met
     370                      375                      380

Gly  Tyr  Glu  Leu  His  Pro  Asp  Lys  Trp  Thr  Val  Gln  Ser  Ile  Lys  Leu
385                      390                      395                      400

Pro  Glu  Lys  Glu  Ser  Trp  Thr  Val  Asn  Asp  Ile  Gln  Asn  Leu  Val  Glu
                    405                      410                      415

Arg  Leu  Asn  Trp  Ala  Ser  Gln  Ile  Tyr  Pro  Gly  Ile  Lys  Val  Arg  Gln
               420                      425                      430

Leu  Cys  Lys  Leu  Leu  Arg  Gly  Thr  Lys  Ala  Leu  Thr  Glu  Val  Ile  Pro
          435                      440                      445

Leu  Thr  Glu  Glu  Ala  Glu  Leu  Glu  Leu  Ala  Glu  Asn  Arg  Glu  Ile  Leu
     450                      455                      460

Lys  Glu  Pro  Val  His  Gly  Val  Tyr  Tyr  Asp  Pro  Ser  Lys  Asp  Leu  Ile
465                      470                      475                      480

Ala  Glu  Ile  Gln  Lys  Gln  Gly  His  Gly  Gln  Trp  Thr  Tyr  Gln  Ile  Tyr
                    485                      490                      495

Gln  Glu  Pro  Phe  Lys  Asn  Leu  Lys  Thr  Gly  Lys  Tyr  Ala  Arg  Met  Arg
               500                      505                      510

Gly  Ala  His  Thr  Asn  Asp  Val  Lys  Gln  Leu  Ala  Glu  Ala  Val  Gln  Arg
          515                      520                      525

Ile  Ser  Thr  Glu  Ser  Ile  Val  Ile  Trp  Gly  Arg  Thr  Pro  Lys  Phe  Arg
     530                      535                      540

Leu  Pro  Ile  Gln  Lys  Glu  Thr  Trp  Glu  Thr  Trp  Trp  Ala  Glu  Tyr  Trp
545                      550                      555                      560

Gln  Ala  Thr  Trp  Ile  Pro  Glu  Trp  Glu  Phe  Val  Asn  Thr  Pro  Pro  Leu
                    565                      570                      575

Val  Lys  Leu  Trp  Tyr  Gln  Leu  Glu  Lys  Glu  Pro  Ile  Ile  Gly  Ala  Glu
               580                      585                      590

Thr  Phe  Tyr  Val  Asp  Gly  Ala  Ala  Asn  Arg  Glu  Thr  Lys  Leu  Gly  Lys
          595                      600                      605

Ala  Gly  Tyr  Val  Thr  Asp  Arg  Gly  Arg  Gln  Lys  Val  Val  Pro  Leu  Thr
     610                      615                      620

Asp  Thr  Thr  Asn  Gln  Lys  Thr  Glu  Leu  Gln  Ala  Ile  Asn  Leu  Ala  Leu
625                      630                      635                      640
```

-continued

| | | | | | | | | | | | | | | |
|---|---|---|---|---|---|---|---|---|---|---|---|---|---|---|
| Gln | Asp | Ser | Gly | Leu | Glu | Val | Asn | Ile | Val | Thr | Asp | Ser | Gln | Tyr | Ala |
| | | | | 645 | | | | | 650 | | | | | 655 | |
| Leu | Gly | Ile | Ile | Gln | Ala | Gln | Pro | Asp | Lys | Ser | Glu | Ser | Glu | Leu | Val |
| | | | 660 | | | | | 665 | | | | | 670 | | |
| Asn | Gln | Ile | Ile | Glu | Gln | Leu | Ile | Lys | Lys | Glu | Lys | Val | Tyr | Leu | Ala |
| | | | 675 | | | | 680 | | | | | 685 | | | |
| Trp | Val | Pro | Ala | His | Lys | Gly | Ile | Gly | Asn | Glu | Gln | Val | Asp | Lys |
| | | 690 | | | | 695 | | | | 700 | | | | |
| Leu | Val | Ser | Gln | Gly | Ile | Arg | Lys | Val | Leu | Phe | Leu | Asp | Gly | Ile | Asp |
| 705 | | | | | 710 | | | | | 715 | | | | | 720 |
| Lys | Ala | Gln | Glu | Glu | His | Glu | Lys | Tyr | His | Asn | Asn | Trp | Arg | Ala | Met |
| | | | | 725 | | | | | 730 | | | | | 735 | |
| Ala | Ser | Asp | Phe | Asn | Leu | Pro | Pro | Val | Val | Ala | Lys | Glu | Ile | Val | Ala |
| | | | 740 | | | | | 745 | | | | | 750 | | |
| Ser | Cys | Asp | Lys | Cys | Gln | Leu | Lys | Gly | Glu | Ala | Met | His | Gly | Gln | Val |
| | | 755 | | | | | 760 | | | | | 765 | | | |
| Asp | Cys | Ser | Pro | Gly | Ile | Trp | Gln | Leu | Asp | Cys | Thr | His | Leu | Glu | Gly |
| | 770 | | | | | 775 | | | | | 780 | | | | |
| Lys | Val | Ile | Leu | Val | Ala | Val | His | Val | Ala | Ser | Gly | Tyr | Ile | Glu | Ala |
| 785 | | | | | 790 | | | | | 795 | | | | | 800 |
| Glu | Val | Ile | Pro | Ala | Glu | Thr | Gly | Gln | Glu | Thr | Ala | Tyr | Phe | Leu | Leu |
| | | | | 805 | | | | | 810 | | | | | 815 | |
| Lys | Leu | Ala | Gly | Arg | Trp | Pro | Val | Lys | Val | Val | His | Thr | Asp | Asn | Gly |
| | | | | 820 | | | | | 825 | | | | | 830 | |
| Ser | Asn | Phe | Thr | Ser | Ala | Ala | Val | Lys | Ala | Ala | Cys | Trp | Trp | Ala | Gly |
| | | | 835 | | | | | 840 | | | | | 845 | | |
| Ile | Lys | Gln | Glu | Phe | Gly | Ile | Pro | Tyr | Asn | Pro | Gln | Ser | Gln | Gly | Val |
| | | 850 | | | | | 855 | | | | | 860 | | | |
| Val | Glu | Ser | Met | Asn | Lys | Glu | Leu | Lys | Lys | Ile | Ile | Gly | Gln | Val | Arg |
| 865 | | | | | 870 | | | | | 875 | | | | | 880 |
| Asp | Gln | Ala | Glu | His | Leu | Lys | Thr | Ala | Val | Gln | Met | Ala | Val | Phe | Ile |
| | | | | 885 | | | | | 890 | | | | | 895 | |
| His | Asn | Phe | Lys | Arg | Arg | Arg | Gly | Ile | Gly | Gly | Tyr | Ser | Ala | Gly | Glu |
| | | | | 900 | | | | | 905 | | | | | 910 | |
| Arg | Ile | Ile | Asp | Ile | Ile | Ala | Thr | Asp | Ile | Gln | Thr | Lys | Glu | Leu | Gln |
| | | | 915 | | | | | 920 | | | | | 925 | | |
| Lys | Gln | Ile | Ile | Lys | Ile | Gln | Asn | Phe | Arg | Val | Tyr | Tyr | Arg | Asp | Ser |
| | 930 | | | | | 935 | | | | | 940 | | | | |
| Arg | Asp | Pro | Ile | Trp | Lys | Gly | Pro | Ala | Lys | Leu | Leu | Trp | Lys | Gly | Glu |
| 945 | | | | | 950 | | | | | 955 | | | | | 960 |
| Gly | Ala | Val | Val | Ile | Gln | Asp | Lys | Ser | Asp | Ile | Lys | Val | Val | Pro | Arg |
| | | | | 965 | | | | | 970 | | | | | 975 | |
| Arg | Val | Ala | Lys | Ile | Ile | Arg | Asp | Tyr | Gly | Lys | Gln | Met | Ala | Gly | Asp |
| | | | 980 | | | | | 985 | | | | | 990 | | |
| Asp | Cys | Val | Ala | Ser | Arg | Gln | Asp | Glu | Asp | Xaa |
| | | 995 | | | | | 1000 | | | |

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(i i i) HYPOTHETICAL: NO (i v) ANTI-SENSE: NO (v i) ORIGINAL SOURCE:
  (A) ORGANISM: Spodoptera frugiperda
  (B) STRAIN: SF9

(x i) SEQUENCE DESCRIPTION: SEQ ID NO:11:

A C C T A T A A A T                                                                                10

(2) INFORMATION FOR SEQ ID NO:12:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:12:

C G G A T C C T A T   A A A T A T G A G T   T T G C C A G G A                                     29

(2) INFORMATION FOR SEQ ID NO:13:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:13:

T G G C A A A C T C   A T A T T T A T A G   G A T C C G A G C T                                   30

(2) INFORMATION FOR SEQ ID NO:14:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:14:

C A G G A T G A G G   A T T A G G A T C C   G C A T G                                             25

(2) INFORMATION FOR SEQ ID NO:15:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

CGGATCCTAA TCCTCATC                                                                                   18

( 2 ) INFORMATION FOR SEQ ID NO:16:

( i ) SEQUENCE CHARACTERISTICS:
        ( A ) LENGTH: 2739 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Human immunodeficiency virus type 1
        ( B ) STRAIN: HXB2

( x i ) SEQUENCE DESCRIPTION: SEQ ID NO:16:

```
ATGAGTTTGC CAGGAAGATG GAAACCAAAA ATGATAGGGG GAATTGGAGG TTTTATCAAA      60
GTAAGACAGT ATGATCAGAT ACTCATAGAA ATCTGTGGAC ATAAAGCTAT AGGTACAGTA     120
TTAGTAGGAC CTACACCTGT CAACATAATT GGAAGAAATC TGTTGACTCA GATTGGTTGC     180
ACTTTAAATT TTCCCATTAG CCCTATTGAG ACTGTACCAG TAAAATTAAA GCCAGGAATG     240
GATGGCCCAA AAGTTAAACA ATGGCCATTG ACAGAAGAAA AAATAAAAGC ATTAGTAGAA     300
ATTTGTACAG AGATGGAAAA GGAAGGGAAA ATTTCAAAAA TTGGGCCTGA AAATCCATAC     360
AATACTCCAG TATTTGCCAT AAAGAAAAAA GACAGTACTA AATGGAGAAA ATTAGTAGAT     420
TTCAGAGAAC TTAATAAGAG AACTCAAGAC TTCTGGGAAG TTCAATTAGG AATACCACAT     480
CCCGCAGGGT TAAAAAAGAA AAAATCAGTA ACAGTACTGG ATGTGGGTGA TGCATATTTT     540
TCAGTTCCCT TAGATGAAGA CTTCAGGAAG TATACTGCAT TTACCATACC TAGTATAAAC     600
AATGAGACAC CAGGGATTAG ATATCAGTAC AATGTGCTTC CACAGGGATG GAAAGGATCA     660
CCAGCAATAT TCCAAAGTAG CATGACAAAA ATCTTAGAGC CTTTTAGAAA ACAAAATCCA     720
GACATAGTTA TCTATCAATA CATGGATGAT TTGTATGTAG GATCTGACTT AGAAATAGGG     780
CAGCATAGAA CAAAAATAGA GGAGCTGAGA CAACATCTGT TGAGGTGGGG ACTTACCACA     840
CCAGACAAAA AACATCAGAA AGAACCTCCA TTCCTTTGGA TGGGTTATGA ACTCCATCCT     900
GATAAATGGA CAGTACAGCC TATAGTGCTG CCAGAAAAAG ACAGCTGGAC TGTCAATGAC     960
ATACAGAAGT TAGTGGGGAA ATTGAATTGG GCAAGTCAGA TTTACCCAGG GATTAAAGTA    1020
AGGCAATTAT GTAAACTCCT TAGAGGAACC AAAGCACTAA CAGAAGTAAT ACCACTAACA    1080
GAAGAAGCAG AGCTAGAACT GGCAGAAAAC AGAGAGATTC TAAAAGAACC AGTACATGGA    1140
GTGTATTATG ACCCATCAAA AGACTTAATA GCAGAAATAC AGAAGCAGGG CAAGGCCAA     1200
TGGACATATC AAATTTATCA AGAGCCATTT AAAAATCTGA AAACAGGAAA ATATGCAAGA    1260
ATGAGGGGTG CCCACACTAA TGATGTAAAA CAATTAACAG AGGCAGTGCA AAAAATAACC    1320
ACAGAAAGCA TAGTAATATG GGGAAAGACT CCTAAATTTA AACTGCCCAT ACAAAAGGAA    1380
ACATGGGAAA CATGGTGGAC AGAGTATTGG CAAGCCACCT GGATTCCTGA GTGGGAGTTT    1440
GTTAATACCC CTCCCTTAGT GAAATTATGG TACCAGTTAG AGAAAGAACC CATAGTAGGA    1500
GCAGAAACCT TCTATGTAGA TGGGGCAGCT AACAGGGAGA CTAAATTAGG AAAAGCAGGA    1560
```

```
TATGTTACTA  ATAGAGGAAG  ACAAAAAGTT  GTCACCCTAA  CTGACACAAC  AAATCAGAAG   1620

ACTGAGTTAC  AAGCAATTTA  TCTAGCTTTG  CAGGATTCGG  GATTAGAAGT  AAACATAGTA   1680

ACAGACTCAC  AATATGCATT  AGGAATCATT  CAAGCACAAC  CAGATCAAAG  TGAATCAGAG   1740

TTAGTCAATC  AAATAATAGA  GCAGTTAATA  AAAAAGGAAA  AGGTCTATCT  GGCATGGGTA   1800

CCAGCACACA  AAGGAATTGG  AGGAAATGAA  CAAGTAGATA  AATTAGTCAG  TGCTGGAATC   1860

AGGAAAGTAC  TATTTTTAGA  TGGAATAGAT  AAGGCCCAAG  ATGAACATGA  GAAATATCAC   1920

AGTAATTGGA  GAGCAATGGC  TAGTGATTTT  AACCTGCCAC  CTGTAGTAGC  AAAAGAAATA   1980

GTAGCCAGCT  GTGATAAATG  TCAGCTAAAA  GGAGAAGCCA  TGCATGGACA  AGTAGACTGT   2040

AGTCCAGGAA  TATGGCAACT  AGATTGTACA  CATTTAGAAG  GAAAAGTTAT  CCTGGTAGCA   2100

GTTCATGTAG  CCAGTGGATA  TATAGAAGCA  GAAGTTATTC  CAGCAGAAAC  AGGGCAGGAA   2160

ACAGCATATT  TTCTTTTAAA  ATTAGCAGGA  AGATGGCCAG  TAAAACAAT   ACATACTGAC   2220

AATGGCAGCA  ATTTCACCGG  TGCTACGGTT  AGGGCCGCCT  GTTGGTGGGC  GGGAATCAAG   2280

CAGGAATTTG  GAATTCCCTA  CAATCCCCAA  AGTCAAGGAG  TAGTAGAATC  TATGAATAAA   2340

GAATTAAAGA  AAATTATAGG  ACAGGTAAGA  GATCAGGCTG  AACATCTTAA  GACAGCAGTA   2400

CAAATGGCAG  TATTCATCCA  CAATTTTAAA  AGAAAAGGGG  GGATTGGGGG  GTACAGTGCA   2460

GGGGAAAGAA  TAGTAGACAT  AATAGCAACA  GACATACAAA  CTAAAGAATT  ACAAAAACAA   2520

ATTACAAAAA  TTCAAAATTT  TCGGGTTTAT  TACAGGGACA  GCAGAAATTC  ACTTTGGAAA   2580

GGACCAGCAA  AGCTCCTCTG  GAAAGGTGAA  GGGGCAGTAG  TAATACAAGA  TAATAGTGAC   2640

ATAAAGTAG   TGCCAAGAAG  AAAAGCAAAG  ATCATTAGGG  ATTATGGAAA  ACAGATGGCA   2700

GGTGATGATT  GTGTGGCAAG  TAGACAGGAT  GAGGATTAG                            2739
```

( 2 ) INFORMATION FOR SEQ ID NO:17:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

GATCCTATAA ATATG                                                         15

( 2 ) INFORMATION FOR SEQ ID NO:18:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

CATATTTATA G                                                             11

(2) INFORMATION FOR SEQ ID NO:19:

(i) SEQUENCE CHARACTERISTICS:
        (A) LENGTH: 3033 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human immunodeficiency virus type 1
        (B) STRAIN: HXB2

(xi) SEQUENCE DESCRIPTION: SEQ ID NO:19:

```
GGATCCTATA AATATGTTTT TTAGGGAAGA TCTGGCCTTC CTACAAGGGA AGGCCAGGGA      60
ATTTTCTTCA GAGCAGACCA GAGCCAACAG CCCCACCAGA AGAGAGCTTC AGGTCTGGGG     120
TAGAGACAAC AACTCCCCCT CAGAAGCAGG AGCCGATAGA CAAGGAACTG TATCCTTTAA     180
CTTCCCTCAG GTCACTCTTT GGCAACGACC CCTCGTCACA ATAAAGATAG GGGGCAACT      240
AAAGGAAGCT CTATTAGATA CAGGAGCAGA TGATACAGTA TTAGAAGAAA TGAGTTTGCC     300
AGGAAGATGG AAACCAAAAA TGATAGGGGG AATTGGAGGT TTTATCAAAG TAAGACAGTA     360
TGATCAGATA CTCATAGAAA TCTGTGGACA TAAAGCTATA GGTACAGTAT TAGTAGGACC     420
TACACCTGTC AACATAATTG GAAGAAATCT GTTGACTCAG ATTGGTTGCA CTTTAAATTT     480
TCCCATTAGC CCTATTGAGA CTGTACCAGT AAAATTAAAG CCAGGAATGG ATGGCCCAAA     540
AGTTAAACAA TGGCCATTGA CAGAAGAAAA AATAAAAGCA TTAGTAGAAA TTTGTACAGA     600
GATGGAAAAG GAAGGGAAAA TTTCAAAAAT TGGGCCTGAA AATCCATACA ATACTCCAGT     660
ATTTGCCATA AAGAAAAAAG ACAGTACTAA ATGGAGAAAA TTAGTAGATT TCAGAGAACT     720
TAATAAGAGA ACTCAAGACT TCTGGGAAGT TCAATTAGGA ATACCACATC CCGCAGGGTT     780
AAAAAAGAAA AAATCAGTAA CAGTACTGGA TGTGGGTGAT GCATATTTTT CAGTTCCCTT     840
AGATGAAGAC TTCAGGAAGT ATACTGCATT TACCATACCT AGTATAAACA ATGAGACACC     900
AGGGATTAGA TATCAGTACA ATGTGCTTCC ACAGGGATGG AAAGGATCAC CAGCAATATT     960
CCAAAGTAGC ATGACAAAAA TCTTAGAGCC TTTTAGAAAA CAAAATCCAG ACATAGTTAT    1020
CTATCAATAC ATGGATGATT TGTATGTAGG ATCTGACTTA GAAATAGGGC AGCATAGAAC    1080
AAAAATAGAG GAGCTGAGAC AACATCTGTT GAGGTGGGGA CTTACCACAC CAGACAAAAA    1140
ACATCAGAAA GAACCTCCAT TCCTTTGGAT GGGTTATGAA CTCCATCCTG ATAAATGGAC    1200
AGTACAGCCT ATAGTGCTGC CAGAAAAAGA CAGCTGGACT GTCAATGACA TACAGAAGTT    1260
AGTGGGGAAA TTGAATTGGG CAAGTCAGAT TTACCCAGGG ATTAAAGTAA GGCAATTATG    1320
TAAACTCCTT AGAGGAACCA AAGCACTAAC AGAAGTAATA CCACTAACAG AAGAAGCAGA    1380
GCTAGAACTG GCAGAAAACA GAGAGATTCT AAAAGAACCA GTACATGGAG TGTATTATGA    1440
CCCATCAAAA GACTTAATAG CAGAAATACA GAAGCAGGGG CAAGGCCAAT GGACATATCA    1500
AATTTATCAA GAGCCATTTA AAAATCTGAA AACAGGAAAA TATGCAAGAA TGAGGGGTGC    1560
CCACACTAAT GATGTAAAAC AATTAACAGA GGCAGTGCAA AAAATAACCA CAGAAAGCAT    1620
AGTAATATGG GGAAAGACTC CTAAATTTAA ACTGCCCATA CAAAAGGAAA CATGGGAAAC    1680
ATGGTGGACA GAGTATTGGC AAGCCACCTG GATTCCTGAG TGGGAGTTTG TTAATACCCC    1740
TCCCTTAGTG AAATTATGGT ACCAGTTAGA GAAAGAACCC ATAGTAGGAG CAGAAACCTT    1800
```

-continued

| | | | | | |
|---|---|---|---|---|---|
| CTATGTAGAT | GGGGCAGCTA | ACAGGGAGAC | TAAATTAGGA | AAAGCAGGAT | ATGTTACTAA | 1860
| TAGAGGAAGA | CAAAAAGTTG | TCACCCTAAC | TGACACAACA | AATCAGAAGA | CTGAGTTACA | 1920
| AGCAATTTAT | CTAGCTTTGC | AGGATTCGGG | ATTAGAAGTA | AACATAGTAA | CAGACTCACA | 1980
| ATATGCATTA | GGAATCATTC | AAGCACAACC | AGATCAAAGT | GAATCAGAGT | TAGTCAATCA | 2040
| AATAATAGAG | CAGTTAATAA | AAAAGGAAAA | GGTCTATCTG | GCATGGGTAC | CAGCACACAA | 2100
| AGGAATTGGA | GGAAATGAAC | AAGTAGATAA | ATTAGTCAGT | GCTGGAATCA | GGAAAGTACT | 2160
| ATTTTTAGAT | GGAATAGATA | AGGCCCAAGA | TGAACATGAG | AAATATCACA | GTAATTGGAG | 2220
| AGCAATGGCT | AGTGATTTTA | ACCTGCCACC | TGTAGTAGCA | AAAGAAATAG | TAGCCAGCTG | 2280
| TGATAAATGT | CAGCTAAAAG | GAGAAGCCAT | GCATGGACAA | GTAGACTGTA | GTCCAGGAAT | 2340
| ATGGCAACTA | GATTGTACAC | ATTTAGAAGG | AAAAGTTATC | CTGGTAGCAG | TTCATGTAGC | 2400
| CAGTGGATAT | ATAGAAGCAG | AAGTTATTCC | AGCAGAAACA | GGGCAGGAAA | CAGCATATTT | 2460
| TCTTTTAAAA | TTAGCAGGAA | GATGGCCAGT | AAAAACAATA | CATACTGACA | ATGGCAGCAA | 2520
| TTTCACCGGT | GCTACGGTTA | GGGCCGCCTG | TTGGTGGGCG | GAATCAAGC | AGGAATTTGG | 2580
| AATTCCCTAC | AATCCCCAAA | GTCAAGGAGT | AGTAGAATCT | ATGAATAAAG | AATTAAAGAA | 2640
| AATTATAGGA | CAGGTAAGAG | ATCAGGCTGA | ACATCTTAAG | ACAGCAGTAC | AAATGGCAGT | 2700
| ATTCATCCAC | AATTTTAAAA | GAAAAGGGGG | GATTGGGGGG | TACAGTGCAG | GGGAAAGAAT | 2760
| AGTAGACATA | ATAGCAACAG | ACATACAAAC | TAAAGAATTA | CAAAAACAAA | TTACAAAAAT | 2820
| TCAAAATTTT | CGGGTTTATT | ACAGGGACAG | CAGAAATTCA | CTTTGGAAAG | GACCAGCAAA | 2880
| GCTCCTCTGG | AAAGGTGAAG | GGGCAGTAGT | AATACAAGAT | AATAGTGACA | TAAAAGTAGT | 2940
| GCCAAGAAGA | AAAGCAAAGA | TCATTAGGGA | TTATGGAAAA | CAGATGGCAG | GTGATGATTG | 3000
| TGTGGCAAGT | AGACAGGATG | AGGATTAGGA | TCC | | | 3033

(2) INFORMATION FOR SEQ ID NO:20:

(i) SEQUENCE CHARACTERISTICS:
        (A) LENGTH: 3856 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human immunodeficiency virus type 1
        (B) STRAIN: HXB2

(xi) SEQUENCE DESCRIPTION: SEQ ID NO:20:

| | | | | | |
|---|---|---|---|---|---|
| GGATCCTATA | AATATGTACA | GTATTAGAAG | AAATGAGTTT | GCCAGGAAGA | TGGAAACCAA | 60
| AAATGATAGG | GGGAATTGGA | GGTTTTATCA | AGTAAGACA | GTATGATCAG | ATACTCATAG | 120
| AAATCTGTGG | ACATAAAGCT | ATAGGTACAG | TATTAGTAGG | ACCTACACCT | GTCAACATAA | 180
| TTGGAAGAAA | TCTGTTGACT | CAGATTGGTT | GCACTTTAAA | TTTTCCCATT | AGCCCTATTG | 240
| AGACTGTACC | AGTAAAATTA | AAGCCAGGAA | TGGATGGCCC | AAAAGTTAAA | CAATGGCCAT | 300
| TGACAGAAGA | AAAAATAAAA | GCATTAGTAG | AAATTTGTAC | AGAGATGGAA | AAGGAAGGA | 360
| AAATTTCAAA | AATTGGGCCT | GAAAATCCAT | ACAATACTCC | AGTATTTGCC | ATAAAGAAAA | 420
| AAGACAGTAC | TAAATGGAGA | AAATTAGTAG | ATTTCAGAGA | ACTTAATAAG | AGAACTCAAG | 480
| ACTTCTGGGA | AGTTCAATTA | GGAATACCAC | ATCCCGCAGG | GTTAAAAAAG | AAAAAATCAG | 540

```
TAACAGTACT  GGATGTGGGT  GATGCATATT  TTTCAGTTCC  CTTAGATGAA  GACTTCAGGA   600
AGTATACTGC  ATTTACCATA  CCTAGTATAA  ACAATGAGAC  ACCAGGGATT  AGATATCAGT   660
ACAATGTGCT  TCCACAGGGA  TGGAAAGGAT  CACCAGCAAT  ATTCCAAAGT  AGCATGACAA   720
AAATCTTAGA  GCCTTTTAGA  AAACAAAATC  CAGACATAGT  TATCTATCAA  TACATGGATG   780
ATTTGTATGT  AGGATCTGAC  TTAGAAATAG  GGCAGCATAG  AACAAAATA   GAGGAGCTGA   840
GACAACATCT  GTTGAGGTGG  GGACTTACCA  CACCAGACAA  AAAACATCAG  AAAGAACCTC   900
CATTCCTTTG  GATGGGTTAT  GAACTCCATC  CTGATAAATG  GACAGTACAG  CCTATAGTGC   960
TGCCAGAAAA  AGACAGCTGG  ACTGTCAATG  ACATACAGAA  GTTAGTGGGG  AAATTGAATT  1020
GGGCAAGTCA  GATTTACCCA  GGGATTAAAG  TAAGGCAATT  ATGTAAACTC  CTTAGAGGAA  1080
CCAAAGCACT  AACAGAAGTA  ATACCACTAA  CAGAAGAAGC  AGAGCTAGAA  CTGGCAGAAA  1140
ACAGAGAGAT  TCTAAAAGAA  CCAGTACATG  GAGTGTATTA  TGACCCATCA  AAAGACTTAA  1200
TAGCAGAAAT  ACAGAAGCAG  GGGCAAGGCC  AATGGACATA  TCAAATTTAT  CAAGAGCCAT  1260
TTAAAAATCT  GAAAACAGGA  AAATATGCAA  GAATGAGGGG  TGCCCACACT  AATGATGTAA  1320
AACAATTAAC  AGAGGCAGTG  CAAAAAATAA  CCACAGAAAG  CATAGTAATA  TGGGGAAAGA  1380
CTCCTAAATT  TAAACTGCCC  ATACAAAAGG  AAACATGGGA  AACATGGTGG  ACAGAGTATT  1440
GGCAAGCCAC  CTGGATTCCT  GAGTGGGAGT  TTGTTAATAC  CCCTCCCTTA  GTGAAATTAT  1500
GGTACCAGTT  AGAGAAAGAA  CCCATAGTAG  GAGCAGAAAC  CTTCTATGTA  GATGGGGCAG  1560
CTAACAGGGA  GACTAAATTA  GGAAAAGCAG  GATATGTTAC  TAATAGAGGA  AGACAAAAAG  1620
TTGTCACCCT  AACTGACACA  ACAAATCAGA  AGACTGAGTT  ACAAGCAATT  TATCTAGCTT  1680
TGCAGGATTC  GGGATTAGAA  GTAAACATAG  TAACAGACTC  ACAATATGCA  TTAGGAATCA  1740
TTCAAGCACA  ACCAGATCAA  AGTGAATCAG  AGTTAGTCAA  TCAAATAATA  GAGCAGTTAA  1800
TAAAAAGGA   AAAGGTCTAT  CTGGCATGGG  TACCAGCACA  CAAAGGAATT  GGAGGAAATG  1860
AACAAGTAGA  TAAATTAGTC  AGTGCTGGAA  TCAGGAAAGT  ACTATTTTTA  GATGGAATAG  1920
ATAAGGCCCA  AGATGAACAT  GAGAAATATC  ACAGTAATTG  GAGAGCAATG  GCTAGTGATT  1980
TTAACCTGCC  ACCTGTAGTA  GCAAAAGAAA  TAGTAGCCAG  CTGTGATAAA  TGTCAGCTAA  2040
AAGGAGAAGC  CATGCATGGA  CAAGTAGACT  GTAGTCCAGG  AATATGGCAA  CTAGATTGTA  2100
CACATTTAGA  AGGAAAAGTT  ATCCTGGTAG  CAGTTCATGT  AGCCAGTGGA  TATATAGAAG  2160
CAGAAGTTAT  TCCAGCAGAA  ACAGGGCAGG  AAACAGCATA  TTTTCTTTTA  AAATTAGCAG  2220
GAAGATGGCC  AGTAAAAACA  ATACATACTG  ACAATGGCAG  CAATTTCACC  GGTGCTACGG  2280
TTAGGGCCGC  CTGTTGGTGG  GCGGGAATCA  AGCAGGAATT  TGGAATTCCC  TACAATCCCC  2340
AAAGTCAAGG  AGTAGTAGAA  TCTATGAATA  AAGAATTAAA  GAAAATTATA  GGACAGGTAA  2400
GAGATCAGGC  TGAACATCTT  AAGACAGCAG  TACAAATGGC  AGTATTCATC  CACAATTTTA  2460
AAAGAAAAGG  GGGGATTGGG  GGGTACAGTG  CAGGGGAAAG  AATAGTAGAC  ATAATAGCAA  2520
CAGACATACA  AACTAAAGAA  TTACAAAAAC  AAATTACAAA  AATTCAAAAT  TTTCGGGTTT  2580
ATTACAGGGA  CAGCAGAAAT  TCACTTTGGA  AAGGACCAGC  AAAGCTCCTC  TGGAAAGGTG  2640
AAGGGGCAGT  AGTAATACAA  GATAATAGTG  ACATAAAAGT  AGTGCCAAGA  AGAAAAGCAA  2700
AGATCATTAG  GGATTATGGA  AAACAGATGG  CAGGTGATGA  TTGTGTGGCA  AGTAGACAGG  2760
ATGAGGATTA  GGATCCGGAA  AAGTTTAGTA  AAACACCATA  TGTATGTTTC  AGGGAAAGCT  2820
AGGGGATGGT  TTTATAGACA  TCACTATGAA  AGCCCTCATC  CAAGAATAAG  TTCAGAAGTA  2880
CACATCCCAC  TAGGGGATGC  TAGATTGGTA  ATAACAACAT  ATTGGGTCT   GCATACAGGA  2940
```

| GAAAGAGACT | GGCATTTGGG | TCAGGGAGTC | TCCATAGAAT | GGAGGAAAAA | GAGATATAGC | 3000 |
| ACACAAGTAG | ACCCTGAACT | AGCAGACCAA | CTAATTCATC | TGTATTACTT | TGACTGTTTT | 3060 |
| TCAGACTCTG | CTATAAGAAA | GGCCTTATTA | GGACACATAG | TTAGCCCTAG | GTGTGAATAT | 3120 |
| CAAGCAGGAC | ATAACAAGGT | AGGATCTCTA | CAATACTTGG | CACTAGCAGC | ATTAATAACA | 3180 |
| CCAAAAAAGA | TAAAGCCACC | TTTGCCTAGT | GTTACGAAAC | TGACAGAGGA | TAGATGGAAC | 3240 |
| AAGCCCCAGA | AGACCAAGGG | CCACAGAGGG | AGCCACACAA | TGAATGGACA | CTAGAGCTTT | 3300 |
| TAGAGGAGCT | TAAGAATGAA | GCTGTTAGAC | ATTTTCCTAG | GATTTGGCTC | CATGGCTTAG | 3360 |
| GGCAACATAT | CTATGAAACT | TATGGGGATA | CTTGGGCAGG | AGTGGAAGCC | ATAATAAGAA | 3420 |
| TTCTGCAACA | ACTGCTGTTT | ATCCATTTTC | AGAATTGGGT | GTCGACATAG | CAGAATAGGC | 3480 |
| GTTACTCGAC | AGAGGAGAGC | AAGAAATGGA | GCCAGTAGAT | CCTAGACTAG | AGCCCTGGAA | 3540 |
| GCATCCAGGA | AGTCAGCCTA | AAACTGCTTG | TACCAATTGC | TATTGTAAAA | AGTGTTGCTT | 3600 |
| TCATTGCCAA | GTTTGTTTCA | TAACAAAAGC | CTTAGGCATC | TCCTATGGCA | GGAAGAAGCG | 3660 |
| GAGACAGCGA | CGAAGAGCTC | ATCAGAACAG | TCAGACTCAT | CAAGCTTCTC | TATCAAAGCA | 3720 |
| GTAAGTAGTA | CATGTAACGC | AACCTATACC | AATAGTAGCA | ATAGTAGCAT | TAGTAGTAGC | 3780 |
| AATAATAATA | GCAATAGTTG | TGTGGTCCAT | AGTAATCATA | GAATATAGGA | AAATATTAAG | 3840 |
| ACAAAGAAAA | ATAGAC | | | | | 3856 |

(2) INFORMATION FOR SEQ ID NO:21:

(i) SEQUENCE CHARACTERISTICS:
        (A) LENGTH: 4113 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human immunodeficiency virus type 1
        (B) STRAIN: HXB2

(xi) SEQUENCE DESCRIPTION: SEQ ID NO:21:

| GGATCCTATA | AATATGTTTT | TTAGGGAAGA | TCTGGCCTTC | CTACAAGGGA | AGGCCAGGGA | 60 |
| ATTTTCTTCA | GAGCAGACCA | GAGCCAACAG | CCCCACCAGA | AGAGAGCTTC | AGGTCTGGGG | 120 |
| TAGAGACAAC | AACTCCCCCT | CAGAAGCAGG | AGCCGATAGA | CAAGGAACTG | TATCCTTTAA | 180 |
| CTTCCCTCAG | GTCACTCTTT | GGCAACGACC | CCTCGTCACA | ATAAAGATAG | GGGGCAACT | 240 |
| AAAGGAAGCT | CTATTAGATA | CAGGAGCAGA | TGATACAGTA | TTAGAAGAAA | TGAGTTTGCC | 300 |
| AGGAAGATGG | AAACCAAAAA | TGATAGGGGG | AATTGGAGGT | TTTATCAAAG | TAAGACAGTA | 360 |
| TGATCAGATA | CTCATAGAAA | TCTGTGGACA | TAAAGCTATA | GGTACAGTAT | TAGTAGGACC | 420 |
| TACACCTGTC | AACATAATTG | GAAGAAATCT | GTTGACTCAG | ATTGGTTGCA | CTTTAAATTT | 480 |
| TCCCATTAGC | CCTATTGAGA | CTGTACCAGT | AAAATTAAAG | CCAGGAATGG | ATGGCCCAAA | 540 |
| AGTTAAACAA | TGGCCATTGA | CAGAAGAAAA | AATAAAGCA | TTAGTAGAAA | TTTGTACAGA | 600 |
| GATGGAAAAG | GAAGGGAAAA | TTTCAAAAAT | TGGGCCTGAA | AATCCATACA | ATACTCCAGT | 660 |
| ATTTGCCATA | AAGAAAAAAG | ACAGTACTAA | ATGGAGAAAA | TTAGTAGATT | TCAGAGAACT | 720 |
| TAATAAGAGA | ACTCAAGACT | TCTGGGAAGT | TCAATTAGGA | ATACCACATC | CCGCAGGGTT | 780 |

```
AAAAAGAAA   AAATCAGTAA   CAGTACTGGA   TGTGGGTGAT   GCATATTTTT   CAGTTCCCTT    840

AGATGAAGAC   TTCAGGAAGT   ATACTGCATT   TACCATACCT   AGTATAAACA   ATGAGACACC    900

AGGGATTAGA   TATCAGTACA   ATGTGCTTCC   ACAGGGATGG   AAAGGATCAC   CAGCAATATT    960

CCAAAGTAGC   ATGACAAAAA   TCTTAGAGCC   TTTTAGAAAA   CAAAATCCAG   ACATAGTTAT   1020

CTATCAATAC   ATGGATGATT   TGTATGTAGG   ATCTGACTTA   GAAATAGGGC   AGCATAGAAC   1080

AAAATAGAG    GAGCTGAGAC   AACATCTGTT   GAGGTGGGGA   CTTACCACAC   CAGACAAAAA   1140

ACATCAGAAA   GAACCTCCAT   TCCTTTGGAT   GGGTTATGAA   CTCCATCCTG   ATAAATGGAC   1200

AGTACAGCCT   ATAGTGCTGC   CAGAAAAAGA   CAGCTGGACT   GTCAATGACA   TACAGAAGTT   1260

AGTGGGGAAA   TTGAATTGGG   CAAGTCAGAT   TTACCCAGGG   ATTAAAGTAA   GGCAATTATG   1320

TAAACTCCTT   AGAGGAACCA   AAGCACTAAC   AGAAGTAATA   CCACTAACAG   AAGAAGCAGA   1380

GCTAGAACTG   GCAGAAAACA   GAGAGATTCT   AAAAGAACCA   GTACATGGAG   TGTATTATGA   1440

CCCATCAAAA   GACTTAATAG   CAGAAATACA   GAAGCAGGGG   CAAGGCCAAT   GGACATATCA   1500

AATTTATCAA   GAGCCATTTA   AAAATCTGAA   AACAGGAAAA   TATGCAAGAA   TGAGGGGTGC   1560

CCACACTAAT   GATGTAAAAC   AATTAACAGA   GGCAGTGCAA   AAAATAACCA   CAGAAAGCAT   1620

AGTAATATGG   GGAAAGACTC   CTAAATTTAA   ACTGCCCATA   CAAAAGGAAA   CATGGGAAAC   1680

ATGGTGGACA   GAGTATTGGC   AAGCCACCTG   GATTCCTGAG   TGGGAGTTTG   TTAATACCCC   1740

TCCCTTAGTG   AAATTATGGT   ACCAGTTAGA   GAAAGAACCC   ATAGTAGGAG   CAGAAACCTT   1800

CTATGTAGAT   GGGGCAGCTA   ACAGGGAGAC   TAAATTAGGA   AAAGCAGGAT   ATGTTACTAA   1860

TAGAGGAAGA   CAAAAAGTTG   TCACCCTAAC   TGACACAACA   AATCAGAAGA   CTGAGTTACA   1920

AGCAATTTAT   CTAGCTTTGC   AGGATTCGGG   ATTAGAAGTA   ACATAGTAA    CAGACTCACA   1980

ATATGCATTA   GGAATCATTC   AAGCACAACC   AGATCAAAGT   GAATCAGAGT   TAGTCAATCA   2040

AATAATAGAG   CAGTTAATAA   AAAGGAAAA    GGTCTATCTG   GCATGGGTAC   CAGCACACAA   2100

AGGAATTGGA   GGAAATGAAC   AAGTAGATAA   ATTAGTCAGT   GCTGGAATCA   GGAAAGTACT   2160

ATTTTTAGAT   GGAATAGATA   AGGCCCAAGA   TGAACATGAG   AAATATCACA   GTAATTGGAG   2220

AGCAATGGCT   AGTGATTTTA   ACCTGCCACC   TGTAGTAGCA   AAAGAAATAG   TAGCCAGCTG   2280

TGATAAATGT   CAGCTAAAAG   GAGAAGCCAT   GCATGGACAA   GTAGACTGTA   GTCCAGGAAT   2340

ATGGCAACTA   GATTGTACAC   ATTTAGAAGG   AAAAGTTATC   CTGGTAGCAG   TTCATGTAGC   2400

CAGTGGATAT   ATAGAAGCAG   AAGTTATTCC   AGCAGAAACA   GGGCAGGAAA   CAGCATATTT   2460

TCTTTTAAAA   TTAGCAGGAA   GATGGCCAGT   AAAAACAATA   CATACTGACA   ATGGCAGCAA   2520

TTTCACCGGT   GCTACGGTTA   GGGCCGCCTG   TTGGTGGGCG   GAATCAAGC    AGGAATTTGG   2580

AATTCCCTAC   AATCCCCAAA   GTCAAGGAGT   AGTAGAATCT   ATGAATAAAG   AATTAAAGAA   2640

AATTATAGGA   CAGGTAAGAG   ATCAGGCTGA   ACATCTTAAG   ACAGCAGTAC   AAATGGCAGT   2700

ATTCATCCAC   AATTTTAAAA   GAAAAGGGGG   GATTGGGGGG   TACAGTGCAG   GGGAAAGAAT   2760

AGTAGACATA   ATAGCAACAG   ACATACAAAC   TAAAGAATTA   CAAAAACAAA   TTACAAAAAT   2820

TCAAAATTTT   CGGGTTTATT   ACAGGGACAG   CAGAAATTCA   CTTTGGAAAG   GACCAGCAAA   2880

GCTCCTCTGG   AAAGGTGAAG   GGGCAGTAGT   AATACAAGAT   AATAGTGACA   TAAAAGTAGT   2940

GCCAAGAAGA   AAAGCAAAGA   TCATTAGGGA   TTATGGAAAA   CAGATGGCAG   GTGATGATTG   3000

TGTGGCAAGT   AGACAGGATG   AGGATTAGGA   TCCGGAAAAG   TTTAGTAAAA   CACCATATGT   3060

ATGTTTCAGG   GAAAGCTAGG   GGATGGTTTT   ATAGACATCA   CTATGAAAGC   CCTCATCCAA   3120

GAATAAGTTC   AGAAGTACAC   ATCCCACTAG   GGGATGCTAG   ATTGGTAATA   ACAACATATT   3180
```

| | | | | | |
|---|---|---|---|---|---|
| GGGGTCTGCA | TACAGGAGAA | AGAGACTGGC | ATTTGGGTCA | GGGAGTCTCC | ATAGAATGGA | 3240 |
| GGAAAAAGAG | ATATAGCACA | CAAGTAGACC | CTGAACTAGC | AGACCAACTA | ATTCATCTGT | 3300 |
| ATTACTTTGA | CTGTTTTTCA | GACTCTGCTA | TAAGAAAGGC | CTTATTAGGA | CACATAGTTA | 3360 |
| GCCCTAGGTG | TGAATATCAA | GCAGGACATA | ACAAGGTAGG | ATCTCTACAA | TACTTGGCAC | 3420 |
| TAGCAGCATT | AATAACACCA | AAAAGATAA | AGCCACCTTT | GCCTAGTGTT | ACGAAACTGA | 3480 |
| CAGAGGATAG | ATGGAACAAG | CCCCAGAAGA | CCAAGGGCCA | CAGAGGGAGC | CACACAATGA | 3540 |
| ATGGACACTA | GAGCTTTTAG | AGGAGCTTAA | GAATGAAGCT | GTTAGACATT | TTCCTAGGAT | 3600 |
| TTGGCTCCAT | GGCTTAGGGC | AACATATCTA | TGAAACTTAT | GGGGATACTT | GGGCAGGAGT | 3660 |
| GGAAGCCATA | ATAAGAATTC | TGCAACAACT | GCTGTTTATC | CATTTTCAGA | ATTGGGTGTC | 3720 |
| GACATAGCAG | AATAGGCGTT | ACTCGACAGA | GGAGAGCAAG | AAATGGAGCC | AGTAGATCCT | 3780 |
| AGACTAGAGC | CCTGGAAGCA | TCCAGGAAGT | CAGCCTAAAA | CTGCTTGTAC | CAATTGCTAT | 3840 |
| TGTAAAAAGT | GTTGCTTTCA | TTGCCAAGTT | TGTTTCATAA | CAAAAGCCTT | AGGCATCTCC | 3900 |
| TATGGCAGGA | AGAAGCGGAG | ACAGCGACGA | AGAGCTCATC | AGAACAGTCA | GACTCATCAA | 3960 |
| GCTTCTCTAT | CAAAGCAGTA | AGTAGTACAT | GTAACGCAAC | CTATACCAAT | AGTAGCAATA | 4020 |
| GTAGCATTAG | TAGTAGCAAT | AATAATAGCA | ATAGTTGTGT | GGTCCATAGT | AATCATAGAA | 4080 |
| TATAGGAAAA | TATTAAGACA | AAGAAAAATA | GAC | | | 4113 |

( 2 ) INFORMATION FOR SEQ ID NO:22:

( i ) SEQUENCE CHARACTERISTICS:
        ( A ) LENGTH: 913 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Human immunodeficiency virus type 1
        ( B ) STRAIN: HXB2

( x i ) SEQUENCE DESCRIPTION: SEQ ID NO:22:

```
Met  Ser  Leu  Pro  Gly  Arg  Trp  Lys  Pro  Lys  Met  Ile  Gly  Gly  Ile  Gly
 1              5                        10                       15

Gly  Phe  Ile  Lys  Val  Arg  Gln  Tyr  Asp  Gln  Ile  Leu  Ile  Glu  Ile  Cys
               20                       25                       30

Gly  His  Lys  Ala  Ile  Gly  Thr  Val  Leu  Val  Gly  Pro  Thr  Pro  Val  Asn
          35                       40                       45

Ile  Ile  Gly  Arg  Asn  Leu  Leu  Thr  Gln  Ile  Gly  Cys  Thr  Leu  Asn  Phe
     50                       55                       60

Pro  Ile  Ser  Pro  Ile  Glu  Thr  Val  Pro  Val  Lys  Leu  Lys  Pro  Gly  Met
 65                      70                       75                       80

Asp  Gly  Pro  Lys  Val  Lys  Gln  Trp  Pro  Leu  Thr  Glu  Glu  Lys  Ile  Lys
                    85                       90                       95

Ala  Leu  Val  Glu  Ile  Cys  Thr  Glu  Met  Glu  Lys  Glu  Gly  Lys  Ile  Ser
                    100                      105                      110

Lys  Ile  Gly  Pro  Glu  Asn  Pro  Tyr  Asn  Thr  Pro  Val  Phe  Ala  Ile  Lys
          115                      120                      125

Lys  Lys  Asp  Ser  Thr  Lys  Trp  Arg  Lys  Leu  Val  Asp  Phe  Arg  Glu  Leu
          130                      135                      140
```

```
Asn  Lys  Arg  Thr  Gln  Asp  Phe  Trp  Glu  Val  Gln  Leu  Gly  Ile  Pro  His
145                 150                      155                      160

Pro  Ala  Gly  Leu  Lys  Lys  Lys  Ser  Val  Thr  Val  Leu  Asp  Val  Gly
                    165                 170                 175

Asp  Ala  Tyr  Phe  Ser  Val  Pro  Leu  Asp  Glu  Asp  Phe  Arg  Lys  Tyr  Thr
               180                      185                      190

Ala  Phe  Thr  Ile  Pro  Ser  Ile  Asn  Asn  Glu  Thr  Pro  Gly  Ile  Arg  Tyr
          195                      200                      205

Gln  Tyr  Asn  Val  Leu  Pro  Gln  Gly  Trp  Lys  Gly  Ser  Pro  Ala  Ile  Phe
          210                      215                 220

Gln  Ser  Ser  Met  Thr  Lys  Ile  Leu  Glu  Pro  Phe  Arg  Lys  Gln  Asn  Pro
225                      230                 235                           240

Asp  Ile  Val  Ile  Tyr  Gln  Tyr  Met  Asp  Leu  Tyr  Val  Gly  Ser  Asp
                    245                      250                      255

Leu  Glu  Ile  Gly  Gln  His  Arg  Thr  Lys  Ile  Glu  Glu  Leu  Arg  Gln  His
               260                      265                      270

Leu  Leu  Arg  Trp  Gly  Leu  Thr  Thr  Pro  Asp  Lys  Lys  His  Gln  Lys  Glu
               275                      280                      285

Pro  Pro  Phe  Leu  Trp  Met  Gly  Tyr  Glu  Leu  His  Pro  Asp  Lys  Trp  Thr
290                      295                      300

Val  Gln  Pro  Ile  Val  Leu  Pro  Glu  Lys  Asp  Ser  Trp  Thr  Val  Asn  Asp
305                      310                      315                      320

Ile  Gln  Lys  Leu  Val  Gly  Lys  Leu  Asn  Trp  Ala  Ser  Gln  Ile  Tyr  Pro
                    325                      330                      335

Gly  Ile  Lys  Val  Arg  Gln  Leu  Cys  Lys  Leu  Leu  Arg  Gly  Thr  Lys  Ala
               340                      345                      350

Leu  Thr  Glu  Val  Ile  Pro  Leu  Thr  Glu  Glu  Ala  Glu  Leu  Glu  Leu  Ala
               355                      360                      365

Glu  Asn  Arg  Glu  Ile  Leu  Lys  Glu  Pro  Val  His  Gly  Val  Tyr  Tyr  Asp
370                      375                      380

Pro  Ser  Lys  Asp  Leu  Ile  Ala  Glu  Ile  Gln  Lys  Gln  Gly  Gln  Gly  Gln
385                      390                      395                      400

Trp  Thr  Tyr  Gln  Ile  Tyr  Gln  Glu  Pro  Phe  Lys  Asn  Leu  Lys  Thr  Gly
                    405                      410                      415

Lys  Tyr  Ala  Arg  Met  Arg  Gly  Ala  His  Thr  Asn  Asp  Val  Lys  Gln  Leu
               420                      425                      430

Thr  Glu  Ala  Val  Gln  Lys  Ile  Thr  Thr  Glu  Ser  Ile  Val  Ile  Trp  Gly
               435                      440                      445

Lys  Thr  Pro  Lys  Phe  Lys  Leu  Pro  Ile  Gln  Lys  Glu  Thr  Trp  Glu  Thr
     450                      455                      460

Trp  Trp  Thr  Glu  Tyr  Trp  Gln  Ala  Thr  Trp  Ile  Pro  Glu  Trp  Glu  Phe
465                      470                      475                      480

Val  Asn  Thr  Pro  Pro  Leu  Val  Lys  Leu  Trp  Tyr  Gln  Leu  Glu  Lys  Glu
                    485                      490                      495

Pro  Ile  Val  Gly  Ala  Glu  Thr  Phe  Tyr  Val  Asp  Gly  Ala  Ala  Asn  Arg
               500                      505                      510

Glu  Thr  Lys  Leu  Gly  Lys  Ala  Gly  Tyr  Val  Thr  Asn  Arg  Gly  Arg  Gln
               515                      520                      525

Lys  Val  Val  Thr  Leu  Thr  Asp  Thr  Thr  Asn  Gln  Lys  Thr  Glu  Leu  Gln
               530                      535                      540

Ala  Ile  Tyr  Leu  Ala  Leu  Gln  Asp  Ser  Gly  Leu  Glu  Val  Asn  Ile  Val
545                      550                      555                      560

Thr  Asp  Ser  Gln  Tyr  Ala  Leu  Gly  Ile  Ile  Gln  Ala  Gln  Pro  Asp  Gln
                    565                      570                      575
```

```
Ser  Glu  Ser  Glu  Leu  Val  Asn  Gln  Ile  Ile  Glu  Gln  Leu  Ile  Lys  Lys
               580                     585                    590

Glu  Lys  Val  Tyr  Leu  Ala  Trp  Val  Pro  Ala  His  Lys  Gly  Ile  Gly  Gly
          595                     600                      605

Asn  Glu  Gln  Val  Asp  Lys  Leu  Val  Ser  Ala  Gly  Ile  Arg  Lys  Val  Leu
     610                     615                    620

Phe  Leu  Asp  Gly  Ile  Asp  Lys  Ala  Gln  Asp  Glu  His  Glu  Lys  Tyr  His
625                     630                    635                         640

Ser  Asn  Trp  Arg  Ala  Met  Ala  Ser  Asp  Phe  Asn  Leu  Pro  Pro  Val  Val
               645                     650                              655

Ala  Lys  Glu  Ile  Val  Ala  Ser  Cys  Asp  Lys  Cys  Gln  Leu  Lys  Gly  Glu
               660                     665                    670

Ala  Met  His  Gly  Gln  Val  Asp  Cys  Ser  Pro  Gly  Ile  Trp  Gln  Leu  Asp
          675                     680                    685

Cys  Thr  His  Leu  Glu  Gly  Lys  Val  Ile  Leu  Val  Ala  Val  His  Val  Ala
     690                    695                         700

Ser  Gly  Tyr  Ile  Glu  Ala  Glu  Val  Ile  Pro  Ala  Glu  Thr  Gly  Gln  Glu
705                     710                    715                         720

Thr  Ala  Tyr  Phe  Leu  Leu  Lys  Leu  Ala  Gly  Arg  Trp  Pro  Val  Lys  Thr
               725                    730                     735

Ile  His  Thr  Asp  Asn  Gly  Ser  Asn  Phe  Thr  Gly  Ala  Thr  Val  Arg  Ala
               740                    745                     750

Ala  Cys  Trp  Trp  Ala  Gly  Ile  Lys  Gln  Glu  Phe  Gly  Ile  Pro  Tyr  Asn
          755                    760                     765

Pro  Gln  Ser  Gln  Gly  Val  Val  Glu  Ser  Met  Asn  Lys  Glu  Leu  Lys  Lys
     770                    775                     780

Ile  Ile  Gly  Gln  Val  Arg  Asp  Gln  Ala  Glu  His  Leu  Lys  Thr  Ala  Val
785                     790                    795                         800

Gln  Met  Ala  Val  Phe  Ile  His  Asn  Phe  Lys  Arg  Lys  Gly  Gly  Ile  Gly
               805                    810                     815

Gly  Tyr  Ser  Ala  Gly  Glu  Arg  Ile  Val  Asp  Ile  Ile  Ala  Thr  Asp  Ile
               820                    825                     830

Gln  Thr  Lys  Glu  Leu  Gln  Lys  Gln  Ile  Thr  Lys  Ile  Gln  Asn  Phe  Arg
          835                    840                     845

Val  Tyr  Tyr  Arg  Asp  Ser  Arg  Asn  Ser  Leu  Trp  Lys  Gly  Pro  Ala  Lys
     850                    855                     860

Leu  Leu  Trp  Lys  Gly  Glu  Gly  Ala  Val  Val  Ile  Gln  Asp  Asn  Ser  Asp
865                    870                     875                         880

Ile  Lys  Val  Val  Pro  Arg  Arg  Lys  Ala  Lys  Ile  Ile  Arg  Asp  Tyr  Gly
               885                    890                     895

Lys  Gln  Met  Ala  Gly  Asp  Asp  Cys  Val  Ala  Ser  Arg  Gln  Asp  Glu  Asp
               900                    905                     910

Xaa
```